(12) United States Patent
Spies et al.

(10) Patent No.: US 10,040,853 B2
(45) Date of Patent: Aug. 7, 2018

(54) METHODS AND COMPOSITIONS INVOLVING NKG2D INHIBITORS AND CANCER

(75) Inventors: Thomas Spies, Seattle, WA (US); Veronika Spies, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 9 days.

(21) Appl. No.: 14/343,543

(22) PCT Filed: Sep. 7, 2012

(86) PCT No.: PCT/US2012/054214
§ 371 (c)(1),
(2), (4) Date: Jun. 25, 2014

(87) PCT Pub. No.: WO2013/036799
PCT Pub. Date: Mar. 14, 2013

(65) Prior Publication Data
US 2014/0377266 A1    Dec. 25, 2014

Related U.S. Application Data

(60) Provisional application No. 61/533,061, filed on Sep. 9, 2011.

(51) Int. Cl.
| | | |
|---|---|---|
| A61K 38/00 | (2006.01) | |
| C07K 16/30 | (2006.01) | |
| C07K 16/28 | (2006.01) | |
| A61K 38/17 | (2006.01) | |
| A61K 31/7105 | (2006.01) | |
| C12N 15/113 | (2010.01) | |
| A61K 39/00 | (2006.01) | |

(52) U.S. Cl.
CPC ...... C07K 16/2815 (2013.01); A61K 31/7105 (2013.01); A61K 38/17 (2013.01); C07K 16/2833 (2013.01); C07K 16/2851 (2013.01); C07K 16/30 (2013.01); C12N 15/1138 (2013.01); *A61K 2039/505* (2013.01); *C07K 2317/21* (2013.01); *C07K 2317/24* (2013.01); *C07K 2317/54* (2013.01); *C07K 2317/76* (2013.01); *C12N 2310/14* (2013.01); *C12N 2330/51* (2013.01)

(58) Field of Classification Search
CPC ................................ A61K 38/00; C07K 16/30
USPC ....................................................... 424/135.1
See application file for complete search history.

(56) References Cited

U.S. PATENT DOCUMENTS

| | | | |
|---|---|---|---|
| 4,415,723 A | 11/1983 | Hedges et al. | 528/204 |
| 4,458,066 A | 7/1984 | Caruthers et al. | 536/25.34 |
| 4,554,101 A | 11/1985 | Hopp | 530/324 |
| 4,683,195 A | 7/1987 | Mullis et al. | 435/6.11 |
| 4,683,202 A | 7/1987 | Mullis | 435/91.2 |
| 4,797,368 A | 1/1989 | Carter et al. | 435/320.1 |
| 4,800,159 A | 1/1989 | Mullis et al. | 435/91.2 |
| 4,816,567 A | 3/1989 | Cabilly et al. | 530/387.3 |
| 4,883,750 A | 11/1989 | Whiteley et al. | 435/6.16 |
| 5,139,941 A | 8/1992 | Muzyczka et al. | 435/456 |
| 5,187,260 A | 2/1993 | Karali et al. | 530/358 |
| 5,279,721 A | 1/1994 | Schmid | 204/457 |
| 5,795,715 A | 8/1998 | Livache et al. | 435/6.18 |
| 5,840,873 A | 11/1998 | Nelson et al. | 536/24.3 |
| 5,843,640 A | 12/1998 | Patterson et al. | 435/5 |
| 5,843,650 A | 12/1998 | Segev | 435/6.1 |
| 5,843,651 A | 12/1998 | Stimpson et al. | 435/6.11 |
| 5,843,663 A | 12/1998 | Stanley et al. | 435/6.11 |
| 5,846,708 A | 12/1998 | Hollis et al. | 506/12 |
| 5,846,709 A | 12/1998 | Segev | 435/6.1 |
| 5,846,717 A | 12/1998 | Brow et al. | 435/6.18 |
| 5,846,726 A | 12/1998 | Nadeau et al. | 435/6.12 |
| 5,846,729 A | 12/1998 | Wu et al. | 435/6.12 |
| 5,846,783 A | 12/1998 | Wu et al. | 435/91.2 |
| 5,849,481 A | 12/1998 | Urdea et al. | 435/6.11 |
| 5,849,486 A | 12/1998 | Heller et al. | 435/6.11 |
| 5,849,487 A | 12/1998 | Hase et al. | 435/6.12 |
| 5,849,497 A | 12/1998 | Steinman | 435/6.11 |
| 5,849,546 A | 12/1998 | Sousa et al. | 435/91.5 |
| 5,849,547 A | 12/1998 | Cleuziat et al. | 435/91.21 |
| 5,851,772 A | 12/1998 | Mirzabekov et al. | 435/6.14 |
| 5,853,990 A | 12/1998 | Winger et al. | 435/6.18 |
| 5,853,992 A | 12/1998 | Glazer et al. | 435/6.12 |
| 5,853,993 A | 12/1998 | Dellinger et al. | 435/6.14 |
| 5,856,092 A | 1/1999 | Dale et al. | 435/6.11 |
| 5,858,652 A | 1/1999 | Laffler et al. | 435/5 |
| 5,861,244 A | 1/1999 | Wang et al. | 435/6.14 |
| 5,863,732 A | 1/1999 | Richards | 435/6.1 |
| 5,863,753 A | 1/1999 | Haugland et al. | 435/34 |
| 5,866,331 A | 2/1999 | Singer et al. | 435/6.11 |

(Continued)

FOREIGN PATENT DOCUMENTS

| | | |
|---|---|---|
| EP | 320 308 | 6/1989 |
| EP | 329 822 | 8/1989 |

(Continued)

OTHER PUBLICATIONS

Gura (Science. 1997; 278: 1041-1042).*
Dennis (Nature. Aug. 7, 2006; 442: 739-741).*
Aksentijevich et al., *Hum. Gene Ther.*, 7(9):1111-1122, 1996.
Bellus, *J. Macromol. Sci. Pure Appl. Chem.*, A31(1): 1355-1376, 1994.
Bosher and Labouesse, *Nat. Cell. Biol.*, 2(2):E31-E36, 2000.
Caplen et al., *Gene*, 252(1-2):95-105, 2000.
Chada, S., et al. (2003). INGN 241 (Ad.mda-7) induces widespread apoptosis and activates the immune system in patients with advanced cancer. Mol. Ther. 7: S446.
Clackson et al., *Nature*, 352:624-628, 1991.

(Continued)

Primary Examiner — Yan Xiao
(74) Attorney, Agent, or Firm — Norton Rose Fulbright US LLP

(57) ABSTRACT

Embodiments methods and compositions involving inhibitors of the immunoreceptor Natural Killer Group 2, Member D, (NKG2D) for inhibiting tumor progression and treating cancer.

14 Claims, 23 Drawing Sheets

(56) References Cited

U.S. PATENT DOCUMENTS

| | | | |
|---|---|---|---|
| 5,866,366 A | 2/1999 | Kallender | 435/69.1 |
| 5,882,864 A | 3/1999 | An et al. | 435/6.14 |
| 5,889,136 A | 3/1999 | Scaringe et al. | 536/25.34 |
| 5,900,481 A | 5/1999 | Lough et al. | 506/30 |
| 5,905,024 A | 5/1999 | Mirzabekov et al. | 435/6.12 |
| 5,910,407 A | 6/1999 | Vogelstein et al. | 435/6.14 |
| 5,912,124 A | 6/1999 | Kumar et al. | 435/6.12 |
| 5,912,145 A | 6/1999 | Stanley | 435/91.1 |
| 5,912,148 A | 6/1999 | Eggerding | 435/91.2 |
| 5,916,776 A | 6/1999 | Kumar | 435/91.1 |
| 5,916,779 A | 6/1999 | Pearson et al. | 435/91.2 |
| 5,919,626 A | 7/1999 | Shi et al. | 435/6.14 |
| 5,919,630 A | 7/1999 | Nadeau et al. | 435/6.12 |
| 5,922,574 A | 7/1999 | Minter | 435/91.1 |
| 5,925,517 A | 7/1999 | Tyagi et al. | 435/6.1 |
| 5,928,862 A | 7/1999 | Morrison | 435/6.18 |
| 5,928,869 A | 7/1999 | Nadeau et al. | 435/6.18 |
| 5,928,905 A | 7/1999 | Stemmer et al. | 435/91.1 |
| 5,928,906 A | 7/1999 | Koster et al. | 435/91.2 |
| 5,929,227 A | 7/1999 | Glazer et al. | 536/26.6 |
| 5,932,413 A | 8/1999 | Celebuski | 435/6.11 |
| 5,932,451 A | 8/1999 | Wang et al. | 435/91.21 |
| 5,935,791 A | 8/1999 | Nadeau et al. | 435/6.18 |
| 5,935,825 A | 8/1999 | Nishimura et al. | 435/91.2 |
| 5,939,291 A | 8/1999 | Loewy et al. | 435/91.2 |
| 5,942,391 A | 8/1999 | Zhang et al. | 435/6.12 |
| 6,458,350 B1 * | 10/2002 | Cosman | C07K 14/705 424/85.1 |
| 7,771,718 B2 * | 8/2010 | Spies | C07K 14/70539 424/130.1 |
| 8,182,809 B1 * | 5/2012 | Wu | A61K 39/0011 424/130.1 |
| 2003/0147966 A1 | 8/2003 | Franzen | 424/491 |
| 2003/0223938 A1 | 12/2003 | Nagy et al. | 424/46 |
| 2005/0143336 A1 | 6/2005 | Ramesh et al. | 514/44 |
| 2007/0077241 A1 * | 4/2007 | Spies | C07K 16/2851 424/133.1 |
| 2010/0056764 A1 * | 3/2010 | Urso | C07K 16/2851 530/388.15 |

FOREIGN PATENT DOCUMENTS

| | | |
|---|---|---|
| GB | 2 202 328 | 9/1988 |
| WO | WO 84/03564 | 9/1984 |
| WO | WO 88/10315 | 12/1988 |
| WO | WO 89/06700 | 7/1989 |
| WO | WO 90/07641 | 7/1990 |
| WO | WO 98/07408 | 2/1998 |
| WO | WO 99/32619 | 7/1999 |
| WO | WO 00/44914 | 8/2000 |
| WO | WO 01/68836 | 9/2001 |
| WO | WO 2010/017103 | * 2/2010 |

OTHER PUBLICATIONS

Coffin, In: *Virology*, Fields et al. (Eds.), Raven Press, NY, 1437-1500, 1990.
Consortium, *Nucleic Acids Res.*, 34:D322-326, 2006.
Creighton et al., "Epithelial-Mesenchymal Transition (EMT) in Tumor-Initiating Cells and Its Clinical Implications in Breast Cancer" *J. Mammary Gland Biol. Neoplasia*, 15:253-260, 2010.
Dreyfuss et al., *Am. Rev. Respir. Dis.*, 137:1159-1164, 1988.
Dudek et al., *Free Radic. Biol. Med.*, 31:651-658, 2001.
Elbashir et al., "Duplexes of 21-nucleotide RNAs mediate RNA interference in cultured mammalian cells" *Nature*, 411(6836):494-498, 2001.
Felgner et al., "Lipofection: A highly efficient, lipid-mediated DNA-transfection procedure" *Proc. Natl. Acad. Sci. USA*, 84(21):7413-7417, 1987.
Fire et al., "Potent and specific genetic interference by double-stranded RNA in Caenorhabditis elegans." *Nature*, 391(6669):806-811, 1998.
Fodor et al., *Science*, 251:767-777, 1991.
Fraley et al., *Proc. Natl. Acad. Sci. USA*, 76:3348-3352, 1979.
Gabizon et al., *Cancer Res.*, 50(19):6371-6378, 1990.
Garcia et al., *Oncogene*, 20:2499-2513, 2001.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Grishok, A., Tabara, H., and Mello, C.C. 2000. "Genetic requirements for inheritance of RNAi in C. elegans." Science 287: 2494-2497.
Hacia et al., *Nature Genet.*, 14:441-449, 1996.
Holen et al., "The pharmacokinetics, toxicities, and biologic effects of FK866, a nicotinamide adenine dinucleotide biosynthesis inhibitor." *Invest. New Drugs*, 26:45-51, 2008.
Innis et al., "DNA sequencing with Thermus aquaticus DNA polymerase and direct sequencing of polymerase chain reaction-amplified DNA" *Proc. Natl. Acad. Sci. USA*, 85(24):9436-9440, 1988.
Inouye and Inouye, *Nucleic Acids Res.*, 13:3101-3109, 1985.
Jia et al., *J. Clin. Invest.*, 113:1318-1327, 2004.
Kaneda et al., "Increased expression of DNA cointroduced with nuclear protein in adult rat liver." *Science*, 243:375-378, 1989.
Karlsson et al., *EMBO J.*, 5:2377-2385, 1986.
Kato K, Nakanishi M, Kaneda Y, Uchida T and Okada Y. (1991a). "Expression of Hepatitis B virus surface antigen in adult rat liver." J. Biol. Chem., 266, 3361-3364.
Ketting et al., *Cell*, 99(2):133-141, 1999.
Kohler and Milstein, "Continuous cultures of fused cells secreting antibody of predefined specificity." *Nature*, 256:495-497, 1975.
Kwoh et al., *Proc. Natl. Acad. Sci. USA*, 86:1173, 1989.
Li and Wong, "Model-based analysis of oligonucleotide arrays: expression index computation and outlier detection." *Proc. Natl. Acad. Sci. USA*, 98:31-36, 2001.
Lin and Avery, *Nature*, 402:128-129, 1999.
Liu TJ, el-Naggar AK, McDonnell TJ, Steck KD, Wang M, Taylor DL, Clayman GL. Apoptosis induction mediated by wild-type p53 adenoviral gene transfer in squamous cell carcinoma of the head and neck. Cancer Res. Jul. 15, 1995;55(14):3117-3122.
Logullo AF, et al. 2010. Concomitant expression of epithelial-mesenchymal transition biomarkers in breast ductal carcinoma: association with progression. Oncol. Rep. 23:313-320.
Luscher et al., *Neth. J. Med.*, 50(5):204-210, 1997.
Ma et al., *Am. J. Physiol. Lung Cell Mol. Physiol.*, 289:L468-477, 2005.
Macejak and Sarnow, *Nature*, 353:90-94, 1991.
Mann et al., *Cell*, 33:153-159, 1983.
Marks et al., *J. Mol. Biol.*, 222:581-597, 1991.
Moitra et al., *Transl. Res.*, 150:253-265, 2007.
Montgomery et al., *Proc. Natl. Acad. Sci. USA*, 95:15502-15507, 1998.
Nichols et al., *Development*, 110:1341-1348, 1990.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nonas et al., *Am. J. Physiol. Lung Cell Mol. Physiol.*, 293:L292-302, 2007.
Ohara et al., *Proc. Natl. Acad. Sci. USA*, 86:5673-5677, 1989.
Paskind et al., *Virology*, 67:242-248, 1975.
Pearson, *Radiology*, 179(1):9-14, 1991.
Pease et al., *Proc. Natl. Acad. Sci. USA*, 91:5022-5026, 1994.
Pelletier and Sonenberg, *Nature*, 334(6180):320-325, 1988.
Peng et al., *Am. J. Respir. Crit. Care Med.*, 169:1245-1251, 2004.
Polyak and Weinberg, *Nat. Rev. Cancer*, 9:265-273, 2009.
Ranieri et al., *JAMA*, 282:54-61, 1999.
Remington's Pharmaceutical Sciences 15$^{th}$ Ed., 1035-1038 and 1570-1580, 1990.
Revollo et al., *Cell Metab.*, 6(5):363-375, 2007.
Revollo et al., *J. Biol Chem.*, 279(49):50754-50763, 2004.
Rubenfeld et al., *N. Engl. J. Med.*, 353:1685-1693, 2005.
Samal et al., *Mol. Cell Biol.*, 14(2):1431-1417, 1994.
Sharp and Zamore, *Science*, 287:2431-2433, 2000.
Sharp, *Genes Dev.*, 13:139-141, 1999.

(56) References Cited

OTHER PUBLICATIONS

Shoemaker et al., *Nature Genetics*, 14:450-456, 1996.
Slutsky and Tremblay, *Am. J. Respir. Crit. Care Med.*, 157:1721-1725, 1998.
Smyth-Templeton et al., *DNA Cell Biol.*, 21(12):857-867, 1997.
Solodin et al., *Biochemistry*, 34(41):13537-13544, 1995.
Strauss et al., *PLoS One*, 6:e16186, 2011.
Tabara et al., *Cell*, 99(2):123-132, 1999.
Temin, *In: Gene Transfer*, Kucherlapati (Ed.), NY, Plenum Press, 149-188, 1986.
Templeton et al., *Nat. Biotechnol.*, 15(7):647-652, 1997.
The acute respiratory distress syndrome network, *N. Engl. J. Med.*, 342:1301-1308, 2000.
Thierry et al., *Proc. Natl. Acad. Sci. USA*, 92(21):9742-9746, 1995.
Thierry et al., *Cell*, 139:871-890, 2009.
Toole, *Nat. Rev. Cancer*, 4(7):528-539, 2004.
Tremblay et al., *Crit. Care Med.*, 30:1693-1700, 2002.
Tremblay et al., *J. Clin. Invest.*, 99:944-952, 1997.
Tsukamoto et al., *Nat. Genet.*, 9(3):243-248, 1995.
Turley et al., *J. Biol. Chem.*, 277(7):4589-4592, 2002.
Walker et al., *Nucleic Acids Res.* 20(7):1691-1696, 1992.
Ware and Matthay, *N. Engl. J. Med.*, 342:1334-1349, 2000.
Wincott et al., *Nucleic Acids Res.*, 23(14):2677-2684, 1995.
Wong et al., *Gene*, 10:87-94, 1980.
Wu et al., *J. Am. Stat. Assoc.*, 99:909-917, 2004.
Yang and Huang, *Gene Therapy*, 4 (9):950-960, 1997.
Yang and Weinberg, *Dev. Cell*, 14:818-829, 2008.
Ye et al., *Am. J. Respir. Crit. Care Med.*, 171:361-370, 2005.
Yilmaz and Christofori, *Cancer Metastasis Rev.*, 28:15-33, 2009.
Zhu et al., *Science*, 261(5118):209-211, 1993.
Benitez, et al. "Expression, signaling proficiency, and stimulatory function of the NKG2D lymphocyte receptor in human cancer cells" PNAS, Mar. 8, 2011, vol. 108, No. 10, 4081-4086.
Cai, et al. "Autonomous Stimulation of Cancer Cell Plasticity by the Human NKG2D Lymphocyte Receptor Coexpressed with Its Ligands on Cancer Cells" PLOS One, Oct. 2014, vol. 9, Issue 10, e108942.
El-Gazzar, et al. "Immunobiology and Conflicting Roles of the Human NKG2D Lymphocyte Receptor and Its Ligands in Cancer" J Immunol 2013; 191:1509-1515.
El-Gazzar et al. "Effects on tumor development and metastatic dissemination by the NKG2D lymphocyte receptor expressed on cancer cells" Oncogene (2014) 33, 4932-4940.
Wu, Jennifer "Antibody targeting soluble NKG2D ligan sMIC refuels and invigorates the endogenous immune system to fight cancer" Oncoimmunology, 2016, vol. 5, No. 3, e1095434.

\* cited by examiner

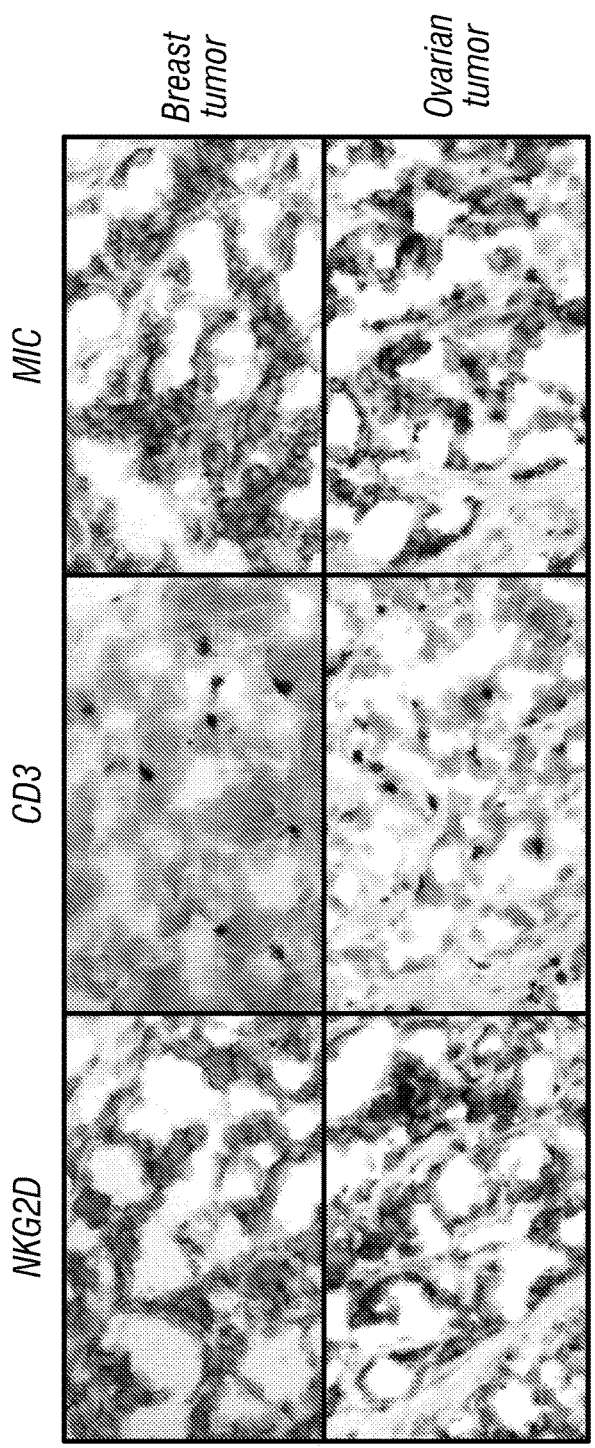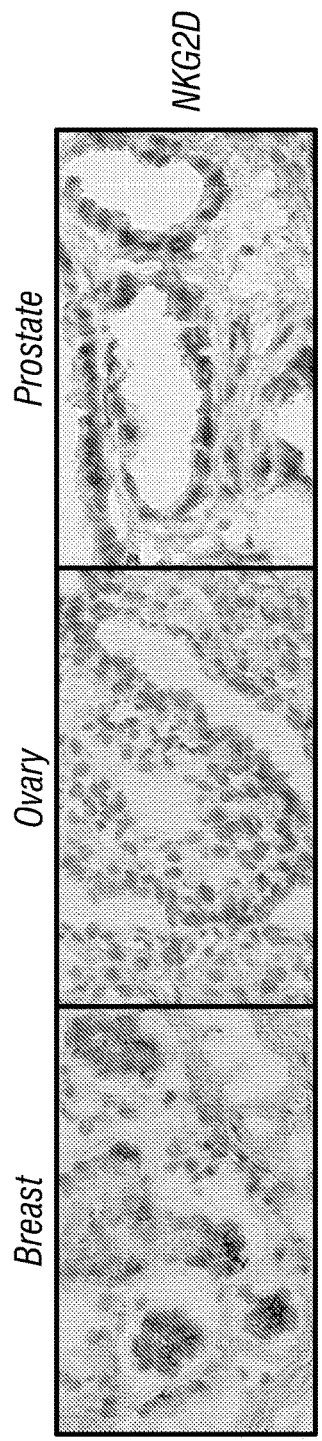
FIG. 1A
FIG. 1B

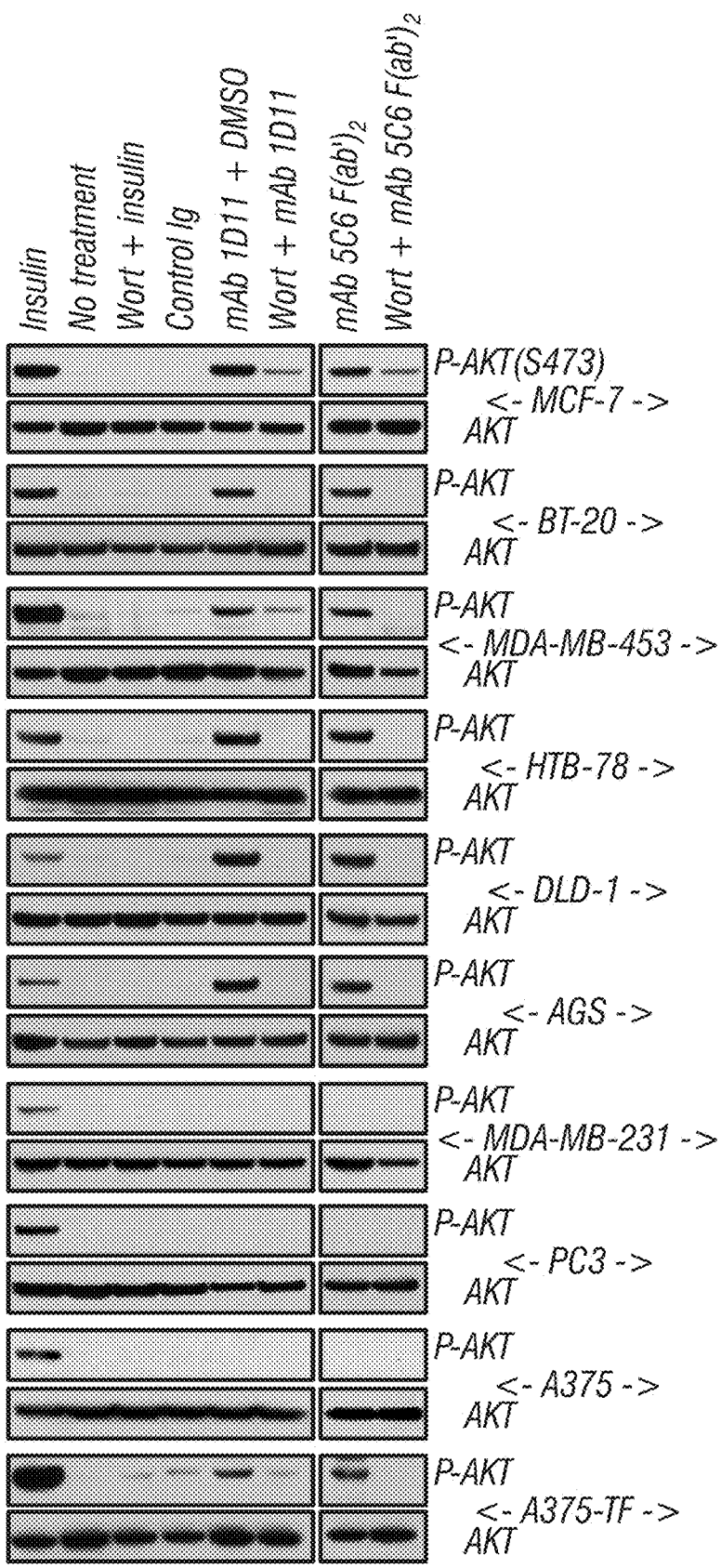
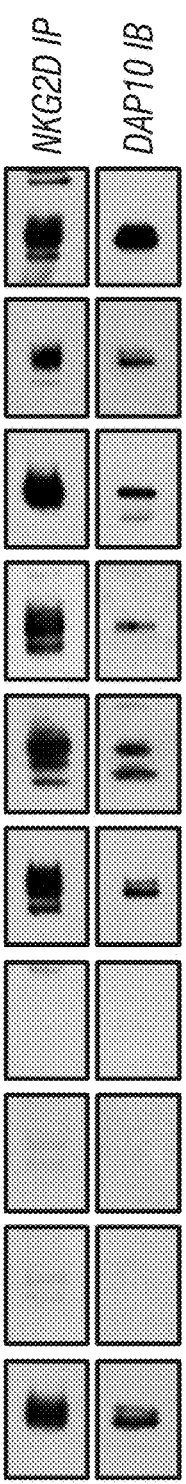
*FIG. 2A*     *FIG. 2B*

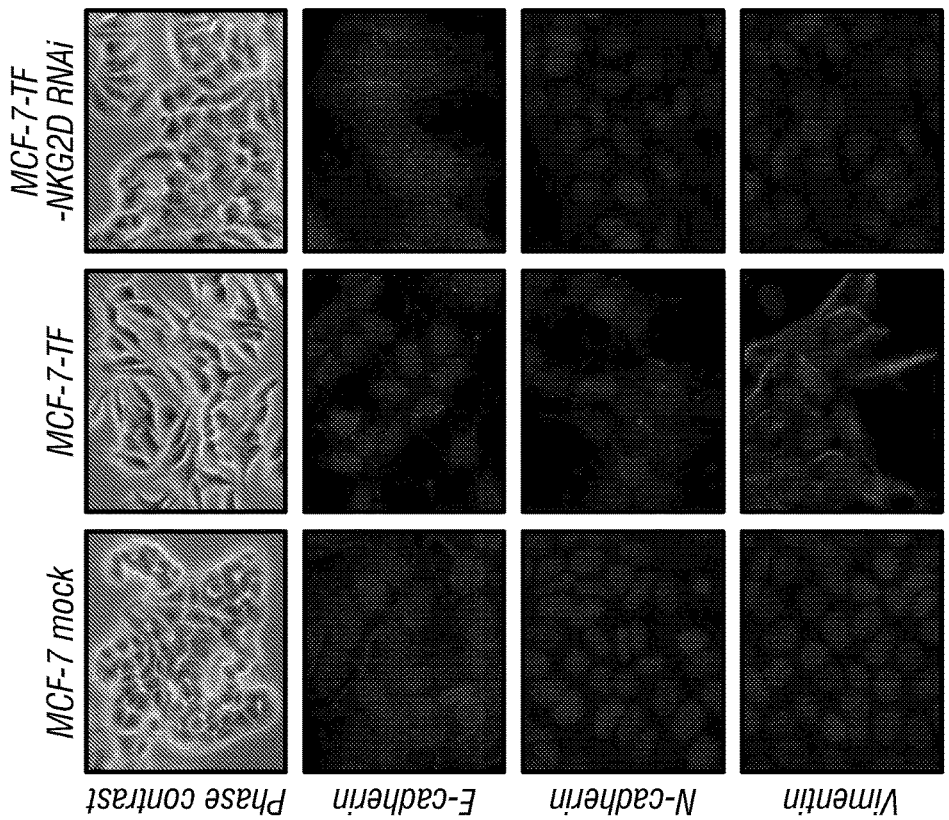
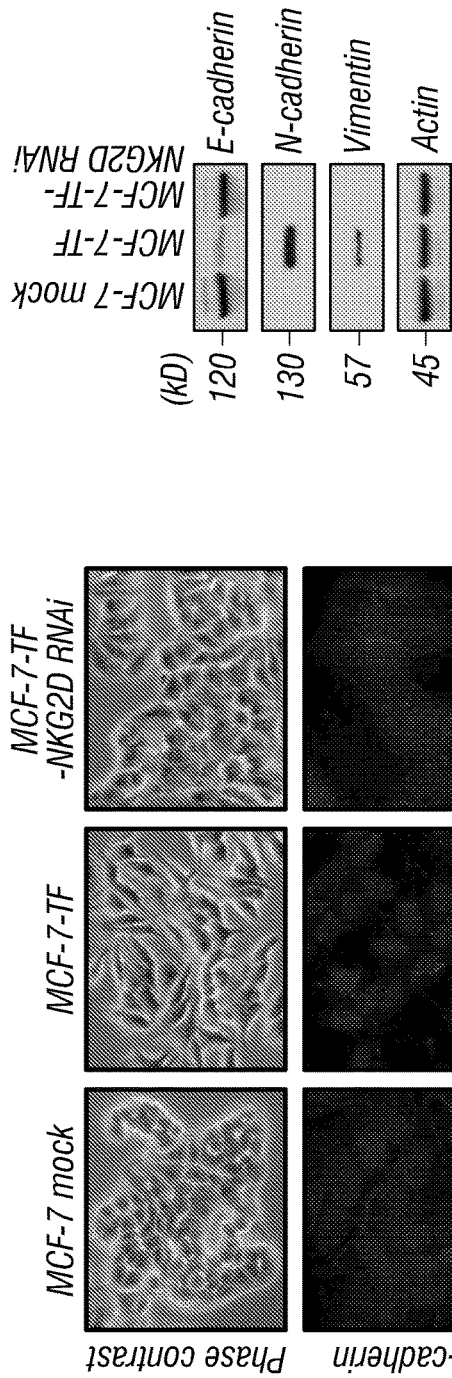
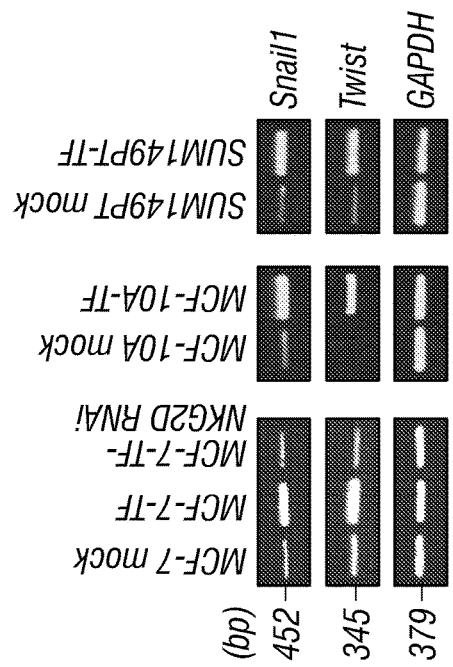
FIG. 8A
FIG. 8B
FIG. 8C

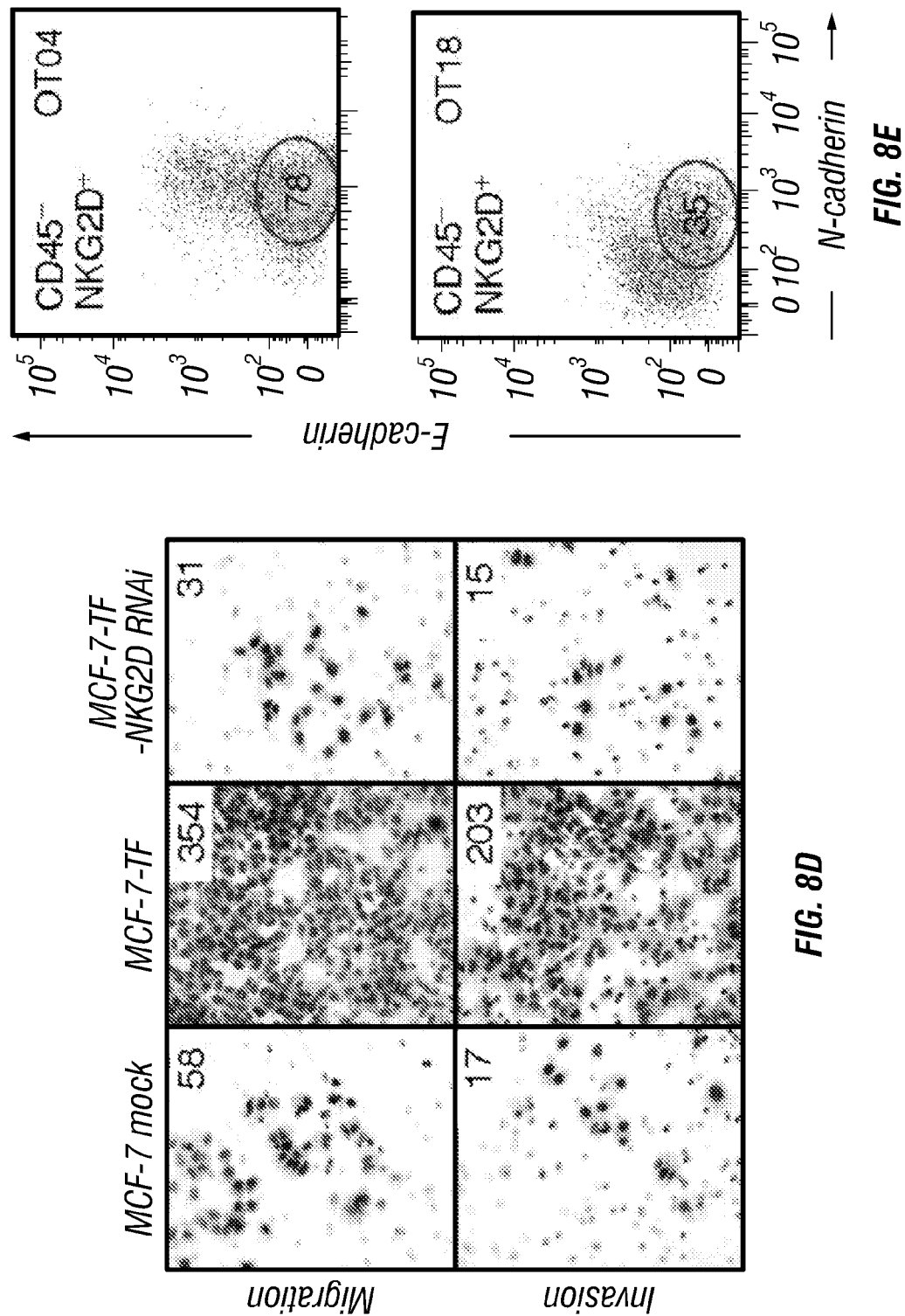

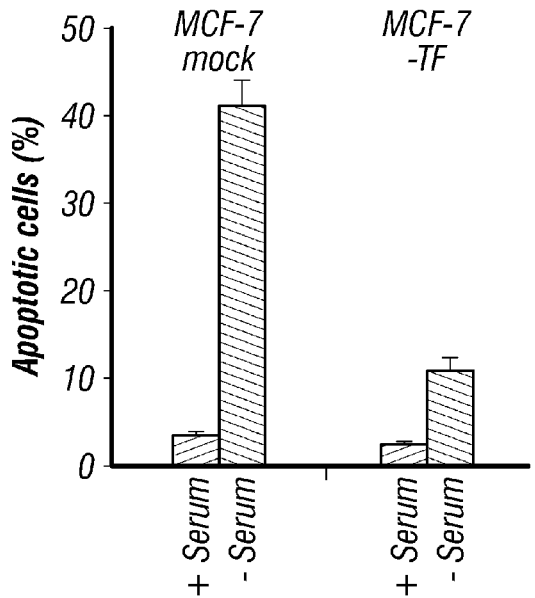
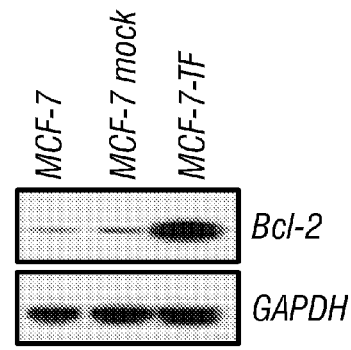
FIG. 9A
FIG. 9B
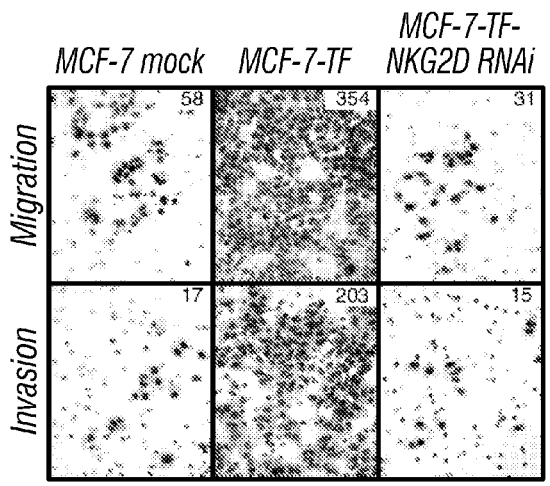
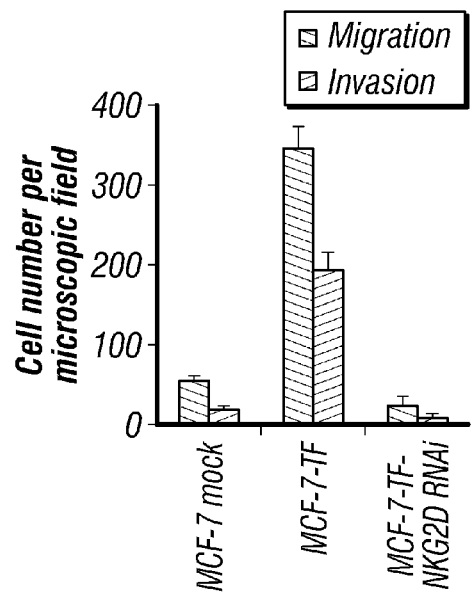
FIG. 10

Intravasation

MCF-7 mock    MCF-7-TF

Local invasion

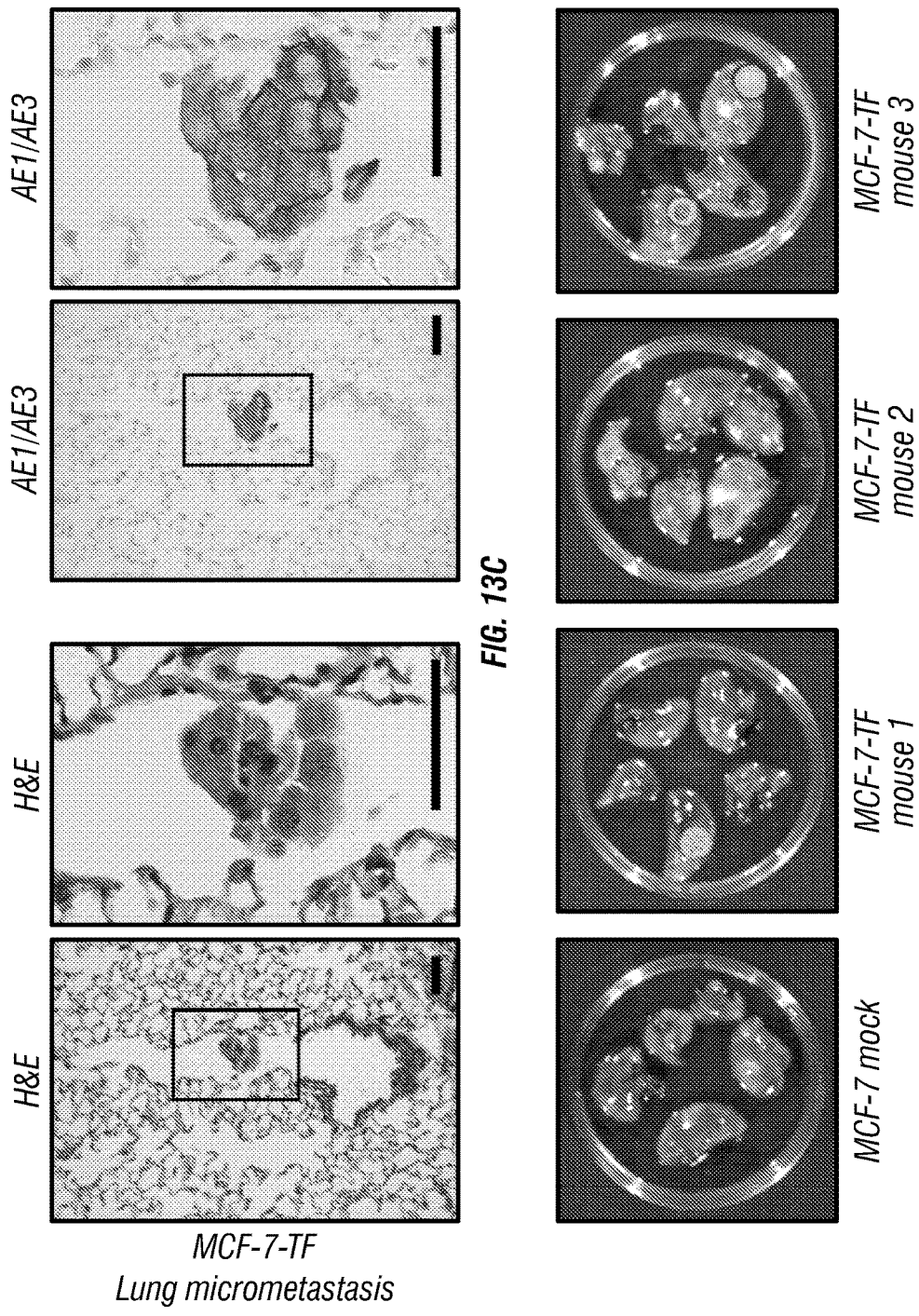

METHODS AND COMPOSITIONS INVOLVING NKG2D INHIBITORS AND CANCER

This application is a national phase application under 35 U.S.C. 371 of International Application No. PCT/US2012/054214 filed Sep. 7, 2012 which claims the benefit of priority to U.S. Provisional Patent Application Ser. No. 61/533,061, filed Sep. 9, 2011, which are hereby incorporated by reference in their entirety.

This invention was made with government support under AI030581 awarded by the National Institutes of Health. The government has certain rights in the invention.

BACKGROUND OF THE INVENTION

I. Field of the Invention

The present invention relates generally to the fields of medicine, oncology, and molecular biology. More particularly, it concerns methods and compositions involving NKG2D inhibitors and preventative, therapeutic, and diagnostic applications for cancer.

II. Background

The role of the immune system in cancer is related to immunosurveillance—a process by which the immune system monitors the body for transformed cells in order to destroy them. Tumor immune surveillance is mediated by the NKG2D lymphocyte receptor, which stimulates natural killer (NK) and CD8 T cell responses against cancer cells expressing its ligands. With advanced human cancers, however, persistent NKG2D ligand expression favors tumor progression, which has been ascribed to ligand-induced immune evasion.

Despite improved understanding of cancer and cancer treatment, additional therapies are needed.

SUMMARY OF THE INVENTION

There are examples showing that NKG2D is expressed on cancer cells together with its ligands and that inhibition of NKG2D receptor activity results in positive benefits. Therefore, embodiments concern methods and compositions involving NKG2D inhibitors for preventative and therapeutic applications for cancer and tumor progression. The terms "NKG2D" and "NKG2D receptor" are used interchangeably to refer to the human NKG2D immunoreceptor, unless a different animal species is recited or discussed.

Some embodiments concern methods for inhibiting tumor progression in a cancer patient comprising administering to the patient a composition comprising an NKG2D inhibitor. Other embodiments concern methods for treating cancer in a patient comprising administering to the patient a composition comprising an NKG2D inhibitor. Further embodiments concern methods of inhibiting a cancer cell that expresses NKG2D.

The term "NKG2D inhibitor" refers to a substance or compound that inhibits one or more properties of NKG2D. Such properties include competing with at least one natural NKG2D ligand, or with several ligands, in binding to NKG2D; reducing the amount of NKG2D on the surface of a NKG2D-expressing cancer or tumor cell; reducing the amount of NKG2D expression; reducing expression of DAP10; binding cynomolgous and/or rhesus NKG2D; binding only one antibody molecule per NKG2D dimer; cross-linking no more than 2 NKG2D dimers when added to NKG2D-expressing cancer cells; having insignificant or undetectable agonist effect on NKG2D signaling upon binding; and/or, binding to NKG2D with a dissociation constant ($K_D$) of 1 nM or less. Certain anti-NKG2D antibodies may also or alternatively compete with, bind to essentially the same epitope as, or bind with the same or higher affinity as, one or more particular human anti-NKG2D antibodies described herein, including antibodies MS and 21F2. For example, in one embodiment, the antibodies are also, or alternatively, more capable of competing with or blocking NKG2D-binding of MS and/or 21F2 than known murine anti-NKG2D antibodies that are known. In one embodiment, the antibodies bind to the same NKG2D epitope as MS and/or 21F2. In another embodiment, the antibodies also or alternatively bind the same epitope as MS. In another embodiment, the antibodies also or alternatively bind the same epitope as 21F2. The skilled person will understand that antibodies provided by and/or used in embodiments may exhibit three, four, or more of the above-referenced features. It is specifically contemplated that embodiments may involve NKG2D inhibitors that are antagonists of NKG2D and not agonists. In certain embodiments, an NKG2D inhibitor does not include a compound or substance that reduces the expression of DAP10.

In specific embodiments, a NKG2D inhibitor is a NKG2D activity inhibitor, meaning the inhibitor directly inhibits NKG2D by acting on the NKG2D polypeptide and inhibiting the activity of the polypeptide. In other embodiments a NKG2D inhibitor is a NKG2D expression inhibitor, meaning the inhibitor directly inhibits NKG2D by acting on a NKG2D nucleic acid to inhibit the expression of the NKG2D polypeptide. In some embodiments, the NKG2D receptor inhibitor directly binds NKG2D receptor on a cancer cell. In certain embodiments the NKG2D inhibitor inhibits formation of an NKG2D-DAP10 complex on a cancer cell. In other embodiments the NKG2D inhibitor directly binds an NKG2D-DAP10 complex on a cancer cell. In further embodiments, the NKG2D inhibitor inhibits NKG2D receptor expression in a tumor cell.

In certain embodiments, a patient is administered an effective amount of a composition comprising an NKG2D inhibitor. An "effective amount" refers to the amount of a therapeutic or prophylactic composition that achieves the intended goal. In some embodiments, the intended goal is to treat a hyperproliferative disease such as cancer or a tumor, which means an effective amount is that amount expected to achieve some prevention or treatment of the cancer or tumor. In some embodiments it refers to preventing or alleviating symptoms and/or cellular processes associated with a particular disease or condition, including but not limited to inhibition of cancer or tumor cell growth, metastasis, resistance to chemotherapy or radiotherapy, or recurrence. A hyperproliferative disease or condition refers to a disease or condition associated with uncontrolled cell growth.

Embodiments also concern methods comprising administering to a patient an NKG2D inhibitor because the patient has symptoms of cancer or a tumor, the patient is a risk for metastasis of a cancer or tumor, or the patient previously had cancer or a tumor and is at risk for recurrence, or the patient is in remission, but is at risk for no longer being in remission. In certain embodiments, methods include identifying a patient in need of a therapeutic or preventative agent for the treatment of a hyperproliferative disease, such as cancer or one or more tumors. In even further embodiments, the disease or condition does not include an autoimmune disease, including, but not limited to, rheumatoid arthritis.

In particular embodiments, the inhibitor is a polypeptide, nucleic acid, or small molecule. It is contemplated that NKG2D inhibitors may bind to or interfere with NKG2D protein so as to inhibit or reduce NKG2D activity or function. Alternatively, NKG2D inhibitors may bind to or interfere with NKG2D-encoding nucleic acids so as to inhibit NKG2D expression on a cancer cell.

In certain applications, the inhibitor is a polypeptide. Polypeptides include, but are not limited to, all or part of antibody that specifically recognizes or binds to NKG2D. The antibody may a polyclonal antibody or a monoclonal antibody. In particular embodiments, the antibody comprises a single chain variable fragment. It is contemplated that antibody inhibitors may be a neutralizing antibody. In additional embodiments, the antibody is a humanized antibody, chimeric antibody, or single chain antibody. In specific embodiments, the inhibitor is a human antibody that specifically binds to NKG2D. In particular embodiments, the human antibody is 16F16, 16F31, MS, or 21F2, as set forth in U.S. Pat. No. 7,879,985, which is hereby incorporated by reference. Alternatively, in further embodiments, an NKG2D inhibitor may comprise CDRs from 16F16, 16F31, MS, and/or 21F2. In specific embodiments, the human antibody is 16F16. In other embodiments, the human antibody is 16F31. In further embodiments, the human antibody is MS. In additional embodiments, the human antibody is 21F2. A combination comprising 1, 2, 3, or all 4 of human antibodies 16F16, 16F31, MS, and 21F2 is contemplated in methods and compositions described herein. In further embodiments, an antibody comprises the amino acid sequence of one or more of SEQ ID NO:25-64.

In certain aspects a polypeptide can comprise all or part of the heavy chain variable region and/or the light chain variable region of NKG2D specific antibodies. In a further aspect, a polypeptide can comprise an amino acid sequence that corresponds to a first, second, and/or third complementary determining regions (CDRs) from the light variable chain and/or heavy variable chain of an antibody, e.g., a NKG2D-specific antibody. Additionally an antibody or binding polypeptide may have a binding region comprising an amino acid sequence having, having at least, or having at most 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identity or homology (substitution with a conserved amino acid) (or any range derivable therein) with 1, 2, 3, 4, 5, or 6 CDR sequences discussed herein. In specific embodiments, an antibody having all or part of one or more CDRs disclosed herein has been humanized in non-CDR regions. In further embodiments, the CDR regions disclosed herein may be changed by 1, 2, 3, 4, 5, 6, 7 or 8 amino acids per CDR, which may be instead of or in addition to humanization. In some embodiments, a change may be a deletion or addition of 1, 2, or 3 amino acids, or it may be a substitution of any amino acid, which may or may not be with an amino acid that is a conserved an amino acid.

In some embodiments, an NKG2D binding polypeptide or antibody has one, two, three, four, five, six, or seven CDRs that have 40, 45, 50, 55, 60, 65, 70, 75, 80, 85, 90, 95, 96, 97, 98, 99, 100% identity with a consensus sequence identified for that CDR. It is contemplated that in some embodiments, an NKG2D binding polypeptide or antibody has an amino acid sequence corresponding to CDR1, CDR2, and CDR3 of a light chain variable region and a CDR1, CDR2, and CDR3 of a heavy chain variable region. As discussed herein the amino acid sequence corresponding to a CDR may have a percent identity or homology to a CDR discussed herein. In particular embodiments, the NKG2D binding polypeptide or antibody has a consensus sequence from a monoclonal antibody for CDR1, CDR2, and/or CDR3 of the light chain variable region. Alternatively or additionally, the NKG2D binding polypeptide or antibody has a consensus sequence from a monoclonal antibody for CDR1, CDR2, and/or CDR3 of a heavy chain variable region. It is further contemplated that a NKG2D binding polypeptide or antibody may have a mix of CDRs based on consensus sequence(s) and/or sequences with identity or homology to a particular CDR.

In other embodiments, a polypeptide or protein comprises 1, 2, 3, 4, 5, or 6 CDRs from the either or both of the light and heavy variable regions provided herein, and 1, 2, 3, 4, 5, or 6 CDRs may have 1, 2, and/or 3 amino acid changes with respect to these CDRs. In some embodiments, parts or all of the antibody sequence outside the variable region have been humanized. A protein may comprise one or more polypeptides. In some aspects, a protein may contain one or two polypeptides similar to a heavy chain polypeptide and/or 1 or 2 polypeptides similar to a light chain polypeptide. In further embodiments, a polypeptide may be a single chain antibody or other antibody discussed herein so long as it at least 70% sequence identity or homology to 1, 2, 3, 4, 5, or 6 CDRs of an antibody.

In yet further aspects, a polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of an NKG2D specific antibody, including, but not limited to antibody sequences provided in SEQ ID NOs: 25-64. For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 an NKG2D specific antibody as provided herein.

In some aspects, a polypeptide comprises additionally or alternatively, an amino acid sequence that is at least 60, 65, 70, 75, 80, 85, 90, 95, 96, 97, 98, 99, or 100% identical or homologous to the amino acid sequence of the variable region that is not a CDR sequence, i.e., the variable region framework.

In certain embodiments, the NKG2D inhibitor is an antibody that is an IgG antibody. In specific embodiments, an IgG antibody is an IgG1 antibody. An IgG1 antibody that may be used in some embodiments is an E4 antibody, as described in Steigerwald et al., *MAbs*, 1(2):115-127, 2009, which is hereby incorporated by reference.

In other embodiments, certain polypeptide inhibitors may instead inhibit NKG2D expression, for example, by inhibiting NKG2D transcription. In further embodiments the inhibitor is a nucleic acid. In certain embodiments, the nucleic acid is an siRNA, meaning the inhibitor is fully or partially complementary (has complementarity) to a NKG2D-encoding nucleic acid and inhibits NKG2D expression, or that it is fully or complementary to a DAP10 encoding nucleic acid and inhibits DAP10 expression. In certain embodiments, the siRNA is a single- or double-stranded nucleic acid with a contiguous sequence of at least 10 contiguous nucleotides of SEQ ID NO:1. Other examples of siRNAs are disclosed herein and may be used in embodiments.

In some embodiments, there are compositions comprising a nucleic acid molecule that contains a sequence that is capable of hybridizing under stringent conditions to a human NKG2D or human DAP10 mRNA, whose cDNA sequence is SEQ ID NO:1 (or SEQ ID NO:2, respectively). In certain embodiments, the nucleic acid is at least or at most 12, 13, 14, 15, 16, 17, 18, 19, 20, 21, 22, 23, 24, 25, 26, 27, 28, 29, 30, 31, 32, 33, 34, 35, 36, 37, 38, 39, 440, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125 nucleotides in length, or any range derivable therein. A nucleic acid molecule may be single-stranded or it may be double-stranded. As a double-stranded molecule, the nucleic acid molecule may include two separate strands or the molecule may be a hairpin in which the two strands are continuous with one another.

Moreover, in some embodiments, the nucleic acid molecule is or comprises RNA. In other embodiments, the nucleic acid molecule is or comprises DNA. In other embodiments, the nucleic acid molecule includes one or more nucleic acid analogs or modifications.

In some embodiments, a double-stranded molecule is blunt-ended on one end or at least one end. In other embodiments, a double-stranded nucleic acid molecule is blunt-ended on both ends. In specific embodiments, there may be an overhang on one end or both ends of a double-stranded nucleic acid molecule. The overhang at one end or both ends may be 1, 2, 3, 4, 5, 6, 7, 8, 9, 10 nucleotides or any range derivable therein. If on one end, it may be on the 5' end of the sense strand or the 3' end of the sense strand, or it may be on the 5' end of the antisense strand or on the 3' end of the antisense strand.

Embodiments may concern a nucleic acid molecule that has at least one strand that is 80, 81, 82, 83, 84, 85, 86, 87, 88, 89, 90, 91, 92, 93, 94, 95, 96, 97, 98, 99, or 100% identical (or any range derivable therein) to the complement of a contiguous region of SEQ ID NO:1 or SEQ ID NO:2. It is contemplated that such nucleic acids are capable of specifically hybridizing to the contiguous region of SEQ ID NO:1 so as to inhibit expression of NKG2D in a human cancer cell. It is contemplated that such nucleic acids are capable of specifically hybridizing to the contiguous region of SEQ ID NO:2 so as to inhibit expression of DAP10 in a human cancer cell. In the case of double-stranded nucleic acid molecules, it is further contemplated that there is also a strand that is 80, 81, 82, 83, 84, 85, 86, 87, 88, 89, 90, 91, 92, 93, 94, 95, 96, 97, 98, 99, or 100% identical (or any range derivable therein) to a contiguous region of SEQ ID NO:1 or SEQ ID NO:2. The contiguous regions of SEQ ID NO:1 or SEQ ID NO:2 may be a region that constitutes 12, 13, 14, 15, 16, 17, 18, 19, 20, 21, 22, 23, 24, 25, 26, 27, 28, 29, 30, 31, 32, 33, 34, 35, 36, 37, 38, 39, 440, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 contiguous nucleic acid residues of SEQ ID NO:1 or SEQ ID NO:2 (or any range derivable therein).

In specific embodiments, a nucleic acid molecule, whether single-stranded or double-stranded comprises a strand whose sequence is 80, 81, 82, 83, 84, 85, 86, 87, 88, 89, 90, 91, 92, 93, 94, 95, 96, 97, 98, 99, or 100% identical (or any range derivable therein) to all or part of SEQ ID NO:1, SEQ ID NO:2, SEQ ID NO:18, SEQ ID NO:19; SEQ ID NO:20, or SEQ ID No:21. With double-stranded nucleic acid molecules, one of the strands may have a sequence that is 80, 81, 82, 83, 84, 85, 86, 87, 88, 89, 90, 91, 92, 93, 94, 95, 96, 97, 98, 99, or 100% identical (or any range derivable therein) to a region of SEQ ID NO:1 or SEQ ID NO:2 that has, has at most, or has at least 12, 13, 14, 15, 16, 17, 18, 19, 20, 21, 22, 23, 24, 25, 26, 27, 28, 29, 30, 31, 32, 33, 34, 35, 36, 37, 38, 39, 440, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 contiguous nucleic acid residues from either sequence (or any range derivable therein).

It is specifically contemplated for any SEQ ID NO described above or herein that a corresponding RNA sequence may be used in embodiments instead of the DNA sequence.

In some compositions and some methods, there may be more than one NKG2D inhibitor or more than one type of NKG2D inhibitor. For example, in some embodiments, there is more than one NKG2D human antibody. In other embodiments, there is more than one nucleic acid molecules targeting more than one sequence region of NKG2D or DAP10. In some embodiments, there a combination of different nucleic acid molecules. In some embodiments, there is a combination of nucleic acid molecules that target SEQ ID NO:1 and/or SEQ ID NO:2.

In some embodiments, the dsRNA has a length of from 19 to 28 nucleotides. In certain embodiments, one or both strands is 12, 13, 14, 15, 16, 17, 18, 19, 20, 21, 22, 23, 24, 25, 26, 27, 28, 29, 30, 31, 32, 33, 34, 35, 36, 37, 38, 39, 440, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125 nucleotides in length, or any range derivable therein.

A nucleic acid molecule may have one strand that includes the DNA sequence (or corresponding RNA) as set forth in any of SEQ ID NO:19, SEQ ID NO:20, SEQ ID NO:21 or SEQ ID NO:21. In some embodiments, the subject is administered a DNA molecule that encodes a strand of a dsRNA molecule as set forth herein.

The term "stringent conditions" refers to washing conditions of about 0.5× to about 1×SSC at 65° C. In certain embodiments, the NKG2D encoding sequence hybridizes to a nucleic acid in a biological sample under "very stringent conditions," which refers to washing conditions of about 0.1×SSC to about 0.5×SSC at 65° C.

The dsRNA may optionally be comprised in a vector. Vectors for delivery of nucleic acid molecules are well known to those of ordinary skill in the art. For example, the vector may include a cell, a liposome, a lipid, or a virus. Nonlimiting examples of viral vectors include adenoviral vectors, retroviral vectors, and lentiviral vectors.

Other aspects concern methods of treating a subject with cancer that involve administering to a subject with cancer a pharmaceutically effective amount of a composition comprising an isolated nucleic acid molecule that inhibits the expression of NKG2D.

Some embodiments further involve administering chemotherapy, radiation therapy, immunotherapy or hormone therapy to the cancer patient. These other anti-cancer therapies may be given in conjunction with the NKG2D inhibitor or before or after such treatment. In some embodiments, methods concern giving the other anti-cancer therapy first. In other methods the other anti-cancer agent is given after the NKG2D inhibitor. In certain embodiments, the chemotherapeutic agent is given with 1, 2, 3, 4, 5, 6, 7, 8, 9, 10, 11, 12, 13, 14, 15, 16, 17, 18, 19, 20, 21, 22, 23, 24 hours and/or 1, 2, 3, 4, 5, 6, and/or 7 days before or within the time the nucleic acid molecule is administered to a subject. It is specifically contemplated that some embodiments exclude methods involving a subject who is given chemotherapy more than 1, 2, 3, 4, 5, 6, 7, 8, 9, 10, 11, 12 months or more prior to being given a nucleic acid molecule. Alternatively, in some embodiments, a patient who previously received one or more other anti-cancer therapies but has a recurrent cancer or a cancer deemed unsuccessfully treated by the anti-cancer therapy may be subject to treatment methods involving NKG2D inhibitors as described herein.

The dosage range of the NKG2D inhibitor set forth herein may range from 0.001 to 1000 mg/kg. In more particular embodiments, the dosage range is 0.01 to 100 mg/kg. In more particular embodiments the dosage range is 0.5 to 50 mg/kg. Administration may be by any method known to those of ordinary skill in the art, such as intravenously, intrathecally, intratumorally, by inhalation, orally, topically, subdurally, intraperitoneally, and so forth.

In some embodiments, an inhibitor is administered to the patient intravenously, intraarterially, intraperitoneally, intrapleurally, intratracheally, topically, intraperitoneally, subcutaneously, mucosally, intrapericardially, orally, topically, locally, by inhalation, by injection, by infusion, by continuous infusion, by localized perfusion bathing target cells directly, via a catheter, via aerosol, via nebulizer, and/or via a lavage. In certain cases, an NKG2D inhibitor is administered intratracheally or intravenously. In other embodiments, the NKG2D inhibitor is administered directly to a tissue or organ that has cancer or tumor cells.

It is contemplated that methods may be applied to any animal capable of developing cancer or tumors that involve cancer or tumor cells that express NKG2D. In particular embodiments, the subject is a mammal, including but not limited to humans. In certain embodiments, a patient is suspected of having cancer or a tumor. This may be based on the patient's symptoms, medical history, a biopsy, a pathology analysis, or the results of one or more tests. In most cases, a patient has already been diagnosed with cancer or a tumor when the patient is administered the NKG2D inhibitor. In other cases, the patient has not been diagnosed with a cancer or a tumor but the patient is at risk for that.

In certain embodiments the patient is administered the NKG2D inhibitor more than one time. Multi-dosages of the NKG2D inhibitor may be given to the patient.

An inhibitor may be formulated in a pharmaceutically acceptable composition. In certain embodiments, a preservative and/or stabilizer is included in the composition.

In certain embodiments, methods may involve obtaining or retrieving a biological sample, such as by doing a biopsy on a tumor.

Embodiments also concern pharmaceutical compositions that include a NKG2D inhibitor. The compositions may be formulated in a pharmaceutically acceptable composition. In certain embodiments, a preservative and/or stabilizer is included in the composition. Such compositions may be administered or prescribed to mammals, including humans.

Furthermore, in some embodiments methods may involve compositions containing about, at least about, or at most about 0.1, 0.2, 0.3, 0.4, 0.5, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 ng, μg or mg of a NKG2D inhibitor (or any range derivable therein), which may be in about, at least about, or at most about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 10, 11, 12, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μl or ml (or any range derivable therein). Moreover, such amounts may be administered to a subject as that much hyaluronan/kg body weight of the subject. For example, a subject may be administered an amount in the range of about 1 μg/kg and about 1 mg/kg. In certain embodiments, the amount given to a subject is about, at least about, or at most about 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0. 19.5, 20.0, 21, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 μg/kg or mg/kg, or any range derivable therein. These amounts may be prescribed on a per administration basis or on a daily basis (for example on a μg/kg body weight/day basis).

Such amounts can be administered daily, though other dosing regimens are contemplated. It is contemplated that compositions may be administered just a single time or multiple times. Similarly steps of methods may be performed a single time or multiple times, such as 2, 3, 4, 5, 6, 7, 8, 9, 10 or more (or any range derivable therein). In certain embodiments, a composition is administered 1, 2, 3, 4, 5, 6 or more times, or any range derivable therein. It is contemplated that a preventative or treatment regimen may involve multiple administrations over 1, 2, 3, 4, 5, 6, and/or 7 days or 1, 2, 3, 4, or 5 weeks, and/or 1, 2, 3, 4, 5, 6, 7, 8, 9, 10, 11, and/or 12 months, or any range derivable therein. Moreover, any such regimen may be repeated after a certain amount of time has passed or when symptoms of the disease or condition become noticeable or more severe.

In some embodiments, a method may further comprise administering an immunostimulatory compound to the patient. Other methods may involve obtaining cancer cells from the patient and determining if the cells express NKG2D. In still further embodiments methods may also involve determining the level of sMIC expression in cancer cells from the patient.

Other embodiments are discussed throughout this application. Any embodiment discussed with respect to one aspect applies to other aspects described herein as well and vice versa. The embodiments in the Example section are understood to be embodiments that are applicable to all aspects of described embodiments.

The terms "inhibiting" and "reducing" or any variation of these terms, when used in the claims and/or the specification includes any measurable decrease or complete inhibition to achieve a desired result. The terms "prevention" and "preventing" refer to the expectation that something can be kept from happening to some extent or that the severity, duration, or extent of the condition or disease can be alleviated or reduced. It is contemplated that the terms "treating" or "preventing" in the context of a condition or disease refers to any reduction or inhibition of the disease or condition. In specific embodiments, the disease or condition is a hyperproliferative disease or condition. In certain other cases, embodiments pertain to cancer or tumors. In specific embodiments, the cancer is breast, ovarian, prostate or colon cancer.

The use of the word "a" or "an" when used in conjunction with the term "comprising" in the claims and/or the specification may mean "one," but it is also consistent with the meaning of "one or more," "at least one," and "one or more than one."

It is contemplated that any embodiment discussed herein can be implemented with respect to any method or composition of the invention, and vice versa. Furthermore, compositions and kits of the invention can be used to achieve methods of the invention.

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A-G. Cancer cell expression of NKG2D-DAP10 and stimulation of PI3K-dependent AKT phosphorylation. (A) Micrographs of Ab stainings for NKG2D and MIC of breast and ovarian cancer tissue cryosections. Stainings for CD3 identify tumor-infiltrating T cells. (B) Stainings of normal breast, ovary, and prostate tissue sections for NKG2D. (C) Flow cytometry of freshly isolated breast (BT), ovarian (OT), prostate (PT), and colon (CT) cancer cells (gated for $EpCAM^+CD45^-$, see upper left dot plot for a representative example) for surface NKG2D and MIC. Numbers in dot plots indicate percentages of cells in quadrants. (D) Detection of mRNA for NKG2D, DAP10, and control GAPDH by RT-PCR in NKL NK cells and in BT, CT, OT, and PT cancer cells. Note that sample OT91 is essentially negative for NKG2D-DAP10. RNAs were prepared from sorted $EpCAM^+CD45^-$ cancer cell suspensions. Panels at right show minimal NKG2D-DAP10 expression in control breast, ovary, and skin tissue specimens non-depleted for $CD45^+$ cells. Numbers at left indicate cDNA amplicon sizes in bp. (E) NKG2D immunoprecipitations (IP) with bead-coupled mAb 5C6 and immunoblotting (IB) for NKG2D and DAP10 using cell lysates of control NKL cells ($1 \times 10^6$ cells) and $EpCAM^+CD45^-$ cancer cells ($3$-$5 \times 10^6$ cells) corresponding to those shown in (D). Panels at right show protein data from an additional breast cancer and matched non-affected tissue (NAT) control. Numbers at left indicate molecular masses (in kD) of NKG2D and DAP10. (F) Stimulation of purified $EpCAM^+CD45^-$ breast, ovarian, and prostate cancer cells by crosslinked anti-NKG2D mAb 1D11 results in detection of P-AKT(S473) on total cell lysate immunoblots. P-AKT was not detected in ovarian cancer cells ($OT34^-$) sorted for absence of NKG2D. Exposure to insulin provides for positive control activation except with the non-responsive prostate cancer cells. The PI3K inhibitor wortmannin (Wort) inhibits AKT phosphorylation. DMSO is added as solvent control. (G) Detection of P-AKT (S473) after stimulation of purified breast and ovarian cancer cells with crosslinked anti-NKG2D mAb 5C6 $F(ab')_2$ fragments. Ig lanes in (F) and (G) represent cells exposed to primary mouse control IgG and secondary goat anti-mouse $F(ab')_2$.

FIG. 2A-B. PI3K-dependent AKT phosphorylation correlates with minimal NKG2D-DAP10 expression in tumor lines. (A) Immunoblot detection of P-AKT(S473) in lysates of desensitized MCF-7, BT-20, MDA-MB-453, HTB-78, DLD-1, and AGS but not of MDA-MB-231, PC3 and A375 cells after mAb 1D11 or mAb 5C6 $F(ab')_2$ crosslinking. Transfection of NKG2D-DAP10 restores AKT phosphorylation in A375-TF cells. Insulin provides for positive control activation. Ig control lanes represent cells exposed to mouse IgG and secondary goat anti-mouse $F(ab')_2$. DMSO is added as solvent control. As with the cancer cell suspensions, AKT phosphorylation is sensitive to wortmannin (wort). (B) AKT phosphorylation correlates with the detection of small amounts of NKG2D-DAP10 protein complexes by immunoprecipitation with bead-coupled anti-NKG2D mAb 5C6 from lysates of each $5 \times 10^7$ cells ($2 \times 10^7$ BT-20 and $5 \times 10^6$ A375-TF cells) and sequential immunoblot probing for NKG2D and DAP10.

FIG. 8A-E. Induction of an EMT-like phenotype by above-threshold expression of NKG2D-DAP10. Induction of an EMT-like phenotype by NKG2D-DAP10. (A) Phase contrast microscopy shows transition from epithelial to fibroblast-like shapes of MCF-7-TF versus mock-transfected control, and phenotype reversion by NKG2D RNAi. By IF microscopy, expression of NKG2D-DAP10 is associated with reduced E-cadherin and gain of N-cadherin and vimentin. (B) Immunoblot of E-cadherin, N-cadherin, and vimentin. (C) Induction of SNAI1 and Twist mRNAs in MCF-7-TF, MCF-10A-TF, and SUM149PT-TF cells shown by RT-PCR. (D) Representative data showing increased in vitro migration and invasion by MCF-7-TF versus negative control and MCF-7-TF-NKG2D RNAi cells. (E) Flow cytometry of NKG2D$^+$CD45$^-$ ovarian cancer cells (specimens OT04 and OT18) for E-cadherin and N-cadherin. Numbers in red circles indicate proportions (in %) of E-cadherin$^-$/N-cadherin$^+$ cells among NKG2D$^+$ cancer cells.

FIG. 9A-B. Stimulation of survival by NKG2D. (A) Percentages of apoptotic (Annexin V$^+$/7-AAD$^-$) cells were much lower among MCF-7-TF as compared to control cells after 72 hours of serum starvation. (B) Increased immunoblot detection of Bcl-2 in MCF-7-TF cells.

FIG. 10. Stimulation of Cellular Migration Through Porous Filters and Invasion of Reconstituted Basement Membranes in Matrigel Assay. Migratory and invasive activities are substantially increased with MCF-7-TF cells expressing above-threshold NKG2D-DAO10 as compared to mock transfectants. These activities are suppressed by RNAi targeting of NKG2D.

FIG. 13A-D. NKG2D promotes local invasion, intravasation and distant metastasis formation. A-C, Images are derived from tumors harvested at week 8 post orthotopic transplantation. MCF-7 mock and -TF tumor cells are identified by immunohistochemical detection of human pan-cytokeratin using the AE1/AE3 antibody. A, In contrast to non-invasive control tumors confined within fibrotic capsules, MCF-7-TF tumors display irregular strands of tumor tissue dissociating from the primary tumor mass and invading adjacent stroma. B, MCF-7-TF tumors display vascular invasion. Small clusters of AE1/AE3 positive cells are localized within an intratumoral vessel identified by staining for the MECA-32 mouse endothelial cell-specific marker. Control vessels adjacent to MCF-7 mock tumors contain erythrocytes but no AE1/AE3 positive cells. C, Serial Hematoxilin and Eosin-(H&E) and AE1/AE3-stained lung section with clusters of metastatic cells within black squares. D, Bioluminescence evidence of macro metastasis in lungs dissected from MCF-7-TF tumor but not control-tumor bearing mice.

DETAILED DESCRIPTION OF THE INVENTION

Figure 1C:
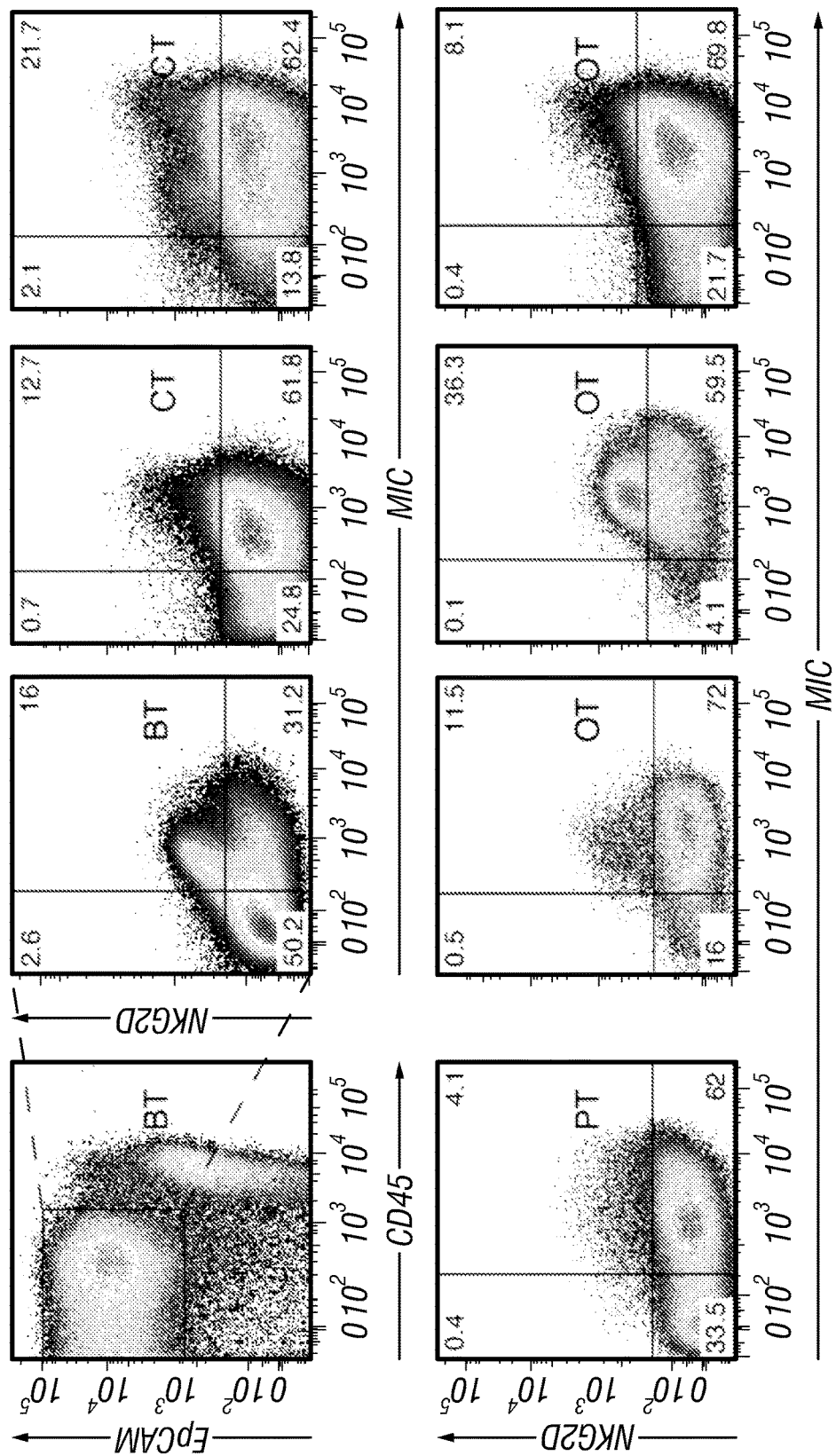

Embodiments concern methods and compositions involving inhibition of NKG2D engagement with its natural ligand.

NKG2D and DAP10

Tumor immune surveillance is mediated by the NKG2D lymphocyte receptor, which stimulates natural killer (NK) and CD8 T cell responses against cancer cells expressing its ligands. With advanced human cancers, however, persistent NKG2D ligand expression favors tumor progression, which has been ascribed to ligand-induced immune evasion. In a surprising conceptual twist, the Examples show that cancer cells themselves express NKG2D and may thus exploit the presence of its ligands for self stimulation of tumor growth and malignant progression. There is one precedent for co-option of a stimulatory lymphocyte receptor by cancers although they do express chemokine receptors such as CXCR4 and CCR7, and Fas (CD95), which instead of tumor cell death appears to promote tumor growth (Mani et al., 2008; Morel et al., 2008). While not being bound to theory, the inventors have determined that contrary to previous ideas about the role of NKG2D only in immune surveillance, NKG2D mediates promotion of tumor growth concurrent with immune surveillance failure at advanced tumor stages.

A. Diseases and Conditions

In certain embodiments, compounds and methods may be used to treat a wide variety of cancerous states including, for example, melanoma, non-small cell lung, small cell lung, lung, hepatocarcinoma, retinoblastoma, astrocytoma, glioblastoma, leukemia, blood, brain, skin, eye, tongue, gum, neuroblastoma, head, neck, breast, pancreatic, renal, bone, testicular, ovarian, mesothelioma, cervical, gastrointestinal, lymphoma, colon, and/or bladder. The cancer may comprise a tumor made of cancer cells. These cancerous states may include cells that are cancerous, pre-cancerous, and/or malignant.

In yet another embodiment, the treatment of a wide variety of cancerous states is an embodiment. For example, melanoma, non-small cell lung, small-cell lung, lung, hepatocarcinoma, retinoblastoma, astrocytoma, glioblastoma, leukemia, neuroblastoma, head, neck, breast, pancreatic, prostate, renal, bone, testicular, ovarian, mesothelioma, cervical, gastrointestinal, lymphoma, brain, colon or bladder. In still more preferred embodiments said angiogenesis-related diseases is rheumatoid arthritis, inflammatory bowel disease, osteoarthritis, leiomyomas, ademonas, lipomas, hemangiomas, fibromas, vascular occlusion, restenosis, atherosclerosis, pre-neoplastic lesions, carcinoma in situ, oral hairy leukoplakia or psoriasis may be the subject of treatment. In particular embodiments, the cancer involves a tumor, which may or may not be resectable. Moreover, the cancer may involve metastatic tumor(s) or a tumor possibly capable of metastasis. In further embodiments, the tumor is considered an advanced tumor, which refers to advanced or late-stage cancer.

Cancer cells that may be treated by methods and compositions also include any cells expressing NKG2D from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma;

chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In specific embodiments, the patient has breast, ovarian, prostate or colon cancer.

The phrases "treating cancer" and "treatment of cancer" mean to decrease, reduce, or inhibit the replication of cancer cells, decrease, reduce or inhibit the spread (formation of metastases) of cancer, decrease tumor size, decrease the number of tumors (i.e. reduce tumor burden), lessen or reduce the number of cancerous cells in the body, prevent recurrence of cancer after surgical removal or other anticancer therapies, or ameliorate or alleviate the symptoms of the disease caused by the cancer.

The term "anti-tumor activity" means a reduction in the rate of cell proliferation and hence a decline in growth rate of abnormal cells that arises during therapy. Anti-tumor activity also encompasses a reduction in tumor size. Such activity can be assessed using accepted animal models, such as the Namalwa and Daudi xenograft models of human B-cell lymphoma. See, e.g., Hudson et al., Leukemia 12:2029-2033 (1998) for a description of these animal models.

The term "tumor" means any neoplastic cell growth or proliferation, whether malignant or benign, whether in liquid or solid form and all pre-cancerous and cancerous cells and tissues.

The terms "cancer" and "cancerous" refer to or describe the physiological condition in mammals that is typically characterized by unregulated cell growth. A cancer refers to any of a number of conditions caused by the abnormal, uncontrolled growth of cells. Cells capable of causing cancer, called "cancer cells," possess a number of characteristic properties such as uncontrolled proliferation, immortality, metastatic potential, rapid growth and proliferation rate, and certain typical morphological features. Often, cancer cells will be in the form of a tumor, but such cells may also exist alone or may be a non-tumorgenic cancer cell, such as a leukemia cell. A cancer can be detected in any of a number of ways, including, but not limited to, detecting the presence of a tumor or tumors (e.g., by clinical or radiological means), examining cells within a tumor or from another biological sample (e.g., from a tissue biopsy), measuring blood markers indicative of cancer (e.g., CA125, PAP, PSA, CEA, AFP, HCG, CA 19-9, CA 15-3, CA 27-29, LDH, NSE, and others) and detecting a genotype indicative of a cancer (e.g., TP53, ATM, etc). However, a negative result in one or more of the above detection methods does not necessarily indicate the absence of cancer, e.g., a patient who has exhibited a complete response to a cancer treatment may still have a cancer, as evidenced by a subsequent relapse. Examples of cancer include, but are not limited to, carcinoma, lymphoma, blastoma, sarcoma, and leukemia.

The term "anti-cancer agent" means any agent that can be used to treat a cell proliferative disorder such as cancer, including cytotoxic agents, chemotherapeutic agents, radiotherapy and radiotherapeutic agents, targeted anti-cancer agents, and immunotherapeutic agents.

B. Nucleic Acids

Embodiments concern polynucleotides or nucleic acid molecules relating to NKG2D sequences or DAP10 sequences in therapeutic and preventative applications. In certain embodiments, nucleic acid molecules serve as a NKG2D inhibitor for the prevention or treatment of cancer. In certain embodiments there are sequences or a sequence that hybridizes to a NKG2D-encoding sequence (such as an NKG2D mRNA or its DNA equivalent) under stringent or highly stringent hybridization conditions. Nucleic acids or polynucleotides may be DNA or RNA, and they may be oligonucleotides (100 residues or fewer) in certain embodiments. Moreover, they may be recombinantly produced or synthetically produced.

These polynucleotides or nucleic acid molecules may be isolatable and/or purifiable from cells or they may be synthetically produced. In some embodiments, an NKG2D-encoding nucleic acid is the target of a nucleic acid NKG2d receptor inhibitor, such as a ribozyme or siRNA that reduces the level of NKG2D expression.

As used in this application, the term "polynucleotide" refers to a nucleic acid molecule, RNA or DNA, that has been isolated free of total genomic nucleic acid. Therefore, a "polynucleotide encoding NKG2D" refers to a nucleic acid sequence (RNA or DNA) that contains NKG2D coding sequences, yet may be isolated away from, or purified and free of, total genomic DNA and proteins.

The term "cDNA" is intended to refer to DNA prepared using RNA as a template. The advantage of using a cDNA, as opposed to genomic DNA or an RNA transcript is stability and the ability to manipulate the sequence using recombinant DNA technology (See Sambrook, 2001; Ausubel, 1996). There may be times when the full or partial genomic sequence is some. Alternatively, cDNAs may be advantageous because it represents coding regions of a polypeptide and eliminates introns and other regulatory regions. In certain embodiments, nucleic acids are complementary or identical to human cDNA encoding sequences, such as a human NKG2D sequence or a human DAP10 sequence.

The term "gene" is used for simplicity to refer to a functional protein, polypeptide, or peptide-encoding nucleic acid unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule hybridizing to a human NKG2D or human DAP10 gene may comprise a contiguous nucleic acid sequence of the following lengths or at least the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more (or any range derivable therein) nucleotides, nucleosides, or base pairs of the human NKG2D sequence or the human DAP10 sequence. Such lengths of sequences may be identical or complementary to SEQ ID NO:1 or SEQ ID NO:2.

Accordingly, sequences that have or have at least or at most 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, and any range derivable therein, of nucleic acids that are identical or complementary to a nucleic acid sequence of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, or 5000 contiguous bases (or any range derivable therein) of SEQ ID NO:1, SEQ ID NO:2 or SEQ ID NOs:19-22 are contemplated as embodiments. They may be used as NKG2D inhibitors because they inhibit expression of NKG2D receptor or DAP10 as NKG2D siRNAs or DAP10 siRNAs (or DNA equivalents thereof).

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

"Polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after synthesis, such as by conjugation with a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, alpha-anomeric sugars, epimeric sugars such as arabinose, xyloses or lyxoses, pyranose sugars, furanose sugars, sedoheptuloses, acyclic analogs and a basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a phage vector. Another type of vector is a viral vector, wherein additional DNA segments may be ligated into the viral genome (such as an adenoviral vector, a lentiviral vector, etc.). Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors").

The term "sequence identity" (or "sequence similarity") is herein defined as a relationship between two or more nucleic acid (polynucleotide) or amino acid (polypeptide) sequences, as determined by comparing the sequences. Usually, sequence identities or similarities are compared, typically over the whole length of the sequences compared. However, sequences may be compared over shorter comparison windows. In the art, "identity" also means the degree of relatedness between nucleic acid or amino acid sequences, as the case may be, as determined by the match between strings of such sequences.

In particular embodiments, there are isolated nucleic acid segments and recombinant vectors incorporating DNA sequences that encode NKG2D inhibitors, such as NKG2D siRNAs, DAP10 siRNAs, ribozymes and NKG2D receptor blockade antibodies and other NKG2D or DAP10 binding proteins or proteins that inhibit the activity of NKG2D as a receptor.

In some embodiments, a nucleic acid may encode an antisense construct. Antisense methodology takes advantage of the fact that nucleic acids tend to pair with "complementary sequences." By complementary, it is meant that polynucleotides are those which are capable of base-pairing according to the standard Watson-Crick complementarity rules. Inclusion of less common bases such as inosine, 5-methylcytosine, 6-methyladenine, hypoxanthine and others in hybridizing sequences does not interfere with pairing.

Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

In certain embodiments, the nucleic acid encodes an interfering RNA or siRNA. RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery, 1999; Montgomery et al., 1998; Sharp and Zamore, 2000; Tabara et al., 1999). Activation of these mechanisms targets mature, dsRNA-complementary mRNA for destruction. Advantages of RNAi include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, C. elegans, Trypanasoma, Drosophila, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

siRNAs are designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; or through an in vitro system derived from S2 cells. Chemical synthesis proceeds by making two single stranded RNA-oligomers followed by the annealing of the two single stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy)thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

In some embodiments, there is an siRNA that is capable of triggering RNA interference, a process by which a particular RNA sequence is destroyed. siRNA are dsRNA molecules that are 100 bases or fewer in length (or have 100 basepairs or fewer in its complementarity region). In some cases, it has a 2 nucleotide 3' overhang and a 5' phosphate. The particular RNA sequence is targeted as a result of the complementarity between the dsRNA and the particular RNA sequence. It will be understood that dsRNA or siRNA can effect at least a 20, 30, 40, 50, 60, 70, 80, 90 percent or more reduction of expression of a targeted RNA in a cell. dsRNA (the term "dsRNA" will be understood to include "siRNA") is distinct and distinguishable from antisense and ribozyme molecules by virtue of the ability to trigger RNAi. Structurally, dsRNA molecules for RNAi differ from antisense and ribozyme molecules in that dsRNA has at least one region of complementarity within the RNA molecule. The complementary (also referred to as "complementarity") region comprises at least or at most 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, or 1000 contiguous bases, or any range derivable therein, to sequences (or their complements) disclosed herein. In some embodiments, the sequence is any of SEQ ID NO:1 or SEQ ID NOs:3-9. In some embodiments, long dsRNA are employed in which "long" refers to dsRNA that are 1000 bases or longer (or 1000 basepairs or longer in complementarity region). The term "dsRNA" includes "long dsRNA" and "intermediate dsRNA" unless otherwise indicated. In some embodiments, dsRNA can exclude the use of siRNA, long dsRNA, and/or "intermediate" dsRNA (lengths of 100 to 1000 bases or basepairs in complementarity region). It is specifically contemplated that a dsRNA may be a molecule comprising two separate RNA strands in which one strand has at least one region complementary to a region on the other strand. Alternatively, a dsRNA includes a molecule that is single stranded yet has at least one complementarity region as described above (see Sui et al., 2002 and Brummelkamp et al., 2002 in which a single strand with a hairpin loop is used as a dsRNA for RNAi). For convenience, lengths of dsRNA may be referred to in terms of bases, which simply refers to the length of a single strand or in terms of basepairs, which refers to the length of the complementarity region. It is specifically contemplated that embodiments discussed herein with respect to a dsRNA comprised of two strands are contemplated for use with respect to a dsRNA comprising a single strand, and vice versa. In a two-stranded dsRNA molecule, the strand that has a sequence that is complementary to the targeted mRNA is referred to as the "antisense strand" and the strand with a sequence identical to the targeted mRNA is referred to as the "sense strand." Similarly, with a dsRNA comprising only a single strand, it is contemplated that the "antisense region" has the sequence complementary to the targeted mRNA, while the "sense region" has the sequence identical to the targeted mRNA. Furthermore, it will be understood that sense and antisense region, like sense and antisense strands, are complementary (i.e., can specifically hybridize) to each other.

The single RNA strand or two complementary double strands of a dsRNA molecule may be of at least or at most the following lengths: 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1100, 1200, 1300, 1400, 1500, 1600, 1700, 1800, 1900, 2000, 2100, 2200, 2300, 2400, 2500, 2600, 2700, 2800, 2900, 3000, 31, 3200, 3300, 3400, 3500, 3600, 3700, 3800, 3900, 4000, 4100, 4200, 4300, 4400, 4500, 4600, 4700, 4800, 4900, 5000, 6000, 7000, 8000, 9000, 10000 or more (including the full-length of a particular's gene's mRNA without the poly-A tail) bases or basepairs. If the dsRNA is composed of two separate strands, the two strands may be the same length or different lengths. If the dsRNA is a single strand, in addition to the complementarity region, the strand may have 1, 2, 3, 4, 5, 6, 7, 8, 9, 10, 11, 12, 13, 14, 15, 16, 17, 18, 19, 20, 21, 22, 23, 24, 25, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more bases on either or both ends (5' and/or 3') or as forming a hairpin loop between the complementarity regions.

In some embodiments, the strand or strands of dsRNA are 100 bases (or basepairs) or less, in which case they may also be referred to as "siRNA." In specific embodiments the strand or strands of the dsRNA are less than 70 bases in length. With respect to those embodiments, the dsRNA strand or strands may be from 5-70, 10-65, 20-60, 30-55, 40-50 bases or basepairs in length. A dsRNA that has a complementarity region equal to or less than 30 basepairs (such as a single stranded hairpin RNA in which the stem or complementary portion is less than or equal to 30 basepairs) or one in which the strands are 30 bases or fewer in length is specifically contemplated, as such molecules evade a mammalian's cell antiviral response. Thus, a hairpin dsRNA (one strand) may be 70 or fewer bases in length with a complementary region of 30 basepairs or fewer. In some cases, a dsRNA may be processed in the cell into siRNA.

Chemically synthesized siRNAs are found to work optimally when they are in cell culture at concentrations of 25-100 nM, but concentrations of about 100 nM have achieved effective suppression of expression in mammalian cells. siRNAs have been most effective in mammalian cell culture at about 100 nM. In several instances, however, lower concentrations of chemically synthesized siRNA have been used (Caplen et al., 2000; Elbashir et al., 2001).

PCT publications WO 99/32619 and WO 01/68836 suggest that RNA for use in siRNA may be chemically or enzymatically synthesized. Both of these texts are incorporated herein in their entirety by reference. The contemplated constructs provide templates that produce RNAs that contain nucleotide sequences identical to a portion of the target gene. Typically the length of identical sequences provided is at least 25 bases, and may be as many as 400 or more bases in length. Longer dsRNAs may be digested to 21-25mer lengths with endogenous nuclease complex that converts long dsRNAs to siRNAs in vivo. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. U.S. Pat. No. 5,795,715 reports the simultaneous transcription of two complementary DNA sequence strands in a single reaction mixture, wherein the two transcripts are immediately hybridized.

In an embodiment, the compositions comprise one or more isolated or purified nucleic acid molecules and methods of utilizing these nucleic acid molecules to reduce the expression of NKG2D or DAP10 in a cell. As used herein, the term "nucleic acid molecule" can include DNA molecules; RNA molecules; analogs of a DNA or RNA molecule generated using nucleotide analogs; derivatives thereof or combinations thereof. A nucleic acid molecule may be single-stranded or double-stranded, and the strandedness will depend upon its intended use. Fragments or portions of the disclosed nucleic acid molecules are also encompassed by the present disclosure. By "fragment" or "portion" is meant less than full length of the nucleotide sequence. As used herein, an "isolated" or "purified" nucleic acid molecule is a nucleic acid molecule that is separated from other nucleic acid molecules that are usually associated with the isolated nucleic acid molecule. Thus, an isolated nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Alternatively, the "isolated" or "purified" nucleic acid molecule may be substantially free of other cellular material or culture medium when produced by recombinant techniques or substantially free of chemical precursors or other chemicals when chemically synthesized. Herein substantially free refers to the level of other components being present in amounts that do not adversely affect the properties of the NKG2D or DAP10 reducing compositions and/or the organisms to which the compositions are introduced. For example, the nucleic acid molecules may be greater than about 70% pure, alternatively greater than about 75%, 80%, 85%, 90%, or 95% pure. Such an isolated nucleic acid molecule is generally introduced into a vector (e.g., a cloning vector, or an expression vector, or an expression construct) for convenience of manipulation or to generate a fusion nucleic acid molecule as will be described in more detail later herein. In addition, an isolated nucleic acid molecule can include an engineered nucleic acid molecule such as a recombinant or a synthetic nucleic acid molecule.

A nucleic acid molecule may be used to regulate the expression of one or more cellular proteins. For example, the nucleic acid molecule of this disclosure may function to reduce the expression of one or more NKG2D or DAP10 transcripts or polypeptides. In an embodiment, the nucleic acid molecules comprise RNA and introduction of the RNA into a cell results in post transcriptional silencing of at least one RNA transcript. The present disclosure provides for such RNA molecules, the DNA molecules encoding such RNA molecules, the polypeptide encoded by such nucleic acid molecules, antibodies raised to said polypeptides; or combinations thereof. The RNA molecules of this disclosure can be used in a variety of forms; nonlimiting examples of which include antisense RNAi and shRNA.

The disclosed methodologies utilize the RNA interference (RNAi) mechanism to reduce the expression of one or more RNA transcripts. The term "RNA interference or silencing" is broadly defined to include all posttranscriptional and transcriptional mechanisms of RNA mediated inhibition of gene expression, such as those described in P. D. Zamore Science 296, 1265 (2002) which is incorporated by reference herein in its entirety. The discussion that follows focuses on the proposed mechanism of RNA interference mediated by short interfering RNA as is presently known, and is not meant to be limiting and is not an admission of prior art.

RNAi is a conserved biological response that is present in many, if not most, eukaryotic organisms. RNAi results in transcript silencing that is both systemic and heritable, permitting the consequences of altering gene expression to be examined throughout the development and life of an animal.

In the RNAi process, long double-stranded RNA molecules (dsRNA) can induce sequence-specific silencing of gene expression in primitive and multicellular organisms. These long dsRNAs are processed by a ribonuclease called Dicer into 21 to 23 nucleotide (nt) guide RNA duplexes termed short interfering RNA (siRNA). The siRNA is subsequently used by an RNA-induced silencing complex (RISC), a protein-RNA effector nuclease complex that uses siRNA as a template to recognize and cleave RNA targets with similar nucleotide sequences. The composition of RISC is not completely defined, but includes argonaute family proteins. The RISC unwinds siRNAs and associates stably with the (antisense) strand that is complementary to the target mRNA. Depending on the degree of homology between a siRNA and its target mRNA, siRNA-RISC complexes inhibit gene function by two distinct pathways. Most siRNAs pair imperfectly with their targets and silence gene expression by translational repression. This RNAi mechanism appears to operate most efficiently when multiple siRNA-binding sites are present in the 3'-untranslated region of the target mRNAs. In some other cases, siRNAs exhibit perfect sequence identity with the target mRNA and inhibit gene function by triggering mRNA degradation. The reduction in transcript level results in lowered levels of the target protein, resulting in phenotypic changes.

While siRNA has been shown to be effective for short-term gene inhibition in certain transformed mammalian cell lines, there may be drawbacks associated with its use in primary cell cultures or for stable transcript knockdown because their suppressive effects are by definition of limited duration. Short hairpin RNAs (shRNA), consisting of short duplex structures, in contrast to siRNAs have been proved as effective triggers of stable gene silencing in plants, in *C. elegans*, and in *Drosophila*. These synthetic forms of RNA may be expressed from pol II or pol III promoters and the hairpin structure is recognized and cleaved by Dicer to form siRNA that is subsequently taken up by RISC for silencing of the target gene.

In some embodiments, the compositions of this disclosure may comprise one nucleic acid molecule that is able to reduce the expression of NKG2D and/or DAP10. Alternatively, one nucleic acid molecule of the type described herein may exhibit cross reactivity such that it is able to reduce the expression of NKG2D or DAP10 from differing species.

The compositions of this disclosure comprise one or more nucleic acid molecules. In an embodiment, the nucleic acid molecule comprises a double stranded ribonucleic acid (dsRNA) molecule that inhibits the expression of a target gene wherein the dsRNA molecule comprises two strands of nucleotides wherein the first strand is substantially identical to the nucleotide sequence of SEQ ID NOs: 3, 5, 7, 9, or 11 and wherein the second strand is substantially complementary to the first strand. Herein substantially identical refers to greater than about 50% homology while substantially complementary refers to a complementarity sufficient to permit the annealing of the second strand to the first strand under biological conditions such as within the cytoplasm of a eukaryotic cell.

In an embodiment, the first strand is greater than about 55% identical, alternatively greater than about 60%, 65%, 70%, 75%, 80%, 90%, 95% identical to a complementary region of SEQ ID NO:1 or SEQ ID NO:2. The first strand may be of sufficient length such that it is processed by Dicer to produce an siRNA. Either strand may serve as a substrate for Dicer.

The length of each strand generally is from about 19 to about 25 nt in length (e.g., 19, 20, 21, 22, 23, 24, or 25 nucleotides). In some embodiments, the length of each strand is from about 19 to about 28 nucleotides in length. In one embodiment, the length of the sequence in the first strand is identical to the length of the sequence in the second strand and the dsRNA formed is blunt ended. In an alternative embodiment, the ends of the dsRNA formed has overhangs.

In an embodiment, an dsRNA for use in reducing the level of expression of a human NKG2D or DAP10 comprises a first strand which includes the RNA equivalent of the sequence and of SEQ ID NO:19-22. In an embodiment, the complementary first and second strands of the dsRNA molecule are the "stem" of a hairpin structure.

The two dsRNA strands can be joined by a binding moiety, which can form the "loop" in the hairpin structure of shRNA. In an embodiment the binding moiety comprises a polynucleotide linker which can vary in length. In some embodiments, the binding moiety can be 5, 6, 7, 8, 9, 10, 11, 12 or 13 nucleotides in length, alternatively the binding moiety is 9 nucleotides in length.

Nucleic acid molecules (e.g., dsRNA, shRNA) as described herein can be obtained using techniques known to one of ordinary skill in the art such as for example, recombinant nucleic acid technology; chemical synthesis, either as a single nucleic acid molecule or as a series of oligonucleotides; mutagenesis using common molecular cloning techniques (e.g., site-directed mutagenesis); and the polymerase chain reaction (PCR). General PCR techniques are described, for example in PCR Primer: A Laboratory Manual, Dieffenbach & Dveksler, Eds., Cold Spring Harbor Laboratory Press, 1995 which is incorporated by reference herein in its entirety. Possible mutations include, without limitation, deletions, insertions, substitutions, and combinations thereof. Additionally, suitable molecular biology techniques may be employed for isolation of these molecules such as for example and without limitation restriction enzyme digestion and ligation.

As is known in the art, a nucleoside is a base-sugar combination. The base (or nucleobase) portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. In addition, linear compounds may have internal nucleobase complementarity and may therefore fold in a manner as to produce a fully or partially double-stranded structure. Within the unmodified oligonucleotide structure, the phosphate groups are commonly referred to as forming the internucleoside linkages of the oligonucleotide. The unmodified internucleoside linkage of RNA and DNA is a 3' to 5' phosphodiester linkage.

In the context of this disclosure, the term "unmodified oligonucleotide" refers generally to an oligomer or polymer of ribonucleic acid (RNA) or deoxyribonucleic acid (DNA). In some embodiments a nucleic acid molecule is an unmodified oligonucleotide. This term includes oligonucleotides composed of naturally occurring nucleobases, sugars and covalent internucleoside linkages. The term "oligonucleotide analog" refers to oligonucleotides that have one or more non-naturally occurring portions which function in a similar manner to oligonucleotides. Such non-naturally occurring oligonucleotides are often selected over naturally occurring forms because of desirable properties such as, for example, enhanced cellular uptake, enhanced affinity for other oligonucleotides or nucleic acid targets and increased stability in the presence of nucleases. The term "oligonucleotide" can be used to refer to unmodified oligonucleotides or oligonucleotide analogs.

Specific examples of nucleic acid molecules include nucleic acid molecules containing modified, i.e., non-naturally occurring internucleoside linkages. Such non-naturally internucleoside linkages are often selected over naturally occurring forms because of desirable properties such as, for example, enhanced cellular uptake, enhanced affinity for other oligonucleotides or nucleic acid targets and increased stability in the presence of nucleases.

Nucleic acid molecules can have one or more modified internucleoside linkages. As defined in this specification, oligonucleotides having modified internucleoside linkages include internucleoside linkages that retain a phosphorus atom and internucleoside linkages that do not have a phosphorus atom. For the purposes of this specification, and as sometimes referenced in the art, modified oligonucleotides that do not have a phosphorus atom in their internucleoside backbone can also be considered to be oligonucleosides.

One suitable phosphorus-containing modified internucleoside linkage is the phosphorothioate internucleoside linkage. A number of other modified oligonucleotide backbones (internucleoside linkages) are known in the art and may be useful in the context of this embodiment.

Representative U.S. patents that teach the preparation of phosphorus-containing internucleoside linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 5,625,050, 5,489,677, and 5,602,240 each of which is herein incorporated by reference.

Modified oligonucleotide backbones (internucleoside linkages) that do not include a phosphorus atom therein have internucleoside linkages that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having amide backbones; and others, including those having mixed N, O, S and CH2 component parts.

Representative U.S. patents that teach the preparation of the above non-phosphorous-containing oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Oligomeric compounds can also include oligonucleotide mimetics. The term mimetic as it is applied to oligonucleotides is intended to include oligomeric compounds wherein only the furanose ring or both the furanose ring and the internucleotide linkage are replaced with novel groups, replacement of only the furanose ring with for example a morpholino ring, is also referred to in the art as being a sugar surrogate. The heterocyclic base moiety or a modified heterocyclic base moiety is maintained for hybridization with an appropriate target nucleic acid.

Oligonucleotide mimetics can include oligomeric compounds such as peptide nucleic acids (PNA) and cyclohexenyl nucleic acids (known as CeNA, see Wang et al., J. Am. Chem. Soc., 2000, 122, 8595-8602) Representative U.S. patents that teach the preparation of oligonucleotide mimetics include, but are not limited to, U.S. Pat. Nos. 5,539,082; 5,714,331; and 5,719,262, each of which is herein incorporated by reference. Another class of oligonucleotide mimetic is referred to as phosphonomonoester nucleic acid and incorporates a phosphorus group in the backbone. This class of olignucleotide mimetic is reported to have useful physical and biological and pharmacological properties in the areas of inhibiting gene expression (antisense oligonucleotides, ribozymes, sense oligonucleotides and triplex-forming oligonucleotides), as probes for the detection of nucleic acids and as auxiliaries for use in molecular biology. Another oligonucleotide mimetic has been reported wherein the furanosyl ring has been replaced by a cyclobutyl moiety.

Nucleic acid molecules can also contain one or more modified or substituted sugar moieties. The base moieties are maintained for hybridization with an appropriate nucleic acid target compound. Sugar modifications can impart nuclease stability, binding affinity or some other beneficial biological property to the oligomeric compounds.

Representative modified sugars include carbocyclic or acyclic sugars, sugars having substituent groups at one or more of their 2', 3' or 4' positions, sugars having substituents in place of one or more hydrogen atoms of the sugar, and sugars having a linkage between any two other atoms in the sugar. A large number of sugar modifications are known in the art, sugars modified at the 2' position and those which have a bridge between any 2 atoms of the sugar (such that the sugar is bicyclic) are particularly useful in this embodiment. Examples of sugar modifications useful in this embodiment include, but are not limited to compounds comprising a sugar substituent group selected from: OH; F; O-, S-, or N-alkyl; or O-alkyl-O-alkyl, wherein the alkyl, alkenyl and alkynyl may be substituted or unsubstituted C1 to C10 alkyl or C2 to C10 alkenyl and alkynyl. Particularly suitable are: 2-methoxyethoxy (also known as 2'-O-methoxyethyl, 2'-MOE, or 2'-OCH2CH2OCH3), 2'-O-methyl (2'-O—CH3), 2'-fluoro (2'-F), or bicyclic sugar modified nucleosides having a bridging group connecting the 4' carbon atom to the 2' carbon atom wherein example bridge groups include —CH2-O—, —(CH2)2-O— or —CH2-N(R3)-O wherein R3 is H or C1-C12 alkyl.

One modification that imparts increased nuclease resistance and a very high binding affinity to nucleotides is the 2'-MOE side chain (Baker et al., J. Biol. Chem., 1997, 272, 11944-12000). One of the immediate advantages of the 2'-MOE substitution is the improvement in binding affinity, which is greater than many similar 2' modifications such as O-methyl, O-propyl, and O-aminopropyl. Oligonucleotides having the 2'-MOE substituent also have been shown to be antisense inhibitors of gene expression with promising features for in vivo use (Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

2'-Sugar substituent groups may be in the arabino (up) position or ribo (down) position. One 2'-arabino modification is 2'-F. Similar modifications can also be made at other positions on the oligomeric compound, particularly the 3' position of the sugar on the 3' terminal nucleoside or in 2'-5' linked oligonucleotides and the 5' position of 5' terminal nucleotide. Oligomeric compounds may also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, each of which is herein incorporated by reference in its entirety.

Representative sugar substituents groups are disclosed in U.S. Pat. No. 6,172,209 entitled "Capped 2'-Oxyethoxy Oligonucleotides," hereby incorporated by reference in its entirety.

Representative cyclic sugar substituent groups are disclosed in U.S. Pat. No. 6,271,358 entitled "RNA Targeted 2'-Oligomeric compounds that are Conformationally Preorganized," hereby incorporated by reference in its entirety.

Representative guanidino substituent groups are disclosed in U.S. Pat. No. 6,593,466 entitled "Functionalized Oligomers," hereby incorporated by reference in its entirety.

Representative acetamido substituent groups are disclosed in U.S. Pat. No. 6,147,200 which is hereby incorporated by reference in its entirety.

Nucleic acid molecules can also contain one or more nucleobase (often referred to in the art simply as "base") modifications or substitutions which are structurally distinguishable from, yet functionally interchangeable with, naturally occurring or synthetic unmodified nucleobases. Such nucleobase modifications can impart nuclease stability, binding affinity or some other beneficial biological property to the oligomeric compounds. As used herein, "unmodified" or "natural" nucleobases include the purine bases adenine (A) and guanine (G), and the pyrimidine bases thymine (T), cytosine (C) and uracil (U). Modified nucleobases also referred to herein as heterocyclic base moieties include other synthetic and natural nucleobases, many examples of which such as 5-methylcytosine (5-me-C), 5-hydroxymethyl cytosine, 7-deazaguanine and 7-deazaadenine among others.

Heterocyclic base moieties can also include those in which the purine or pyrimidine base is replaced with other heterocycles, for example 7-deaza-adenine, 7-deazaguanosine, 2-aminopyridine and 2-pyridone. Some nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases are particularly useful for increasing the binding affinity of the oligomeric compounds. These include 5-substituted pyrimidines, 6-azapyrimidines and N-2, N-6 and O-6 substituted purines, including 2 aminopropyladenine, 5-propynyluracil and 5-propynylcytosine.

Additional modifications to nucleic acid molecules are disclosed in U.S. Patent Publication 2009/0221685, which is hereby incorporated by reference.

The nucleic acid molecules disclosed herein may be introduced to a cell directly using techniques such as for example encapsulation in a nanoparticle or a liposome; electroporation; calcium phosphate precipitation and the like. In some embodiments, one or more nucleic acid molecules may be introduced to a cell as an element of a vector and thus comprise a DNA vector-based shRNA. Hereinafter, for simplicity the discussion will focus on compositions comprising shRNA although other compositions of the type described previously herein are also contemplated.

Vectors, including expression vectors, suitable for use in the present disclosure are commercially available and/or produced by recombinant DNA technology methods routine in the art. A vector containing a shRNA of this disclosure may have elements necessary for expression operably linked to such a molecule, and further can include sequences such as those encoding a selectable marker (e.g., a sequence encoding antibiotic resistance), and/or those that can be used in purification of a polypeptide (e.g., a His tag). Vectors suitable for use in this disclosure can integrate into the cellular genome or exist extrachromosomally (e.g., an autonomous replicating plasmid with an origin of replication).

In an embodiment, the vector is an expression vector and comprises additional elements that are useful for the expression of the nucleic acid molecules of this disclosure. Elements useful for expression include nucleic acid sequences that direct and regulate expression of nucleic acid coding sequences. One example of an element useful for expression is a promoter sequence. Examples of promoters suitable for use include the mouse U6 RNA promoters, synthetic human H1RNA promoters, SV40, CMV, RSV, RNA polymerase II, RNA polymerase III promoters, derivatives thereof, or combinations thereof. Elements useful for expression also can include ribosome-binding sites, introns, enhancer sequences, response elements, or inducible elements that modulate expression of a nucleic acid. Elements necessary for expression can be of bacterial, yeast, insect, mammalian, or viral origin and the vectors may contain a combination of elements from different origins. Elements necessary for expression are known to one of ordinary skill in the art and are described, for example, in Goeddel, 1990, Gene Expression Technology: Methods in Enzymology, 185, Academic Press, San Diego, Calif., the relevant portions of which are incorporated by reference herein. As used herein, operably linked means that a promoter and/or other regulatory element(s) are positioned in a vector relative to the shRNA in such a way as to direct or regulate expression of the molecule. A shRNA can be operably-linked to regulatory sequences in a sense or antisense orientation. In addition, expression can refer to the transcription of sense mRNA and may also refer to the production of protein.

C. Proteins and Polypeptides

Embodiments concern methods and compositions involving an NKG2D inhibitor that is a polypeptide. In certain embodiments, the NKG2D polypeptide inhibitors are used in the treatment or prevention of cancer or one or more tumors The terms "protein" and "polypeptide" are used interchangeably herein and they both cover what is understood as a "peptide" (a polypeptide molecule having 100 or fewer amino acid residures). In certain embodiments, the NKG2D inhibitor is a protein, polypeptide, or peptide; in particular embodiments, the NKG2D inhibitor is protein or polypeptide that is an antibody.

As will be understood by those of skill in the art, modification and changes may be made in the structure of a NKG2D inhibitor polypeptide or peptide, and still produce a molecule having like or otherwise desirable characteristics. For example, certain amino acids may be substituted for other amino acids or include deletions, additions, or truncations in the protein sequence without appreciable loss of interactive binding capacity with structures. Since it is the interactive capacity and nature of a protein that defines that protein's biological functional activity, certain amino acid sequence substitutions can be made in a protein sequence (or, of course, its underlying DNA coding sequence) and nevertheless obtain a protein with similar inhibitory properties. It is thus contemplated by the inventors that various changes may be made in the sequence of NKG2D inhibitor polypeptides or peptides (or underlying DNA) without appreciable loss of their biological utility or activity.

It is also well understood that where certain residues are shown to be particularly important to the biological or structural properties of a protein or peptide, e.g., residues in the binding site of an antibody, such residues may not generally be exchanged.

Some embodiments pertain to methods and compositions involving an inhibitor of NKG2D, wherein the inhibitor is an antibody that binds NKG2D.

The term "antibody" herein is used in the broadest sense and specifically includes full-length monoclonal antibodies, polyclonal antibodies, and, unless otherwise stated or contradicted by context, antigen-binding fragments, antibody variants, and multispecific molecules thereof, so long as they exhibit the desired biological activity. Generally, a full-length antibody is a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarily determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. General principles of antibody molecule structure and various techniques relevant to the production of antibodies are provided in, e.g., Harlow and Lane, ANTIBODIES: A LABORATORY MANUAL, Cold Spring Harbor Laboratory Press, Cold Spring Harbor, N.Y., (1988). An antibody inhibitor may be considered a neutralizing antibody.

The term "human antibody", as used herein, is intended to include antibodies having variable regions in which both the framework and CDR regions are derived from (i.e., are identical or essentially identical to) human germline immunoglobulin sequences. Furthermore, if the antibody contains a constant region, the constant region also is "derived from" human germline immunoglobulin sequences. The human antibodies may include amino acid residues not encoded by human germline immunoglobulin sequences (e.g., mutations introduced by random or site-specific mutagenesis in vitro or by somatic mutation in viva). However, the term "human antibody", as used herein, is not intended to include antibodies in which CDR sequences derived from the germline of another mammalian species, such as a mouse, have been grafted onto human framework sequences.

Included within the definition of an antibody that binds NKG2D is a NKG2D antibody binding fragment. As used herein, the term "NKG2D binding fragment" or "binding fragment thereof" encompasses a fragment or a derivative of an antibody that still substantially retain its biological activity of inhibiting NKG2D activity. Therefore, the term "antibody fragment" or NKG2D binding fragment refers to a portion of a full length antibody, generally the antigen binding or variable region thereof. Examples of antibody fragments include Fab, Fab', $F(ab')_2$, and Fv fragments; diabodies; linear antibodies; single-chain antibody molecules, e.g., sc-Fv; and multispecific antibodies formed from antibody fragments. Typically, a binding fragment or derivative retains at least 50% of its NKG2D inhibitory activity. Preferably, a binding fragment or derivative retains about or at least about 60%, 70%, 80%, 90%, 95%, 99% or 100% of its NKG2D inhibitory activity. It is also intended that a NKG2D binding fragment can include conservative amino acid substitutions that do not substantially alter its biologic activity.

The term "monoclonal antibody", as used herein, refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. In contrast, conventional (polyclonal) antibody preparations typically include a multitude of antibodies directed against (or specific for) different epitopes. The modifier "monoclonal" indicates the character of the antibody as being obtained from a substantially homogeneous population of antibodies, and is not to be construed as requiring production of the antibody by any particular method. For example, the monoclonal antibodies to be used in accordance with embodiments may be made by the hybridoma method first described by Kohler et al. (1975), or may be made by recombinant DNA methods (see, e.g., U.S. Pat. No. 4,816,567). The "monoclonal antibodies" may also be isolated from phage antibody libraries using the techniques described in Clackson et al. (1991) and Marks et al. (1991), for example.

As used herein, the term "humanized antibody" refers to forms of antibodies that contain sequences from non-human (e.g., murine) antibodies as well as human antibodies. Such antibodies are chimeric antibodies which contain minimal sequence derived from non-human immunoglobulin. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin.

Any suitable method for generating monoclonal antibodies may be used. For example, a recipient may be immunized with NKG2D or a fragment thereof. Any suitable method of immunization can be used. Such methods can include adjuvants, other immunostimulants, repeated booster immunizations, and the use of one or more immunization routes.

Any form of the antigen can be used to generate the antibody that is sufficient to generate a biologically active antibody. Thus, the eliciting antigen may be a single epitope, multiple epitopes, or the entire protein alone or in combination with one or more immunogenicity enhancing agents known in the art. The eliciting antigen may be an isolated full-length protein, a cell surface protein (e.g., immunizing with cells transfected with at least a portion of the antigen), or a soluble protein (e.g., immunizing with only the extracellular domain portion of the protein). The antigen may be produced in a genetically modified cell. The DNA encoding the antigen may genomic or non-genomic (e.g., cDNA) and encodes at least a portion of the extracellular domain. As used herein, the term "portion" refers to the minimal number of amino acids or nucleic acids, as appropriate, to constitute an immunogenic epitope of the antigen of interest. Any genetic vectors suitable for transformation of the cells of interest may be employed, including but not limited to adenoviral vectors, plasmids, and non-viral vectors, such as cationic lipids.

Embodiments may involve antibodies that reduce or inhibit NKG2D-mediated activation by, e.g., interfering with the NKG2D-binding of one or more endogenous NKG2D-ligands. For example, the antibodies may reduce or inhibit the NKG2D-binding of MICA; MICB; ULBP1; ULBP2; ULBP4; and/or RAET1-family member; e.g., by reducing or inhibiting the NKG2D-binding of MICA; or of MICA and MICB; or of MICA and ULBP3; or of MICA, MICB, and ULBP3; or of MICA, MICB, and all ULBP1, -2, -3, and 4; or of MICA, MICB, and one or more RAET1 family members. The ability of an antibody to inhibit NKG2D-binding of endogenous NKG2D-ligands can be evaluated using binding or competition assays described herein. In one embodiment, antibodies are capable of inhibiting at least 30% of ligand binding, or at least 50% of ligand binding, or at least 70% of ligand binding, or at least 80%, or at least 90% of ligand binding. In another embodiment, the IC50 for an antibody to inhibit the NKG2D-binding of 1 μg MICA-mFc is 1 nM or less, 0.5 nM or less, 0.2 nM or less, 0.1 nM or less, 0.05 nM or less, or 0.02 nM or less, 0.01 nM or less, 0.005 or less, or 0.002 or less. In another embodiment, full blockage of 1 .mu·g MICA-mFc binding is achieved at an anti-body concentration of 5 nM or less, 1 nM or less, 0.7 nM or less, 0.5 nM or less, or 0.2 nM or less, 0.1 nM or less, 0.05 nM or less, or about 0.02 nM or less. In one embodiment, an embodiment concerns antibodies, especially human antibodies, that are as efficient or more efficient in reducing or inhibiting ligand NKG2D-binding, such as, e.g., MICA binding to NKG2D, than any of ON72, BAT221, 5C6, 1D11, ECM217, and 149810, which are described in U.S. Pat. No. 7,879,985, which is incorporated by reference in its entirety.

Additionally or alternatively, an anti-NKG2D antibody can be capable of reducing the amount of cell-surface NKG2D upon (i.e., following) binding. (The terms "NKG2D antibody" and anti-NKG2D antibody" are used interchangeably herein.) Reduction of cell-surface associated NKG2D upon binding of an antibody can be an advantageous feature, because it reduces the number of NKG2D receptors available for ligand binding and subsequent activation (and tumor progression).

Accordingly, in one embodiment there are antibodies binding to NKG2D that are able to achieve maximum down-modulation of NKG2D at less than saturating concentrations. In another embodiment, such antibodies also compete with MS in binding to NKG2D. In another embodiment, such antibodies also bind to essentially the same NKG2D epitope as MS. An antibody used in embodiments can be capable of reducing cell surface NKG2D on cancer cells by at least 10%, at least 20%, at least 30%, at least 50%, at least 70%, or at least 90% as compared to cell-surface NKG2D in the absence of anti-NKG2D antibody or in the presence of a non-specific control antibody. In some embodiments, the antibodies achieve reduction of cell-surface NKG2D on cancer cells while causing no or minimal activation of NKG2D-receptor signalling, i.e., with no or minimal agonist activity. Exemplary assays for evaluating cell surface NKG2D and agonistic activity of anti-NKG2D antibodies are described in U.S. Pat. No. 7,879,985, which is incorporated by reference.

In another embodiment there are antibodies that compete with and/or bind to the same epitope on NKG2D as 16F16, 16F31, MS, and/or 21F2. Such antibodies can be identified based on their ability to cross-compete with 16F16, 16F31, MS, or 21F2 in standard NKG2D binding assay, such as is described in U.S. Pat. No. 7,879,985, which is incorporated by reference. In some embodiments, the antibody that binds to the same epitope on NKG2D as 16F16, 16F31, MS or 21F2 is a human monoclonal antibody.

In one embodiment, the epitope of an antibody comprises one or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2). In another embodiment, the epitope of an antibody comprises 5 or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2). In some embodiments, the epitope of an antibody comprises 8, 10, 12 or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2). In further embodiments, the epitope of an antibody comprises the residues Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2). In another embodiment, the epitope of an antibody consists essentially of the residues Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2). In other embodiments, the epitope of an antibody consists of one or more residues selected from Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2). In one embodiment, the epitope of an antibody consists of the residues Lys 150, Ser 151, Tyr 152, Thr 180, Ile 181, Ile 182, Glu 183, Met 184, Gln 185, Leu 191, Lys 197, Tyr 199, Glu 201, Thr 205, Pro 206, Asn 207 and Thr 208 of NKG2D (SEQ ID NO: 2).

In other embodiments, the epitope of an antibody comprises one or more residues involved in hydrogen-binding selected from Lys 150, Ser 151, Tyr 152, Ile 181, Met 184, Gln 185, Lys 197, Thr 205, and Asn 207 of NKG2D (SEQ ID NO: 2). In a further embodiment, the epitope of an antibody comprises 5 or more residues involved in hydrogen-binding selected from Lys 150, Ser 151, Tyr 152, Ile 181, Met 184, Gln 185, Lys 197, Thr 205, and Asn 207 of NKG2D (SEQ ID NO: 2). In one embodiment, the epitope of an antibody comprises Lys 150, Ser 151, Tyr 152, Ile 181, Met 184, Gln 185, Lys 197, Thr 205, and Asn 207 of NKG2D (SEQ ID NO: 2).

Some embodiments concern an antibody that exhibits at least one, or possibly two, three, four, five or more, of the following properties: (a) prevents NKG2D-mediated activation of an NKG2D-expressing cancer cell; (b) competes with at least one NKG2D ligand in binding to NKG2D, such as with at least MICA and ULBP3; (c) reduces the amount of NKG2D on the surface of a NKG2D-expressing cancer cell, such as by at least 75%; (d) binds to cynomolgous and/or rhesus NKG2D, such as with no less than 50% of the affinity by which it binds to human NKG2D; (e) binds to more than one form or conformation of NKG2D; (f) binds to NKG2D with a Kd of 1 nM or less, preferably 0.1 nM or less; (g) competes with one or more of 16F16, 16F31, MS, or 21F2 in binding to NKG2D, (h) competes more with 16F16, 16F31, MS, or 21F2 than with any of ON72, BAT221, 5C6, 1D11, ECM217, and 149810 in binding to NKG2D; (i) blocks more than 90% of 16F16, MS, or 21F2 binding to cell-surface NKG2D; (j) has insignificant or undetectable agonist activity, and (k) binds to essentially the same epitope as any of 16F16, 16F31, MS and/or 21F2, possibly essentially the same epitope as MS and/or 21F2. Any combination of the above-described functional features, and/or the functional features as described elsewhere, may be exhibited by an antibody used in embodiments described herein.

Embodiments may concern human monoclonal antibodies, including but not limited to 16F16, 16F31, MS, and 21F2 produced, isolated, and structurally and functionally characterized as described in U.S. Pat. No. 7,879,985. Full-length, variable, and CDR sequences of these antibodies are set forth in Table 1.

TABLE 1

FULL-LENGTH, VARIABLE AND CDR AMINO ACID SEQUENCES FOR 16F16, 16F31, MS AND 21F2

| Antibody portion | SEQ ID NO |
|---|---|
| 16F16 IgG4 H chain | 25 |
| 16F16 L chain | 26 |
| 16F31 IgG4 H chain | 27 |
| 16F16 L chain | 28 |
| 16F16 VH region | 29 |
| 16F16 VL region | 30 |
| 16F31 VH region | 31 |
| 16F31 VL region | 32 |
| 16F16 VH CDR1 | 33 |
| 16F16 VH CDR2 | 34 |
| 16F16 VH CDR3 | 35 |
| 16F16 VL CDR1 | 36 |
| 16F16 VL CDR2 | 37 |
| 16F16 VL CDR3 | 38 |
| 16F31 VH CDR1 | 39 |
| 16F31 VH CDR2 | 40 |
| 16F31 VH CDR3 | 41 |
| 16F31 VL CDR1 | 42 |
| 16F31 VL CDR2 | 43 |
| 16F31 VL CDR3 | 44 |
| MS IgG4 H chain | 45 |
| MS L chain | 46 |
| 21F2 IgG4 H chain | 47 |
| 21F2 L chain | 48 |
| MS VH region | 49 |
| MS VL region | 50 |
| 21F2 VH region | 51 |
| 21F2 VL region | 52 |
| MS VH CDR1 | 53 |
| MS VH CDR2 | 54 |
| MS VH CDR3 | 55 |
| MS VL CDR1 | 56 |
| MS VL CDR2 | 57 |
| MS VL CDR3 | 58 |
| 21F2 VH CDR1 | 59 |
| 21F2 VH CDR2 | 60 |
| 21F2 VH CDR3 | 61 |
| 21F2 VL CDR1 | 62 |
| 21F2 VL CDR2 | 63 |
| 21F2 VL CDR3 | 64 |

Certain anti-NKG2D antibodies has the same or a similar paratope as MS. In one embodiment, the antibody has a paratope comprising residues corresponding to one or more of Tyr 33 and Trp 97 of the MS L chain (SEQ ID NO: 46), and/or to one or more of Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 45). In one embodiment, the antibody has a paratope comprising residues corresponding to Tyr 33 and Trp 97 of the MS L chain (SEQ ID NO: 46), and/or to 3, 5, 7, 10 or more of Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 45). In one embodiment, the anti-body has a paratope comprising residues corresponding to Tyr 33 and Trp 97 of the MS L chain (SEQ ID NO: 41), and Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 45). In one embodiment, the antibody has a paratope consisting essentially of residues corresponding to Tyr 33 and Trp 97 of the MS L chain (SEQ ID NO: 46), and Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 45). In one embodiment, the antibody has a paratope consisting of residues corresponding to Tyr 33 and Trp 97 of the MS L chain (SEQ ID NO: 41), and Gln 1, Asp 26, Asp 27, Ser 30, Ser 31, Tyr 32, Tyr 33, His 50, Ser 52, Tyr 53, Ser 54, Ser 56, Ala 57, Asn 58, Trp 98 and Asp 99 of the MS H chain (SEQ ID NO: 45).

As 16F16, 16F31, 21F2, and MS can each bind to NKG2D, it may be possible to "mix and match" the respective $V_H$ and $V_L$ sequences of these antibodies to create other NKG2D inhibitors. The NKG2D-binding of such "mixed and matched" antibodies can be tested using the binding assays known to those of skill in the art (e.g., flow cytometry, Biacore, ELISAs) and/or using a cytotoxicity assay as described herein. In some embodiments, when $V_H$ and $V_L$ chains are mixed and matched, a $V_H$ sequence from a particular $V_H/V_L$ pairing is replaced with a structurally similar $V_H$ sequence. Likewise, in some embodiments a $V_L$ sequence from a particular $V_H/V_L$ pairing is replaced with a structurally similar $V_L$ sequence.

Accordingly, some embodiments provide an isolated monoclonal antibody, or antigen binding portion thereof, comprising: (a) a $V_H$ region comprising an amino acid sequence selected from the group consisting of SEQ ID NOS: 29, 31, 49, and 51, and (b) a $V_L$ region comprising an amino acid sequence selected from the group consisting of SEQ ID NOs: 30, 32, 50, and 52; wherein the antibody binds NKG2D. In certain embodiments, heavy and light chain combinations include: (a) a $V_H$ region comprising the amino acid sequence of SEQ ID NO: 29; and (b) a light chain variable region comprising the amino acid sequence of SEQ ID NO: 30; (a) a heavy chain variable region comprising the amino acid sequence of SEQ ID NO: 31; and (b) a light chain variable region comprising the amino acid sequence of SEQ ID NO: 32; (a) a $V_H$ region comprising the amino acid sequence of SEQ ID NO: 49; and (b) a light chain variable region comprising the amino acid sequence of SEQ ID NO: 51; or (a) a heavy chain variable region comprising the amino acid sequence of SEQ ID NO: 50; and (b) a light chain variable region comprising the amino acid sequence of SEQ ID NO: 52.

In another aspect, there are antibodies that comprise the heavy chain and light chain CDR1s, CDR2s and/or CDR3s of 16F16, 16F31, MS, or 21F2, or combinations thereof. The CDR regions are delineated using the Kabat system (Kabat et al. (1991) Sequences of Proteins of Immunological Interest, Fifth Edition, U.S. Department of Health and Human Services, NIH Publication No. 91-3242). See, e.g., FIGS. 4 and 5 of U.S. Pat. No. 7,879,985, which is incorporated by reference. In further embodiments the $V_H$ CDR1, 2 and 3 sequences and V$_L$ CDR1, 2 and 3 sequences are "mixed and matched" (i.e., CDRs from different antibodies can be mixed and match, although each antibody can contain a V$_H$ CDR1, 2 and 3 and a V$_L$ CDR 1, 2 and 3) to create other NKG2D inhibitors. The NKG2D-binding of such "mixed and matched" antibodies can be tested using the binding assays (e.g., flow cytometry, Biacore, or ELISAs). In some embodiments, the CDR1, CDR2 and/or CDR3 sequence from a particular V$_H$ sequence is replaced with a structurally similar CDR sequence(s). Likewise, when V$_L$ CDR sequences are mixed and matched, in further embodiments the CDR1, CDR2 and/or CDR3 sequence from a particular V$_L$ sequence preferably is replaced with a structurally similar CDR sequence(s). For example, the V$_L$ CDR1s and CDR3s of 16F16, 16F31, MS, and 21F2 and the VL CDR2 sequences of MS and 21F2 share some structural similarity and therefore are amenable to mixing and matching. It will be readily apparent to the ordinarily skilled artisan that different V$_H$ and V$_L$ sequences can be created by substituting one or more VH and/or VL CDR region sequences with structurally similar sequences from the CDR sequences disclosed herein for monoclonal antibodies 16F16, 16F31, MS, and 21F2.

Accordingly, in another aspect, there is an isolated monoclonal antibody, or antigen binding portion thereof comprising: (a) a V$_H$ CDR1 comprising an amino acid sequence selected from the group consisting of SEQ ID NOs: 33, 39, 53, and 59; (b) a VH CDR2 comprising an amino acid sequence selected from the group consisting of SEQ ID NOs: 34, 40, 54, and 60; (c) a V$_H$ CDR3 comprising an amino acid sequence selected from the group consisting of SEQ ID NOs: 25, 41, 55, and 61; (d) a V$_L$ CDR1 comprising an amino acid sequence selected from the group consisting of SEQ ID NOs:36, 42, 56, and 62; (e) a V$_L$ CDR2 comprising an amino acid sequence selected from the group consisting of SEQ ID NOs:37, 43, 57, and 62; and (f) a V$_L$ CDR3 comprising an amino acid sequence selected from the group consisting of SEQ ID NOs: 38, 44, 58, and 64; wherein the antibody binds NKG2D.

In some embodiments, the antibody comprises: (a) a V$_H$ CDR1 comprising SEQ ID NO:33; (b) a V$_H$ CDR2 comprising SEQ ID NO:34; (c) a V$_H$ CDR3 comprising SEQ ID NO:35; (d) a V$_L$ CDR1 comprising SEQ ID NO:36; (e) a V$_L$ CDR2 comprising SEQ ID NO: 37; and (f) a V$_L$ CDR3 comprising SEQ ID NO: 38.

In another embodiment, the antibody comprises: (a) a V$_H$ CDR1 comprising SEQ ID NO: 39; (b) a V$_H$ CDR2 comprising SEQ ID NO:40; (c) a V$_H$ CDR3 comprising SEQ ID NO:41; (d) a V$_L$ region CDR1 comprising SEQ ID NO:42; (e) a V$_L$ CDR2 comprising SEQ ID NO:43; and (f) a V$_L$ CDR3 comprising SEQ ID NO: 44.

In further embodiments, the antibody comprises: (a) a V$_H$ CDR1 comprising SEQ ID NO: 53; (b) a V$_H$ CDR2 comprising SEQ ID NO:54; (c) a V$_H$ CDR3 comprising SEQ ID NO:55; (d) a V$_L$ region CDR1 comprising SEQ ID NO:56; (e) a V$_L$ CDR2 comprising SEQ ID NO:57; and (f) a V$_L$ CDR3 comprising SEQ ID NO: 58.

In additional embodiments, the antibody comprises: (a) a V$_H$ CDR1 comprising SEQ ID NO: 59; (b) a V$_H$ CDR2 comprising SEQ ID NO:60; (c) a V$_H$ CDR3 comprising SEQ ID NO:61; (d) a V$_L$ region CDR1 comprising SEQ ID NO:62; (e) a V$_L$ CDR2 comprising SEQ ID NO:63; and (f) a V$_L$ CDR3 comprising SEQ ID NO: 64.

In more embodiments, the antibody comprises: (a) a V$_H$ CDR1 consisting of SEQ ID NO:33; (b) a V$_H$ CDR2 consisting of SEQ ID NO:34; (c) a V$_H$ CDR3 consisting of SEQ ID NO:35; (d) a V$_L$ CDR1 consisting of SEQ ID NO:36; (e) a V$_L$ CDR2 consisting of SEQ ID NO: 37; and (f) a V$_L$ CDR3 consisting of SEQ ID NO: 38.

In further embodiments, the antibody comprises: (a) a V$_H$ CDR1 consisting of SEQ ID NO: 39; (b) a V$_H$ CDR2 consisting of SEQ ID NO:40; (c) a V$_H$ CDR3 consisting of SEQ ID NO:41; (d) a V$_L$ region CDR1 consisting of SEQ ID NO:42; (e) a V$_L$ CDR2 consisting of SEQ ID NO:43; and (f) a V$_L$ CDR3 consisting of SEQ ID NO: 44.

In another embodiment, the antibody comprises: (a) a V$_H$ CDR1 consisting of SEQ ID NO: 53; (b) a V$_H$ CDR2 consisting of SEQ ID NO:54; (c) a V$_H$ CDR3 consisting of SEQ ID NO:55; (d) a V$_L$ region CDR1 consisting of SEQ ID NO:56; (e) a V$_L$ CDR2 consisting of SEQ ID NO:57; and (f) a V$_L$ CDR3 consisting of SEQ ID NO: 58.

In some embodiments, the antibody comprises: (a) a V$_H$ CDR1 consisting of SEQ ID NO: 53; (b) a V$_H$ CDR2 consisting of SEQ ID NO:54; (c) a V$_H$ CDR3 consisting of SEQ ID NO:55; (d) a V$_L$ region CDR1 consisting of SEQ ID NO:56; (e) a V$_L$ CDR2 consisting of SEQ ID NO:57; and (f) a V$_L$ CDR3 consisting of SEQ ID NO: 58, and residues corresponding to one, two, or all of Gln 1, Asp 26, and Asp 27 in the MS H chain (SEQ ID NO: 45).

In certain embodiments, the antibody comprises: (a) a V$_H$ CDR1 consisting of SEQ ID NO: 59; (b) a V$_H$ CDR2 consisting of SEQ ID NO:60; (c) a V$_H$ CDR3 consisting of SEQ ID NO:61; (d) a V$_L$ region CDR1 consisting of SEQ ID NO:62; (e) a V$_L$ CDR2 consisting of SEQ ID NO:63; and (f) a V$_L$ CDR3 consisting of SEQ ID NO: 64.

In certain other embodiments, an antibody comprises a V$_H$ region from a particular germline H chain immunoglobulin gene, or a combination of particular germline H chain immunoglobulin genes; and/or a V$_L$ region from a particular germline L chain immunoglobulin gene, or a combination of particular germline L chain immunoglobulin genes. Such combinations can be obtained, e.g., in vivo via somatic recombination in a B cell.

For example, in one embodiment, there is an isolated anti-NKG2D antibody, or an antigen-binding fragment thereof, wherein the antibody: (a) comprises a V$_H$ region from a human VH3_21, VH3_20, VH4_59, or VH5_51 gene recombined with a human D3-9, D3-10, or D3_10_R3 gene and a JH3, JH4 or JH6 gene, (b) comprises a V$_L$ region derived from a human VKI_L15 or VKIII_A27 or VKIII_L6 gene recombined with a human JK1, JK2 or JK3 gene, and (c) the antibody binds to NKG2D.

In another embodiment, there is an isolated anti-NKG2D antibody, or an antigen-binding fragment thereof, comprising a V$_H$ region obtained by a recombination of human VH3_21, D3-9, and JH4 genes and a V$_L$ region obtained by a recombination of human VKI_L15 and JK2 genes.

Other embodiments concern isolated anti-NKG2D antibody, or an antigen-binding fragment thereof, comprising a V$_H$ region obtained by a recombination of human VH3_20, D3-10, and JH6 genes and a VL region obtained by a recombination of human VKIII_A27 and JK3 genes.

In further embodiments, there are isolated anti-NKG2D antibodies, or antigen-binding fragments thereof, comprising a V$_H$ region obtained by a recombination of human VH4_59, a D gene, and JH3 genes and a V$_L$ region obtained by a recombination of human VKIII_A27 and JK1 genes.

In another embodiment, where is an isolated anti-NKG2D antibody, or an antigen-binding fragment thereof, comprising a V$_H$ region obtained by a recombination of human VH5_51. D3_10_R3, and JH4 genes and a V$_L$ region obtained by a recombination of human VKIII_L6 and JK1 genes.

In separate and specific embodiments, the invention provides isolated anti-NKG2D antibodies obtained by introducing one, two, three, four or more amino acid substitutions and/or somatic hypermutations in the $V_H$ and/or $V_L$ region of an anti-NKG2D antibody described above.

As used herein, a human antibody comprises heavy or light chain variable regions "of" or "derived from" or that are "the product of" a particular germline sequence if the variable regions of the antibody are obtained from a system (as described below) that uses human germline immunoglobulin genes. Such "systems" include immunizing a transgenic mouse carrying human immunoglobulin genes with the antigen of interest or screening a human immunoglobulin gene library displayed on phage with the antigen of interest. A human antibody that is "of" or "derived from" or "the product of" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "of" or "derived from" or "the product of" a particular human germline immunoglobulin sequence may contain amino acid differences as compared to the germline sequence, due to, for example, naturally-occurring somatic mutations or intentional introduction of site-directed mutation(s) (which may be selected substitutions).

However, a human antibody is typically at least 90% identical in amino acid sequence to an amino acid sequence encoded by a recombed germline immunoglobulin sequence and can usually be identified as human when compared to the germline immunoglobulin amino acid sequences of other species (e.g., murine germline sequences). In certain cases, a human antibody may be at least 95%, or even at least 96%, 97%, 98%, or 99% identical in amino acid sequence to the amino acid sequence encoded by the recombed germline immunoglobulin gene.

Typically, a human antibody derived from a particular human germline sequence will display no more than 10 amino acid differences from the amino acid sequence encoded by the human germline immunoglobulin gene. In certain cases, the human antibody may display no more than 8, no more than 5, or even no more than 4, 3, 2, or 1 amino acid difference, or no amino acid difference, from the amino acid sequence encoded by the recombed germline immunoglobulin gene.

In yet another embodiment, an antibody comprises heavy and light chain variable regions comprising amino acid sequences that are homologous to the amino acid sequences of the antibodies described herein, and wherein the antibodies retain the desired functional properties of the NKG2D inhibitors. For example, embodiments concern an isolated antibody, or antigen binding portion thereof, comprising a heavy chain variable region and a light chain variable region, wherein: (a) the $V_H$ region comprises an amino acid sequence that is at least 80% identical to an amino acid sequence selected from the group consisting of SEQ ID NOs: 11, 13, 44, and 46; (b) the $V_L$ region comprises an amino acid sequence that is at least 80% identical to an amino acid sequence selected from the group consisting of SEQ ID NOs: 12, 14, 45, and 47; (c) the anti-body binds to NKG2D and exhibits at least one of the functional properties described herein, preferably several of the functional properties described herein.

In other embodiments, the $V_H$ and/or $V_L$ amino acid sequences may be 85%, 90%, 95%, 96%, 97%, 98% or 99% identical to the sequences set forth above. An antibody having VH and VL regions having high (i.e., 80% or greater) identity to the $V_H$ and $V_L$ regions of the sequences set forth above, can be obtained by mutagenesis (e.g., site-directed or PCR-mediated mutagenesis) of nucleic acid molecules encoding SEQ ID NOs:11-14 or 44-47, followed by testing of the encoded altered antibody for retained function (e.g., NKG2D binding affinity, NKG2D-ligand blocking, NKG2D downmodulation, or reduction of NKG2D binding to DAP10) using the functional assays described herein.

The percent identity between the two sequences is a function of the number of identical positions shared by the sequences (i.e., % identity=# of identical positions/total # of positions.times.100), taking into account the number of gaps, and the length of each gap, which need to be introduced for optimal alignment of the two sequences. The comparison of sequences and determination of percent identity between two sequences can be accomplished using a mathematical algorithm in sequence-analysis software. Protein analysis software matches similar sequences using measures of similarity assigned to various substitutions, deletions and other modifications, including conservative amino acid substitutions.

D. Small Molecules

In some embodiments, an NKG2D inhibitor is a small molecule, which refers to a small compound that is biologically active but is not a polymer. It does refer to a monomer. Libraries of small molecules may be screened for candidate NKG2D inhibitors.

E. Formulations and Modes of Administration

The present invention concerns substances that can be used to prevent or treat conditions or diseases. In particular, embodiments concern NKG2D inhibitors as preventative and therapeutic agents. Methods may be employed with respect to individuals who have been diagnosed with a particular inflammatory condition or disease or who are deemed to be at risk for an inflammatory condition or disease.

It is contemplated that compositions of the invention may be administered to a patient within about 1, 2, 3, 4, 5, 10, 15, 20, 25, 30, 35, 40, 45, 50, 55 minutes, 1, 2, 3, 4, 5, 6, 7, 8, 9, 10, 11, 12, 13, 14, 15, 16, 17, 18, 19, 20, 21, 22, 23, 24 hours, 1, 2, 3, 4, 5, 6, 7 days, 1, 2, 3, 4, 5 weeks, and/or 1, 2, 3, 4, 5, 6, 7, 8, 9, 10, 11, 12 months of being diagnosed with a inflammatory condition or disease, identified as having symptoms of an inflammatory condition or disease, or identified as at risk for an inflammatory condition or disease.

In certain embodiments, a course of treatment will last 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90 days or more. It is contemplated that one agent may be given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, any combination thereof, and another agent is given on day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, and/or 90, or any combination thereof. Within a single day (24-hour period), the patient may be given one or multiple administrations of the agent(s). Moreover, after a course of treatment, it is contemplated that there is a period of time at which no other treatment is administered. This time period may last 1, 2, 3, 4, 5, 6, 7 days, and/or 1, 2, 3, 4, 5 weeks, and/or 1, 2, 3, 4, 5, 6, 7, 8, 9, 10, 11, 12 months or more, depending on the condition of the patient, such as their prognosis, strength, health, etc.

In particular embodiments, compositions may be administered 1, 2, 3, 4, 5, 6, 7, 8, 9, 10, 11, 12, 13, 14, 15, 16, 17, 18, 19, 20 or more times, and/or they may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months, or any range or combination derivable therein.

Compounds and compositions may be administered to a patient intratumorally, intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, directly, topically, locally, by inhalation, by injection, by infusion, by continuous infusion, by localized perfusion bathing target cells directly, via a catheter, via nebulizer, via aerosol, or via a lavage. In certain embodiments, inflamed tissue is directly administered a NKG2D inhibitor. In certain embodiments target cells are tumor or cancer cells. In certain embodiments, a patient is administered an NKG2D inhibitor by direct injection to a tumor or tumor bed before or after tumor resection.

In certain embodiments, the composition is administered intravenously. Intratumorally, or intratracheally. Examples of other routes of administration include intravitreal administration, intralesional administration, intratumoral administration, topical administration to the surface of the eye, topical application to the surface of a tumor, direct application to a neovascular membrane, subconjunctival administration, periocular administration, retrobulbar administration, subtenon administration, intracameral administration, subretinal administration, posterior juxtascleral administration, and suprachoroidal administration.

In some embodiments, pharmaceutical compositions are administered to a subject. Different aspects of the present invention involve administering an effective amount of a composition to a subject. Such compositions will generally be dissolved or dispersed in a pharmaceutically acceptable carrier or aqueous medium.

The phrases "pharmaceutically acceptable" or "pharmacologically acceptable" refer to molecular entities and compositions that do not produce an adverse, allergic, or other untoward reaction when administered to an animal, or human. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration (which may include enterically coated formulations); time release capsules; and any other form currently used, including inhalants and the like.

The active compounds of the present invention can be formulated for parenteral administration, e.g., formulated for injection via the intravenous, intramuscular, sub-cutaneous, or even intraperitoneal routes. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. A solution may be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7. 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9% or more of the NKG2D inhibitor, or any range derivable therein.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

Such compositions would normally be administered as pharmaceutically acceptable compositions that include physiologically acceptable carriers, buffers or other excipients. As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

For parenteral administration in an aqueous solution, for example, the solution should be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media which can be employed will be known to those of skill in the art in light of the present disclosure. For example, one dosage could be dissolved in isotonic NaCl solution and either added to hypodermoclysis fluid or injected at the proposed site of infusion, (see for example, Remington's Pharmaceutical Sciences, 1990). Some variation in dosage will necessarily occur depending on the condition of the subject. The person responsible for administration will, in any event, determine the appropriate dose for the individual subject.

An effective amount of therapeutic or prophylactic composition is determined based on the intended goal. The term "unit dose" or "dosage" refers to physically discrete units suitable for use in a subject, each unit containing a predetermined quantity of the composition calculated to produce the desired responses discussed above in association with its administration, i.e., the appropriate route and regimen. The quantity to be administered, both according to number of treatments and unit dose, depends on the protection desired.

Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition.

Upon formulation, solutions will be administered in a manner compatible with the dosage formulation and in such amount as is therapeutically or prophylactically effective. The formulations are easily administered in a variety of dosage forms, such as the type of injectable solutions described above.

G. Screening Methods

Embodiments further comprises methods for identifying NKG2D receptor inhibitors. These assays may comprise random screening of large libraries of candidate substances; alternatively, the assays may be used to focus on particular classes of compounds selected with an eye towards structural attributes that are believed to make them more likely to modulate the function or expression of NKG2D.

By function, it is meant that one may assay for a measurable effect on inhibiting or reducing NKG2D receptor activity. To identify a NKG2D inhibitor, one generally will determine the activity or expression level of NKG2D in the presence and absence of the candidate substance, wherein a candidate NKG2D inhibitor or is defined as any substance that alters these characteristics. For example, a method generally comprises:

(a) providing a candidate NKG2D inhibitor;
(b) admixing the candidate inhibitor with an NKG2D protein or cell expressing the protein;
(c) measuring one or more characteristics of the compound or cell in step (b); and
(d) comparing the characteristic measured in step (c) with the characteristic of the compound or cell in the absence of said candidate modulator,
wherein a difference between the measured characteristics indicates that said candidate modulator is, indeed, a modulator of the compound or cell.

Assays may be conducted in cell free systems, in isolated cells, or in organisms including transgenic animals.

It will, of course, be understood that all the screening methods of the present invention are useful in themselves notwithstanding the fact that effective candidates may not be found. The invention provides methods for screening for such candidates, not solely methods of finding them.

As used herein the term "candidate substance" refers to any molecule that may be a inhibitor of an NKG2D receptor, i.e., inhibit NKG2D receptor activity as discussed above or NKG2D expression.

The candidate substance may be a protein or fragment thereof, a small molecule, or even a nucleic acid molecule. An example of pharmacological compounds will be compounds that are structurally related to NKG2D, or a molecule that binds NKG2D such as an antibody. Using lead compounds to help develop improved compounds is know as "rational drug design" and includes not only comparisons with know inhibitors and activators, but predictions relating to the structure of target molecules.

Other suitable modulators include antisense molecules, ribozymes, and antibodies (including single chain antibodies), each of which would be specific for the target molecule. Such compounds are well known to those of skill in the art. For example, an antisense molecule that bound to a translational or transcriptional start site, or splice junctions, would be ideal candidate inhibitors.

III. EXAMPLES

The following examples are given for the purpose of illustrating various embodiments of the invention and are not meant to limit the present invention in any fashion. One skilled in the art will appreciate readily that the present invention is well adapted to carry out the objects and obtain the ends and advantages mentioned, as well as those objects, ends and advantages inherent herein. The present examples, along with the methods described herein are presently representative of preferred embodiments, are exemplary, and are not intended as limitations on the scope of the invention. Changes therein and other uses which are encompassed within the spirit of the invention as defined by the scope of the claims will occur to those skilled in the art.

Example 1

Materials and Methods for Examples 2-9

Cancer Specimens and Cell Lines, Immunohistochemistry, and Flow Cytometry.

Primary cancer, non-affected tissue specimens, and pathology reports were provided by the Cooperative Human Tissue Network (CHTN)—Western Division. This activity was approved by the Institutional Review Board of the Fred Hutchinson Cancer Research Center (Seattle, Wash.). If two tumor grades were found within one cancer specimen, the higher grade was used for classification. Tumor cell lines were from the American Type Culture Collection (ATCC). Tumor cell lines BT-20, MDA-MB-453, HTB-78, AGS, MDA-MB-231, DLD-1, PC3, and A375 were grown in RPMI 1640, and MCF-7 in Eagle's minimal essential medium (EMEM) plus insulin (0.01 mg/ml; Sigma), both media supplemented with 10% FBS. The mouse TEC and PAM 212 lines were from the ATCC, and C2H was provided by Dr. Norm Greenberg (FHCRC). Abs for immunohistochemistry and flow cytometry of cell surface markers were mAb together with HRP-conjugated secondary reagents and mAb-fluorochrome conjugates, respectively, to NKG2D (clone 1D11, -APC; 3), MICA/MICB (clone 6D4, -PE; 7), CD45 (clone 2D1, -APC-Cy7), CD3 (clone UCHT1) (all from BD Pharmingen), and EpCAM (clone 9C4, -Alexa Fluor 488; BioLegend). Binding of anti-ULBP1-5 antibodies (mAbs 3F1, 6F6, 4F9, 6E6, and 6D10; 14) was visualized with a PE-conjugated secondary reagent. Cancer cell viability was assessed using a LIVE/DEAD Fixable Violet Dead Cell Stain kit (Invitrogen). Immunohistochemistry stainings of tissue cryosections employed the Envision System (Dako) protocol. Cells were examined for mAb surface stainings using a BD LSR II flow cytometer and FlowJo software (Tree Star).

Immunoprecipitations and Immunoblots.

NKG2D was immunoprecipitated from standard NP-40 buffer lysates of FACSAria-sorted EpCAM$^+$CD45$^-$ cancer cells (~5×10$^6$ per lane), tumor lines (~5×10$^7$ cells; 2×10$^7$ cells with BT-20), and transfectants (5×10$^6$ cells) using mAb 5C6 immobilized on AminoLink Plus Coupling Resin (Pierce). DAP10 was immunoprecipitated using rabbit polyclonal antibodies (FL-93; Santa Cruz Biotechnology). Immunoblots were probed with polyclonal antibodies to NKG2D or DAP10 (N-20 and N-17; Santa Cruz Biotechnology), or Grb2 (Cell Signaling Technology) and developed using secondary reagents and Supersignal West Dura Extended Duration Substrate (Pierce). Immunoprecipitation and immunoblot detection of mouse NKG2D utilized a rat mAb (clone 191004; R&D Systems) and goat polyclonal reagent (H-15; Santa Cruz Biotechnology), respectively. For P-AKT induction, cancer cells and tumor lines (2×10$^6$ cells per experimental condition) cultured in 6-well plates were desensitized for 16 h and 4-24 h, respectively, in serum-free RPMI at 37° C. before exposure in 0.5 ml RPMI to insulin (5 µg/ml; 35 min at 37° C.), mAb 1D11 (purified with MabTrap Kit; GE Healthcare Life Sciences) or mAb 5C6 F(ab')$_2$ (produced with Pierce F(ab')$_2$ preparation kit) (each 5 µg/ml; 30 min at 4° C.). For crosslinking, washed cells in 0.2 ml RPMI were exposed to goat anti-mouse F(ab')$_2$ (20 µg/ml; 5 min at 37° C.; Jackson ImmunoResearch). Wortmannin (100 nM; Sigma) was applied 2 h before stimulations. Reactions were terminated on ice by addition of 1 ml sodium orthovanadate (Na$_3$VO$_4$, 2 mM in cold PBS; Calbiochem) and cells resuspended in NP-40 lysis buffer with protease inhibitor cocktail (Roche) and Na$_3$VO$_4$. Cleared supernatants were subjected to SDS-PAGE (4-12% gradient NuPAGE gels; Invitrogen) and proteins electroblotted onto PVDF membranes (Immobilon-P; Millipore), which were probed with rabbit anti-human phospho-AKT(S473) (clone 193H12) or pan-AKT (clone C67E7), secondary HRP-conjugated anti-rabbit IgG (all from Cell Signaling Technology), and chemiluminescent reagent. For immunoblot detection of P-mTOR(S2448), P-S6K1(T389), and P-4E-BP1 (T37/46), cells grown at low density in 6-well plates were desensitized for 24 h in serum-free RPMI and 4-6 h in Hank's balanced salt solution (HBSS; Invitrogen) at 37° C. Inhibitors wortmannin (100 nM) and rapamycin (50 nM; LC Laboratories) were added after 2 h of desensitization. Detached cells were sequentially washed and exposed to 1D11 mAb and crosslinking Ab in 0.5 and 0.2 ml cold HBSS, respectively, and processed as above. Sample electrophoresis was in 3-8% (mTOR) and 4-12% (4E-BP1) gradient NuPAGE gels. Phosphoproteins and protein controls were detected using rabbit polyclonal antibodies (to P-mTOR, P-S6K1, and P-4E-BP1), mAbs (clones 7C10, 236B4, and 53H11), and anti-rabbit IgG-HRP (all from Cell Signaling Technology). MAPKs were detected with cells grown to semi-confluence in 6-well plates and desensitized for 24 h. Wortmannin (200 nM) or inhibitors of MEK/ERK (U0126, 10 µM; Cell Signaling Technology) or JNK (SP600125, 100 µM; Sigma) were added 30 min before stimulations. EGF (rhEGF, 100 ng/ml; Sigma) was added for 10-20 min at 37° C., and sMICA (1 µg/ml; purified from culture supernatants of transfected 293T cells) followed by crosslinking anti-His tag Ab (0.5 µg/ml; eBioscience) for 30 min and 2 min (for P-ERK1/2) or 15 min (for P-JNK) at 4° C. and 37° C., respectively. Samples were processed as above, run in 4-12% gradient NuPAGE gels, and immunoblots probed using rabbit mAb to P-p44/42 MAPK (ERK1/2(T202/Y204)) and P-SAPK/JNK(T183/Y185) (clones 137F5 and 81E11) and polyclonal antibodies to protein controls (all from Cell Signaling Technology).

RT-PCR, NKG2D-DAP10 Transfection, and siRNA Transduction.

Annealed siRNA oligonucleotides were ligated into lentiviral pRRLsin-cPPT-PGK-GFPwpre vector modified by insertion of a U6 gene promoter cassette (42).

Primers (forward and reverse listed 5'-3') for human NKG2D, DAP10, and GAPDH RT-PCR were ATGGGGTG-GATTCGTGGTCGGA (SEQ ID NO:3) and CACAGTC-CTTTGCATGCAGATGTACGTA (SEQ ID NO:4) (648 bp amplicon), GTCCACCATGATCCATCTGGG (SEQ ID NO:5) and G TCAAAGGTCCAAGCTGCAGG (SEQ ID NO:6) (314 bp amplicon), and AGCCACATCGCTCAGA-CACC (SEQ ID NO:7) and GATACCCTTTTGGCTCCCC (SEQ ID NO:8) (379 bp amplicon), respectively. PCR conditions were 30 cycles at 94° C. (denaturing, 15 seconds), 62° C. (annealing, 30 seconds), and 72° C. (extending, 1 min). Primers for murine NKG2D(L), NKG2D(S), DAP10, DAP12, and GAPDH were ATGGCATTGAT-TCGTGATCGAA (SEQ ID NO:9) and TTACACCGC-CCTTTTCATGC (SEQ ID NO:10) (699 bp amplicon), GGATCTCCCTTCTCTGCTCAGAG (SEQ ID NO:11) and TTACACCGCCCTTTTCATGC (SEQ ID NO:12) (683 bp amplicon), ATGGACCCCCCAGGCTACCT (SEQ ID NO:13) and TCAGCCTCTGCCAGGCATG (SEQ ID NO:14) (240 bp amplicon), CAGAGTGACACTTTC-CCAAGATG (SEQ ID NO:15) and TCATCTGTAATATT- GCCTCTGTGTG (SEQ ID NO:16) (264 bp amplicon), and AACTTTGGCATTGTGGAAGG (SEQ ID NO:17) and GGAGACAACCTGGTCCTCAG (SEQ ID NO:18) (351 bp amplicon), respectively. MCF-7 and A375 cells were co-transfected with NKG2D and DAP10 cDNAs in pcDNA3.1 vectors using Lipofectamine 2000 (Invitrogen) and selected for neomycin (G418; Gibco-BRL) and hygromycin (Roche) resistance. Oligonucleotide pairs (all listed 5'-3'; internal hairpin sequence, 3'-end termination signal, and Xba I and Eco RV overhangs underlined) for siRNAs targeting NKG2D (KLRK1; GenBank accession number X54870 (SEQ ID NO:1)) and DAP10 (DNAX-activating protein 10, HCST; GenBank accession number AF072844 (SEQ ID NO:2)) mRNAs at positions 690-710 and 165-193 were CTAGACCCAACCTACTAACAATAATTTCAAGA-GAATTATTGTTAGTAGGTTGGGT TTTTGAT (SEQ ID NO:19) and ATCAAAAAACCCAAC-CTACTAACAATAATTCTCTTGAAATTATTGTTAG-TAGGTT GGGT (SEQ ID NO:20), and CTAGAAGCTCA-GACGACTCCAGGAGAGAGATCATTCAAGAGATG-ATCTCTCTCCT GGAGTCGTCTGAGCTTTTTTTGAT (SEQ ID NO:21) and ATCAAAAAAAGCTCAGAC-GACTCCAGGAGAGAGATCATCTCTTGAATGATCTCT CTCCTGGAGTCGCTGAGCTT (SEQ ID NO:22), respectively. The control scrambled siRNA oligonucleotides were CTAGAGGGTATGTATGCTTGGTAGTCTATCTTCT-TCTTAGACTACCAAGCATACAT ACCCTTTTGAT (SEQ ID NO:23) and ATCAAAAAAGGGTATGTATGCT-TGGTAGTCTAAGAAGAAGATAGACTACCAAGC ATACATACCCT (SEQ ID NO:24). Annealed oligonucleotide pairs were ligated into lentiviral pRRLsin-cPPT-PGK-GFPwpre vector modified by insertion of a U6 gene promoter cassette and constructs sequenced (42). For virus production, 293T cells on poly-L-lysine-coated plates were transfected with expression constructs together with envelope helper (pMD2.G) and gag/pol helper (pCMVR8.74) plasmids using calcium phosphate. Virus in culture supernatants was concentrated by centrifugation, titered and used for infection enhanced by addition of protamine sulfate (MP Biomedicals), of MCF-7 cells and transfectants, which were sorted for GFP expression. Real-time RT-PCR for NKG2D, DAP10, and control 18S rRNA was performed using Taqman probes (hs00183683, hs00367159, and 4333760T; Applied Biosystems), Platinum Quantitative PCR Super-Mix-UDG reaction reagent (Invitrogen), and an Applied Biosystems 7900HT Fast Real-Time PCR System.

Cell Cycle Analysis and Metabolic Activity Assays.

DNA contents were determined with 70% EtOH-permeabilized and fixed cells treated with PI/RNase staining buffer (BD Pharmingen). Prior to analysis, cells were plated for 24 h in the presence or absence of each 10 μg/ml anti-MIC and -ULBP3 and -ULBP4 mAb or control Ig. Flow cytometry data were analysed using FlowJo cell cycle software with quantitative analysis based on Dean-Jett-Fox model curve fitting. Cellular ATP was determined using the ATPlite luminescence assay system (PerkinElmer). Real-time oxygen consumption and extracellular acidification rates were measured employing the Seahorse Bioscience Extracellular Flux Analyzer XF24 with cells ($3\times10^4$) seeded in custom 24-well plates and grown overnight (34). Metabolic rates were calculated from multiple measurements in buffer-free medium within one h at 37° C. Differences in cell growth rates were accounted for by using fluorescence emission values of Hoechst stainings to calculate normalization factors for cell number corrections.

Statistical Analysis.

The two-sample t-test was used to compare mean percentages of NKG2D positive cancer cells according to lymph node status (yes or no) and the presence or absence of lymphatic and/or vascular invasion. Linear regression was used to assess the correlation with age, and tumor stage, grade, and size/spread, each numerically categorized with values 1-4 (for Stage I-IV and T1-T4, as well as grade 0-3). The associations were assumed to be similar across each cancer, and results should be interpreted with this assumption in mind. The ability to test this assumption is limited by the relatively small number of patients in the various cancer groups.

Example 2

Expression of NKG2D-DAP10 on Cancer Cells

In the course of examining primary breast and epithelial ovarian cancer specimens for infiltrating lymphocytes by immunohistochemistry, the inventors observed unambiguous cancer tissue stainings for the NKG2D receptor using the specific 1D11 mAb and HRP-conjugated secondary reagent (FIG. 1A) (Bauer et al., 1999). The staining patterns were similar to those recorded for the MIC ligands of NKG2D that were detected with the bispecific 6D4 mAb (Groh et al., 1999). In comparison, tumor infiltrating CD3+ lymphocytes, among which most CD8 T cells are positive for NKG2D, were infrequent and scattered. Stainings for NKG2D of normal breast, ovary, and prostate tissue sections including well recognizable epithelial areas gave negative results (FIG. 1B).

Cell surface expression and composition of NKG2D receptor complexes were examined with cancer cell suspensions sorted for an EpCAM+CD45− phenotype to ensure analysis of epithelial tumor cells and exclusion of hematopoietic cells. The epithelial nature of EpCAM+CD45− cells was separately confirmed by stainings for pan-cytokeratin. Flow cytometry analysis showed that 12/12 breast, 14/14 colon, 29/30 epithelial ovarian, and 4/4 prostate cancer specimens included cancer cell populations that were positive for surface NKG2D, with proportional ranges of 4-83% (mean 23%, SD +/−22.3), 4-39% (mean 16%, SD +/−10.6), 1-65% (mean 18%, SD +/−17.3), and 3-33% (mean 11%, SD +/−14.7), respectively (FIG. 1C). Sizeable proportions of all cancer cell suspensions expressed the MIC ligands of NKG2D.

Figure 1D:
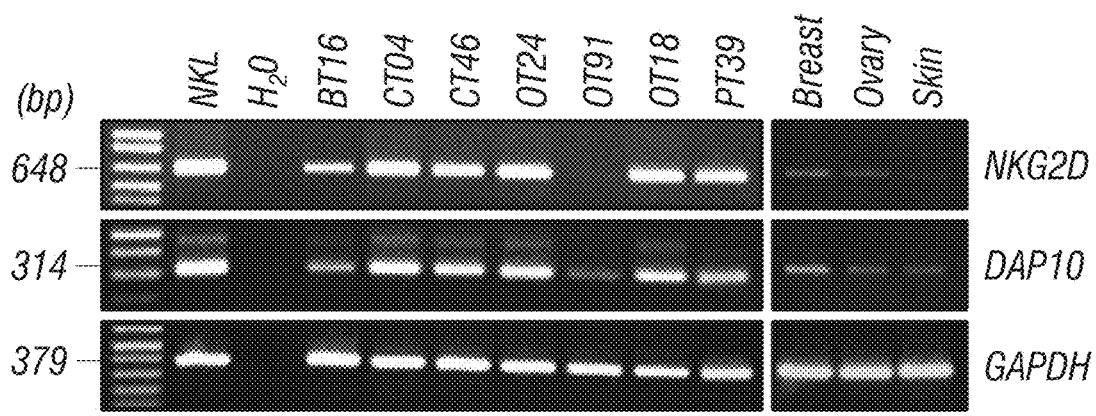
Figure 1E:
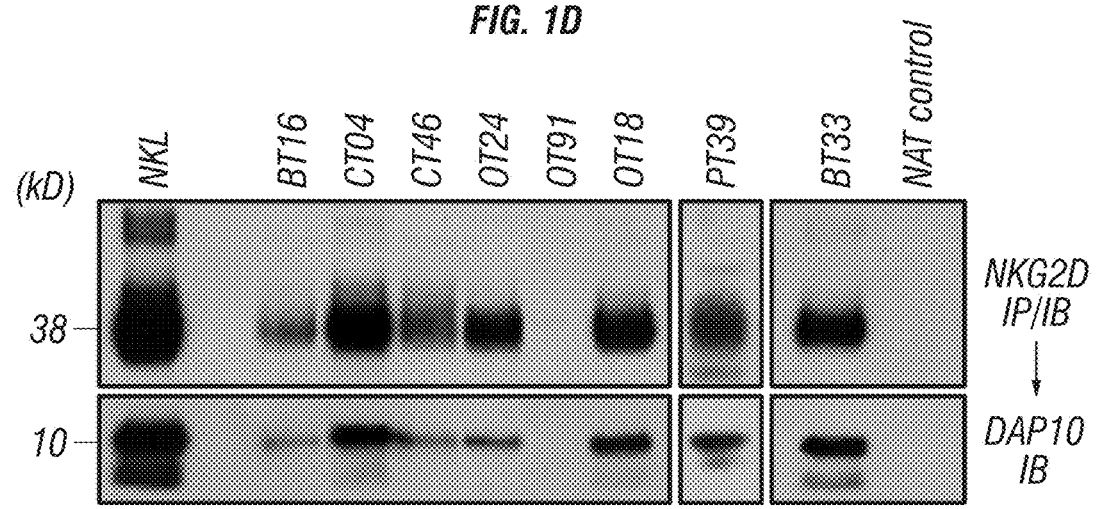

The inventors next tested whether cancer cells also express the DAP10 signaling adaptor (Wu et al., 1999; Upshaw and Leibson, 2006; Lanier, 2008). By standard 30-cycle RT-PCR, NKG2D and DAP10 cDNA amplicons were readily detected with 6/7 breast, ovarian, colon, and prostate EpCAM+CD45− cancer cell suspensions. Upon sequencing, the inventors found no changes in the canonical amino acid coding regions. Only faint signals were recorded with mRNAs from non lymphocyte-depleted normal breast, ovarian, and skin tissues (FIG. 1D). Cancer cell expression of NKG2D-DAP10 complexes was confirmed by immunoprecipitations, using bead-coupled anti-NKG2D 5C6 mAb (Bauer et al., 1999), followed by SDS-PAGE and sequential immunoblot probing for NKG2D and DAP10. Direct comparison of a breast cancer sample with matched non-affected tissue control further illustrated the malignancy-associated expression of NKG2D-DAP10 (FIG. 1E).

Example 3

Triggering of NKG2D Stimulates PI3K-Dependent Phosphorylation of AKT

Figure 1G:
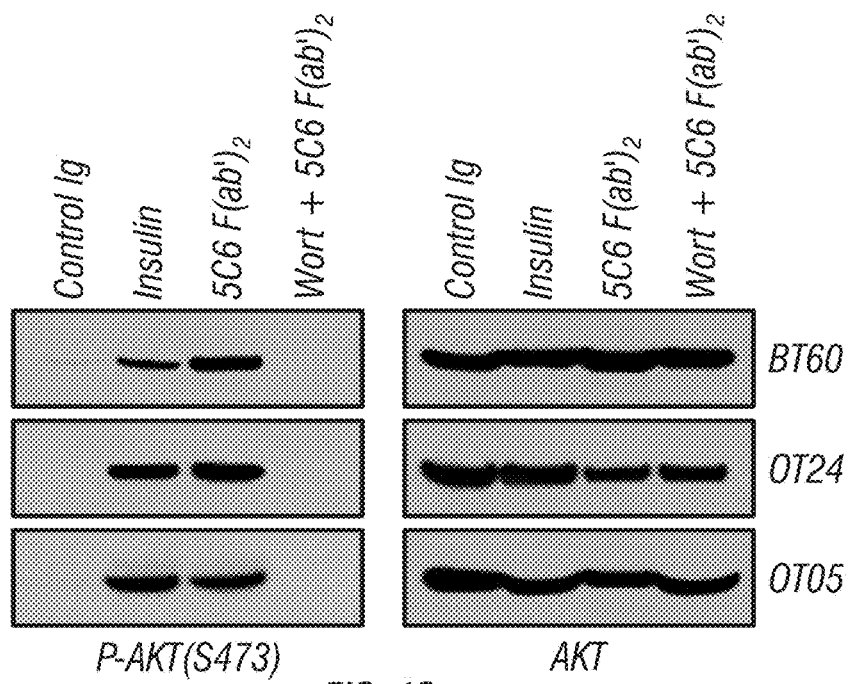
Figure 1F:
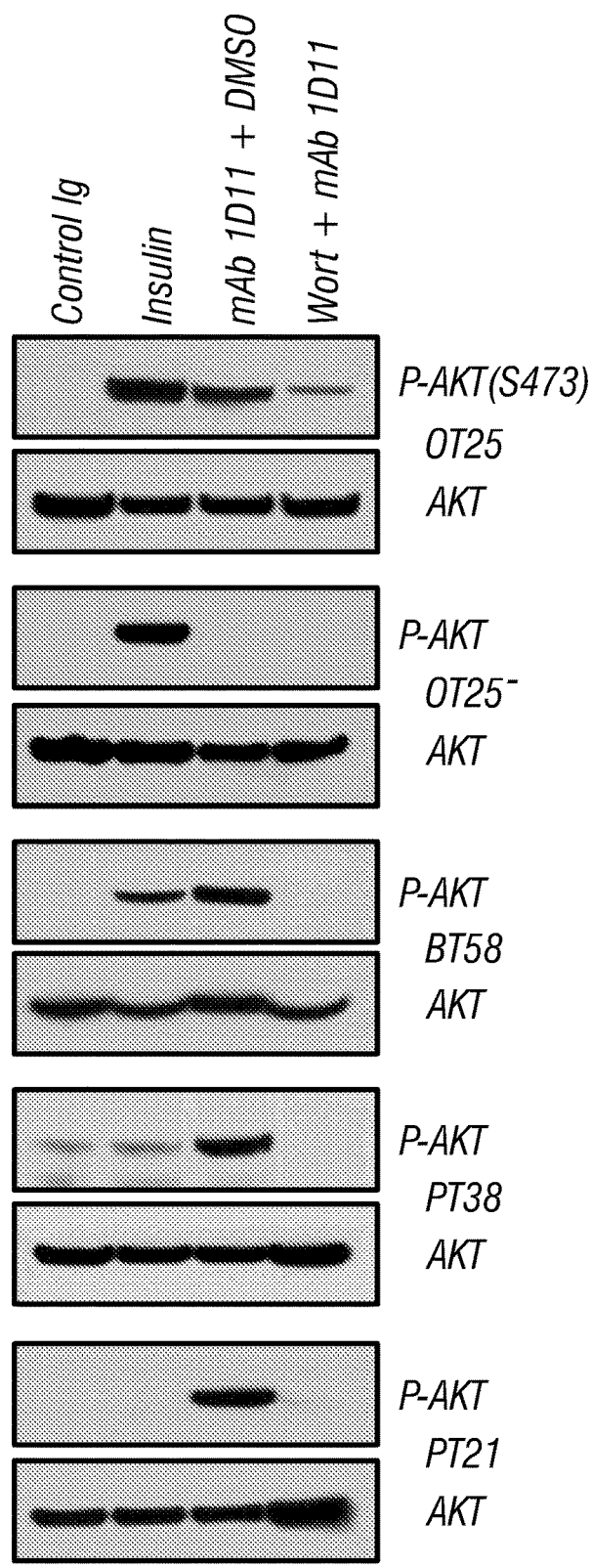

These findings gave rise to the idea that cancer cells might co-opt expression of NKG2D to exploit the presence of its ligands for self stimulation of tumor growth. In NK cells and T cells, phosphorylation of DAP10 activates branched signaling cascades that include the PI3K-AKT axis (Wu et al., 1999; Upshaw and Leibson, 2006; Sutherland et al., 2002)). The inventors tested the signaling capacity of NKG2D-DAP10 in sorted EpCAM+CD45− breast, ovarian, and prostate cancer cells after serum deprivation by 1D11 mAb-mediated receptor crosslinking and subsequent Ab probing of total cell lysate immunoblots for phosphorylation of AKT (Wan and Helman, 2003). Phospho-AKT (P-AKT) was induced in all of the four cancer samples tested but not in matched ovarian cancer cells sorted for absence of surface NKG2D. Its appearance was sensitive to wortmannin and thus dependent on PI3K (FIG. 1F) (Wu et al., 1999; Wan and Helman, 2003). Exposure to insulin provided for positive control activation except for the unresponsive prostate cancer cells. Crosslinked F(ab')2 fragments of the anti-NKG2D 5C6 mAb were also effective in P-AKT induction, thus precluding Ab Fc region/Fc receptor-mediated or unspecific stimulatory events (FIG. 1G).

Example 4

Minimal NKG2D-DAP10 Expression is Sufficient for AKT Activation in Tumor Lines

A thorough investigation of NKG2D-DAP10 signaling and its physiological effects required serial analyses and approaches for which ex vivo cancer cells were unsuitable. The inventors thus switched to studying tumor lines. However, unlike cancer cells, 15 breast, colon, gastric, ovarian, and prostate tumor lines tested by flow cytometry were either negative for surface NKG2D or displayed only minor fluorescence intensity profile shifts. No increased expression was apparent after treatment of cells with inhibitors of proteasomal or lysosomal degradation, or after exposure to IL-15, which induces T cell NKG2D (Groh et al., 2002; Meresse et al., 2004; Roda-Navarro and Reyburn, 2009). By real-time quantitative PCR (qPCR), 12 randomly selected tumor lines contained an average of no more than one copy of NKG2D and DAP10 mRNA per cell. In comparison, five freshly prepared NKG2D+EpCAM+CD45− cancer cell suspensions contained averages of 15 and 100 copies of NKG2D and DAP10 mRNAs, respectively. Nonetheless, with a subset of tumor lines (breast MCF-7, BT-20, and MDA-MB-453; ovarian HTB-78; colon DLD-1; and gastric AGS) chosen because of low constitutive AKT phosphorylation, PI3K-dependent induction of P-AKT was readily observed after desensitization of cells and 1D11 mAb- or 5C6 F(ab')2-mediated NKG2D crosslinking (FIG. 2A).

These results implying functional NKG2D-DAP10 expression were difficult to reconcile with the minimal expression of the corresponding mRNAs. However, the mRNAs may be unevenly distributed among tumor cells and template multiple translation cycles. In fact, protein expression of NKG2D-DAP10 was detected when lysates of large numbers of cells (~5×10$^7$ per SDS-PAGE lane; with cancers, the inventors used ~3-5×10$^6$ cells) were used in immunoprecipitation and immunoblot experiments employing highly sensitive chemiluminescent reagent (FIG. 2B). Altogether, these results indicate that few receptor complexes are sufficient for signal transduction in tumor lines, possibly due to their sensitized activation status. As exemplified by the CTLA-4 negative regulator of T cell activation, flow cytometry can be insufficiently sensitive to detect minimal expression of functionally active cell surface receptors (Krummel and Allison, 1996).

Complementary evidence was obtained with the breast MDA-MB-231, prostate PC3, and melanoma A375 tumor lines that lacked detectable NKG2D-DAP10 complexes and showed no inducible AKT phosphorylation (FIGS. 2 A and B). Altogether, these experiments with tumor lines replicated the results obtained with freshly isolated cancer cells, except for the much lower expression of NKG2D-DAP10.

Figure 5A:
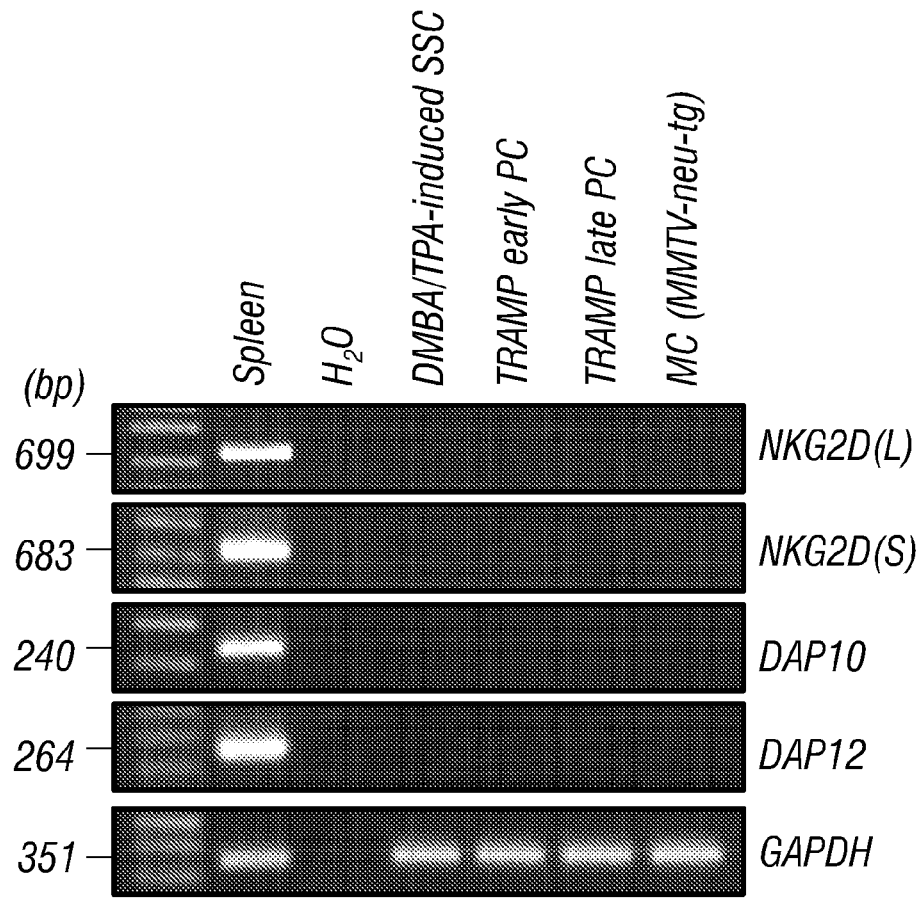
FIG. 5A-B. Absence of NKG2D receptors in mouse cancer cells. (A) Absence of NKG2D(L), NKG2D(S), DAP10, and DAP12 mRNAs in T cell and NK cell-depleted mouse DMBA/TPA-induced squamous cell carcinoma (SSC), TRAMP model early and late arising prostate cancers (PC), and HER-2/neu tg-induced mammary carcinoma (MC). Mouse spleen serves as positive control. (B) Absence of NKG2D protein in lysates of the cancer cells. Ba/F3 cell transfectants expressing mouse NKG2D-DAP10 serve as positive control.
Figure 5B:
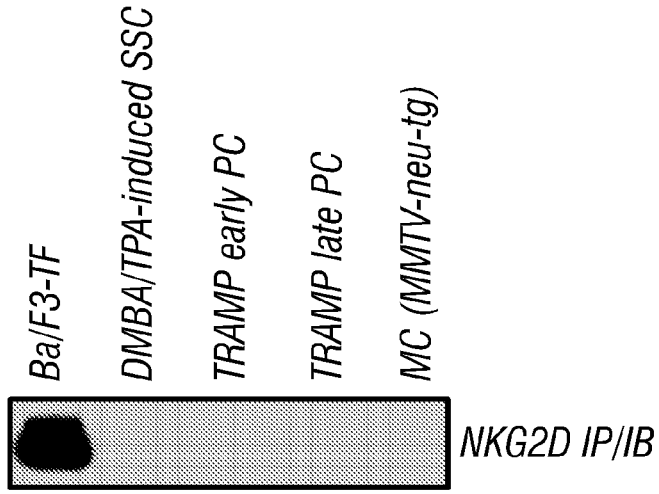

The inventors also tested for expression of NKG2D receptors in mouse cancer specimen including DMBA/TPA carcinogen-induced squamous cell carcinoma, TRAMP model aggressive and late-arising autochthonous prostate cancers, and HER-2/neu-transgenic mammary carcinoma (Guy et al., 1992; Gingrich et al., 1997; Kemp, 2005). By RT-PCR, all T cell and NK cell-depleted cancer cell samples were devoid of both the long and short variants of murine NKG2D and its DAP10 and DAP12 signaling adaptors (Gilfillan et al., 2002) (FIG. 5A). No NKG2D receptor protein was detected in lysates of each 5×10$^6$ cancer cells by immunoprecipitation with bead-coupled Ab and immunoblot (FIG. 5B). It thus appears that NKG2D receptor expression does not occur in mouse models of cancer.

Example 5

Genetic Confirmation of NKG2D-DAP10 Signaling in Tumor Cells

Figure 6A:
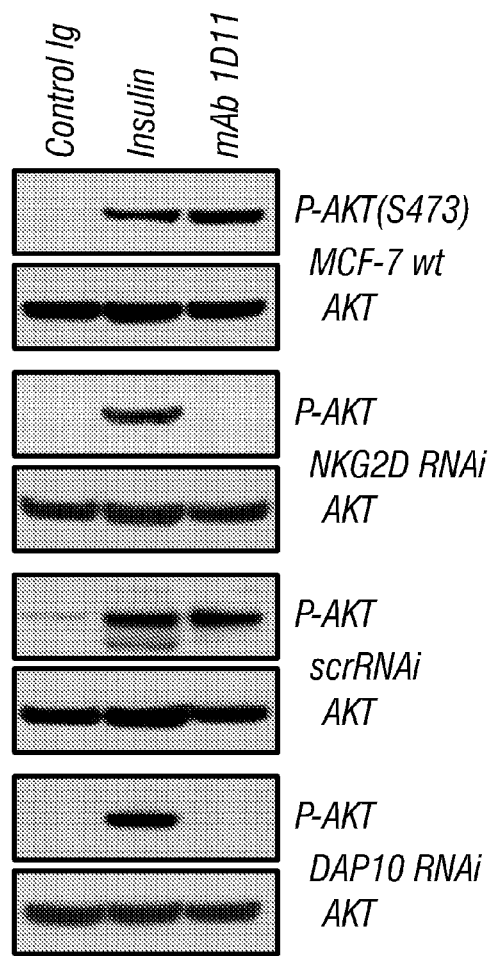
FIG. 6A-D. Genetic confirmation of NKG2D-DAP10 signaling in tumor cells. (A) Absence of inducible AKT (S473) phosphorylation in MCF-7 cells transduced with recombinant lentiviruses directing the expression of siRNAs targeting NKG2D or DAP10. Wild-type (wt) and scrambled NKG2D RNAi (scrRNAi)-transduced cells are shown as controls. (B) NKG2D immunoprecipitations using bead-coupled 5C6 mAb from lysates of siRNA-transduced MCF-7 cells ($5 \times 10^7$ per lane) and MCF-7-TF cells ($5 \times 10^6$ per lane) followed by immunoblot detection (panels at left). Panel at right shows DAP10 immunoblots using MCF-7-TF cells transduced with DAP10 siRNA. Bottom panels show actin immunoblot controls. (C) Flow cytometry of MCF-7-TF and MCF-7-TF-NKG2D RNAi cells for surface NKG2D. Mock transfectants and scrRNAi-transduced cells serve as controls. (D) Immunoblots showing depletion of NKG2D and DAP10 in CD8 T cells ($2 \times 10^6$ per lane) transduced with the targeting or scrambled control siRNAs.
Figure 6B:
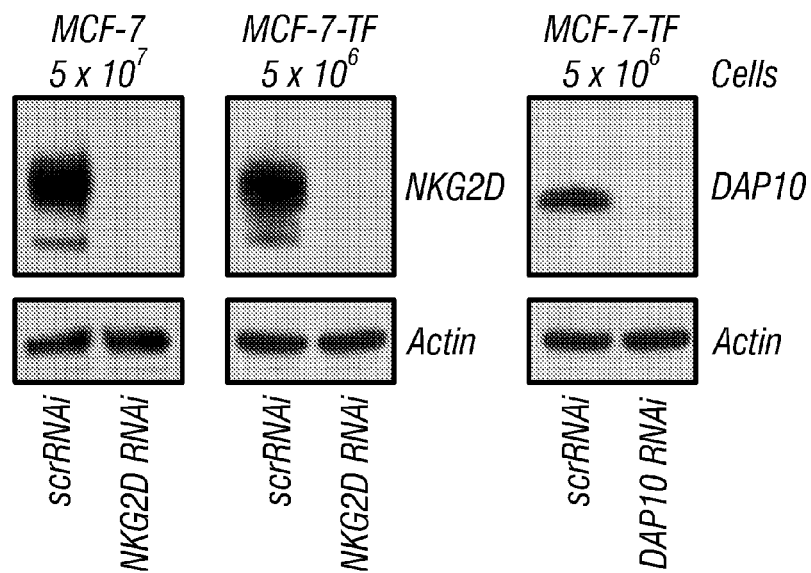
Figure 6C:
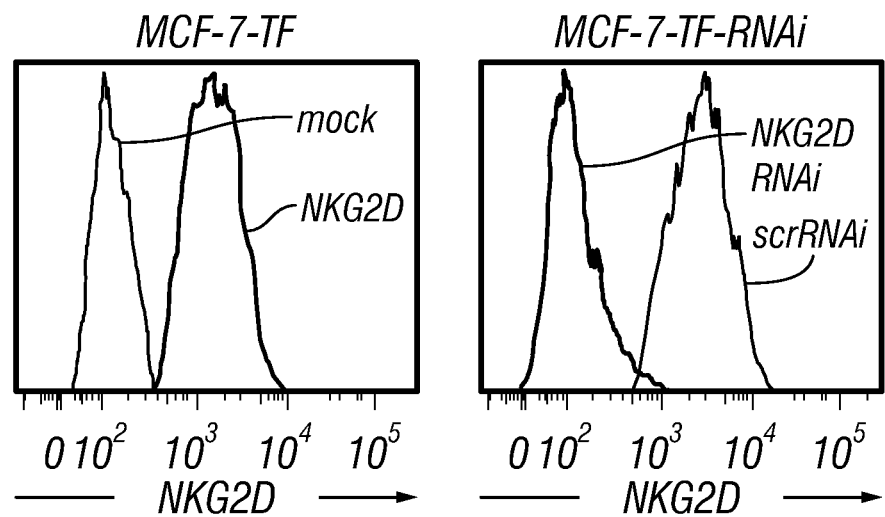
Figure 6D:
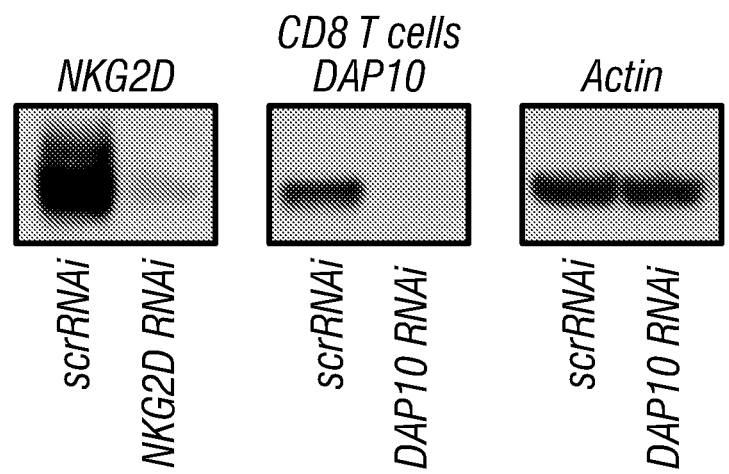

Since tumor cell expression and signaling proficiency of NKG2D-DAP10 may have profound implications, the inventors sought definitive experimental proof. Ectopic expression of NKG2D-DAP10 in stable transfectants of the A375 melanoma line (A375-TF cells) restored PI3K-dependent AKT phosphorylation after Ab-mediated receptor crosslinking (FIGS. 1 A and B). In a complementary approach, lentiviral transduction of siRNAs in breast tumor MCF-7 cells linked NKG2D and DAP10 depletion to loss of inducible AKT phosphorylation (FIG. 6A). Demonstration of protein depletion, as done for NKG2D (FIG. 6B), was not feasible for DAP10 since the DAP10 siRNA-transduced MCF-7 cells proliferated poorly and could not be expanded to the required ~5×10$^7$ cells. Hence, the inventors used NKG2D-DAP10 MCF-7 cell transfectants (MCF-7-TF cells) and a CD8 T cell line to fully demonstrate the efficacy of RNAi targeting of NKG2D and DAP10 (FIG. 6 B-D). Altogether, these results confirmed the signaling capacity of NKG2D-DAP10 in tumor cells.

Example 6

Figures 3A, 3B:
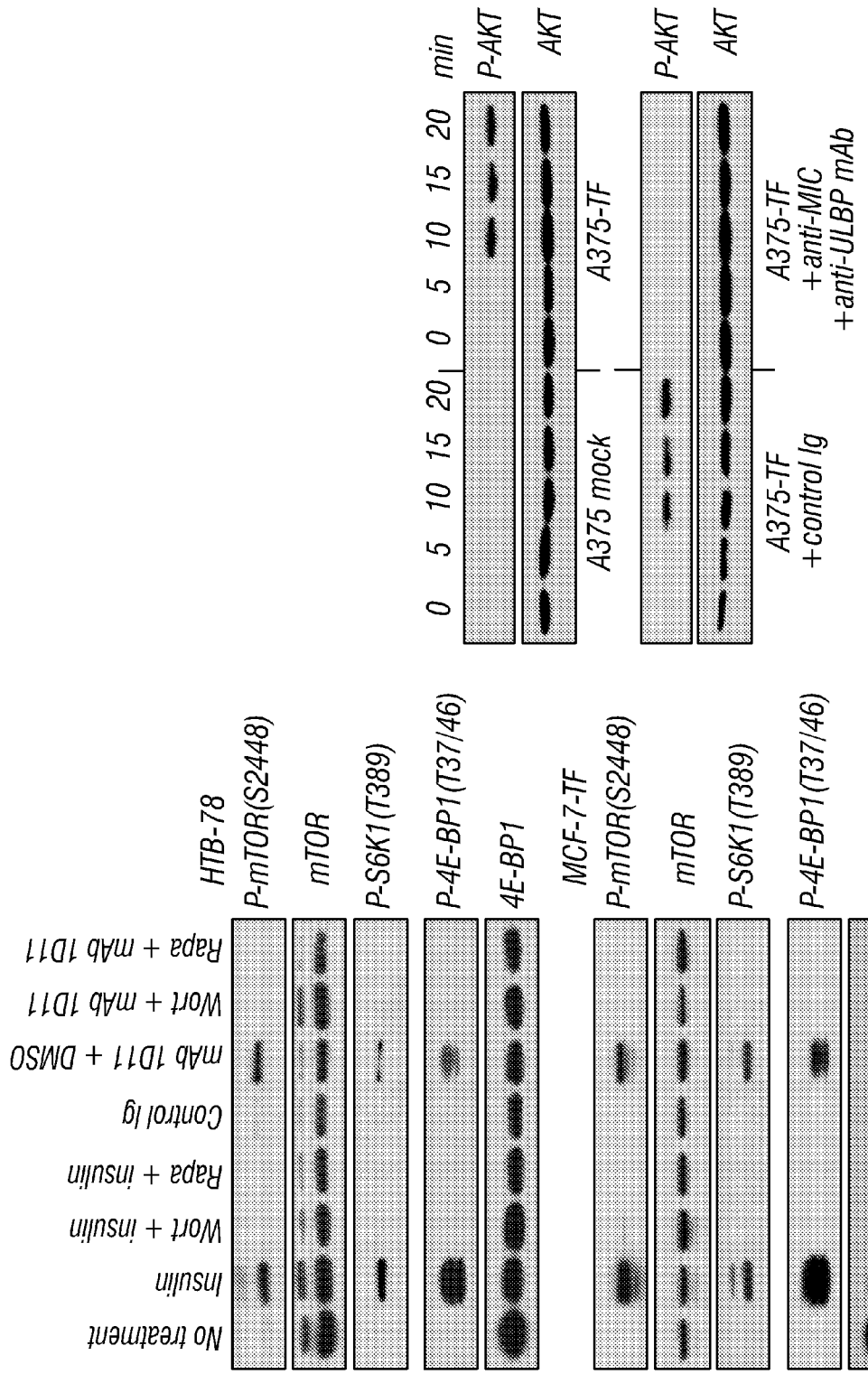
FIG. 3A-F. Activation of mTOR-S6K1/4E-BP1 and MAP kinase cascades. (A) Immunoblot detection of P-mTOR (S2448), P-S6K1(T389), and P-4E-BP1(T37/46) in lyates of HTB-78 and MCF-7-TF cells after starvation and mAb 1D11 crosslinking. Phosphorylation events are sensitive to both wortmannin (wort) and rapamycin (rapa). Insulin provides for positive control activation. Ig control lanes are as in FIG. 2. DMSO is added as solvent control. (B) Induction of P-AKT after 10 min in pellets of A375-TF but not mock-transfected A375 cells, and inhibition by anti-MIC/ULBP mAb cocktail. (C) Immunoblot detection of P-ERK1/2(T202/Y204) and P-JNK1/2(T183/Y185) in lysates of desensitized EpCAM+CD45-ovarian cancer (OT63), and HTB-78 and MCF-7-TF cells after exposure to recombinant sMICA and crosslinking anti-His tag Ab. EGF provides for positive control activation. U0126 and SP600125 are inhibitors of MEK/ERK and INK, respectively. Phosphorylation of ERK but not JNK is sensitive to wortmannin. (D) Immunoprecipitation of DAP10 and immunoblot detection of transiently associated Grb2 in lysates of MCF-7-TF cells ($5 \times 10^7$ cells per SDS-PAGE lane) after 2 or 5 min of Ab-mediated NKG2D crosslinking. (E) Induction of P-ERK1/2 in pellets of A375-TF cells and inhibition by anti-NKG2D ligand Ab cocktail as in (B). (F) Induction of P-JNK1/2 in pellets of A375-TF cells and inhibition by anti-NKG2D ligand Ab cocktail.

Activation of Mammalian Target of Rapamycin Downstream Effectors and Evidence for Self Stimulation The growth factor-responsive PI3K-AKT signal transduction pathway regulates intersecting cellular processes including cell-cycle progression, metabolic activity, and survival, and is commonly hyperactive in cancer (Vivanco and Sawyers, 2002). To further evaluate the proficiency of NKG2D-DAP10 signaling in tumor cells, the inventors examined activation of the mTOR kinase downstream of AKT and its catalytic activity on effectors controlling protein synthesis and cell growth, the ribosomal protein S6 kinase 1 (S6K1) and the translation initiation factor 4E-binding protein 1 (4E-BP1) (Ruggero and Sonenberg, 2005; Guertin and Sabatini, 2007). Along this axis, mTOR is part of the rapamycin-sensitive mTORC1 complex, which is separately activated by nutrient supply. The detection of target phosphorylation events following NKG2D crosslinking thus necessitated extensive prior cell starvation in serum-free medium and HBSS for 24 and a minimum of 4 h, respectively, to sufficiently reduce constitutive activation (Wang et al., 2003). Under these conditions, freshly isolated cancer cells and most tumor lines became unresponsive to NKG2D triggering due to impaired viability and probable loss of the scarcely expressed receptor proteins, respectively. However, with MCF-7-TF cells, which were comparable to ex vivo cancer cells in surface NKG2D expression (FIGS. 1C and S2C), and the HTB-78 ovarian tumor line, the inventors recorded robust induction of phosphorylation of mTOR, S6K1, and 4E-BP1 (FIG. 3A). The appearance of the phosphoproteins was both PI3K-dependent and rapamycin-sensitive. Thus, these results provided evidence for the capacity of NKG2D-DAP10 to stimulate the oncogenic PI3K-AKT-mTOR-S6K1/4E-BP1 signaling axis in tumor cells. By inference from this example, other effectors coupled to AKT signal transduction that promote cell cycle progression, differentiation, and survival are likely to be affected by NKG2D-DAP10 as well.

Figure 7:
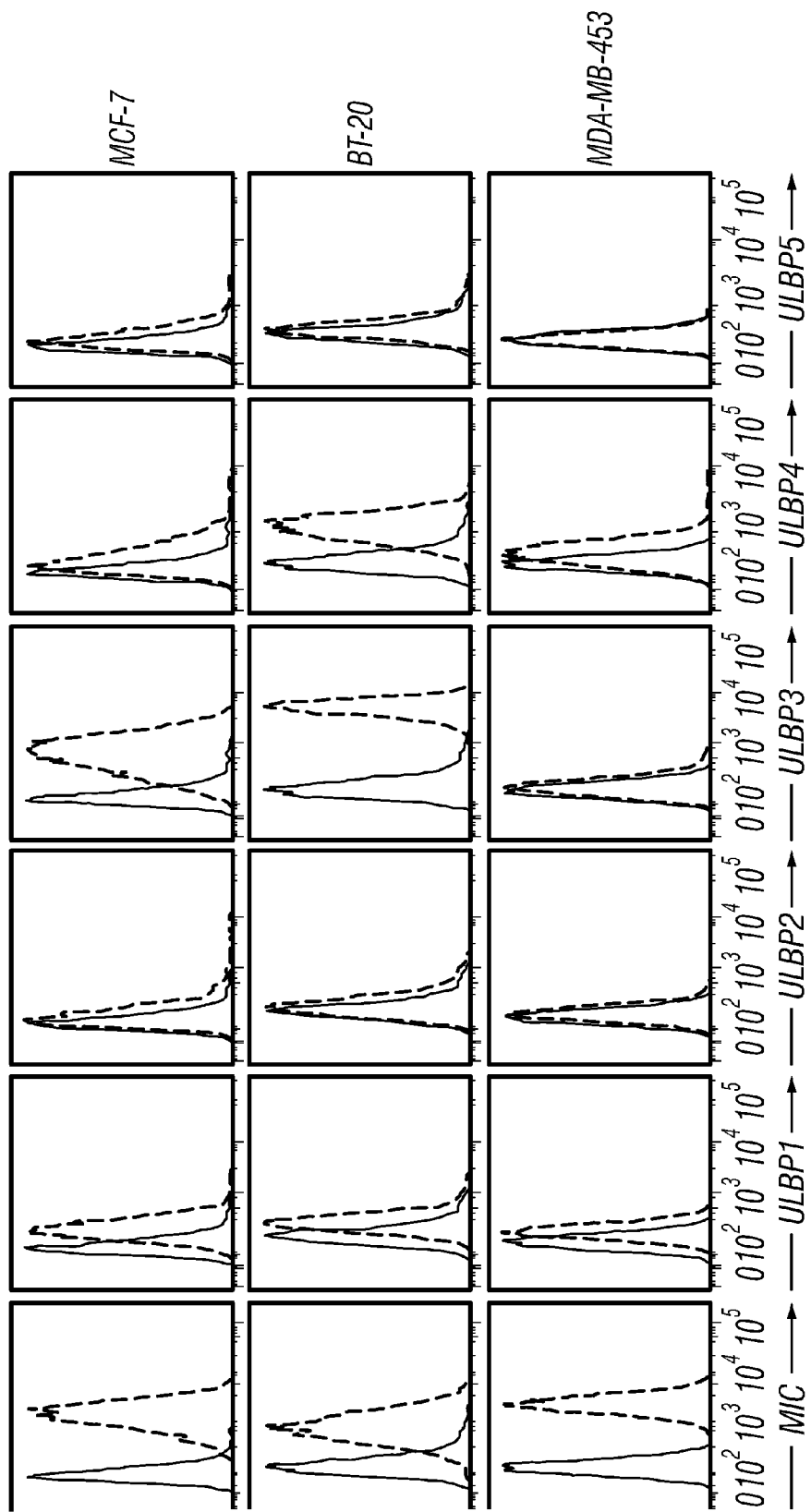
FIG. 7 Flow cytometry profiles of tumor lines stained for NKG2D ligands MIC and ULBP1-5.
Figure 7:
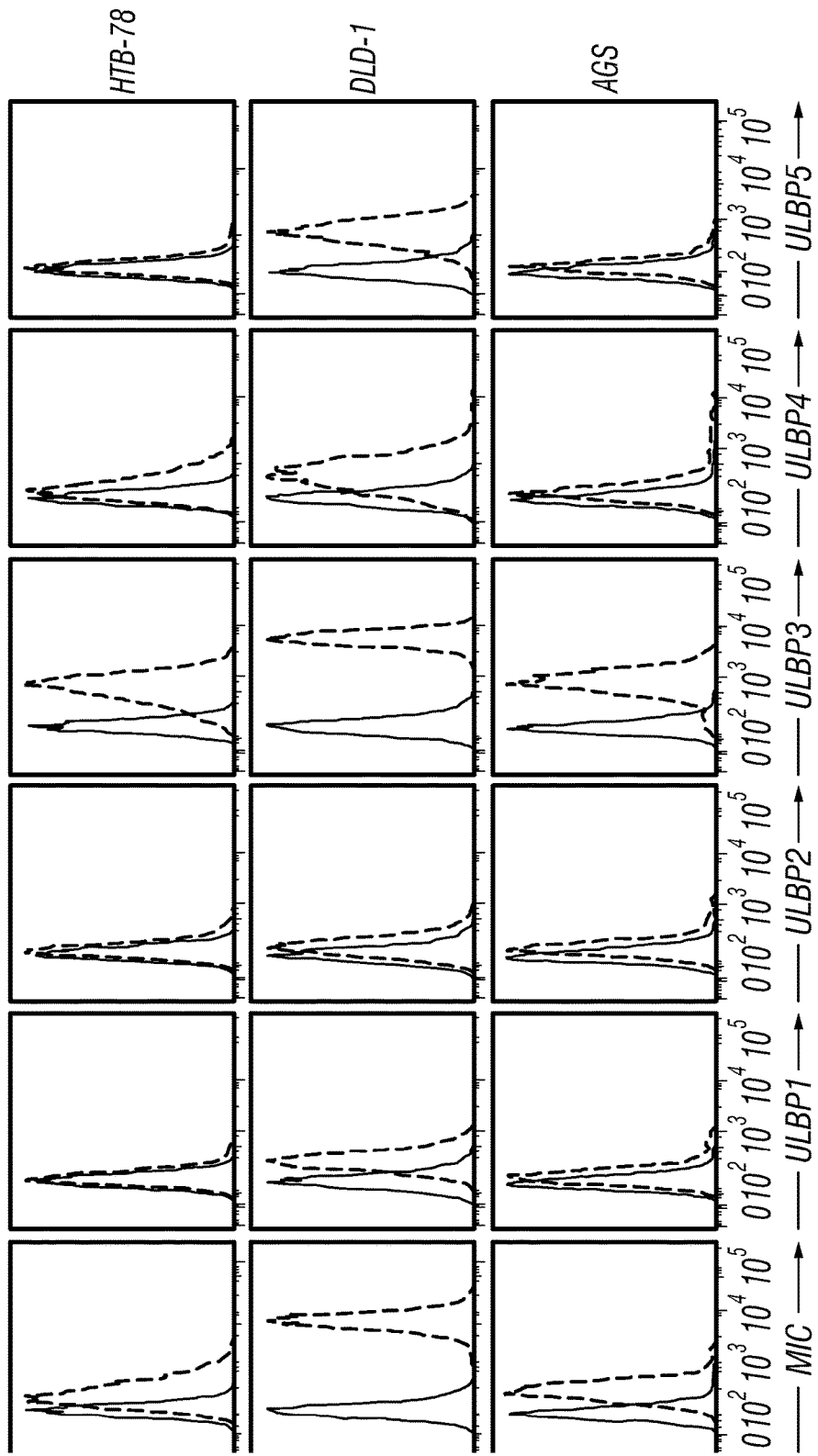
Figure 7:
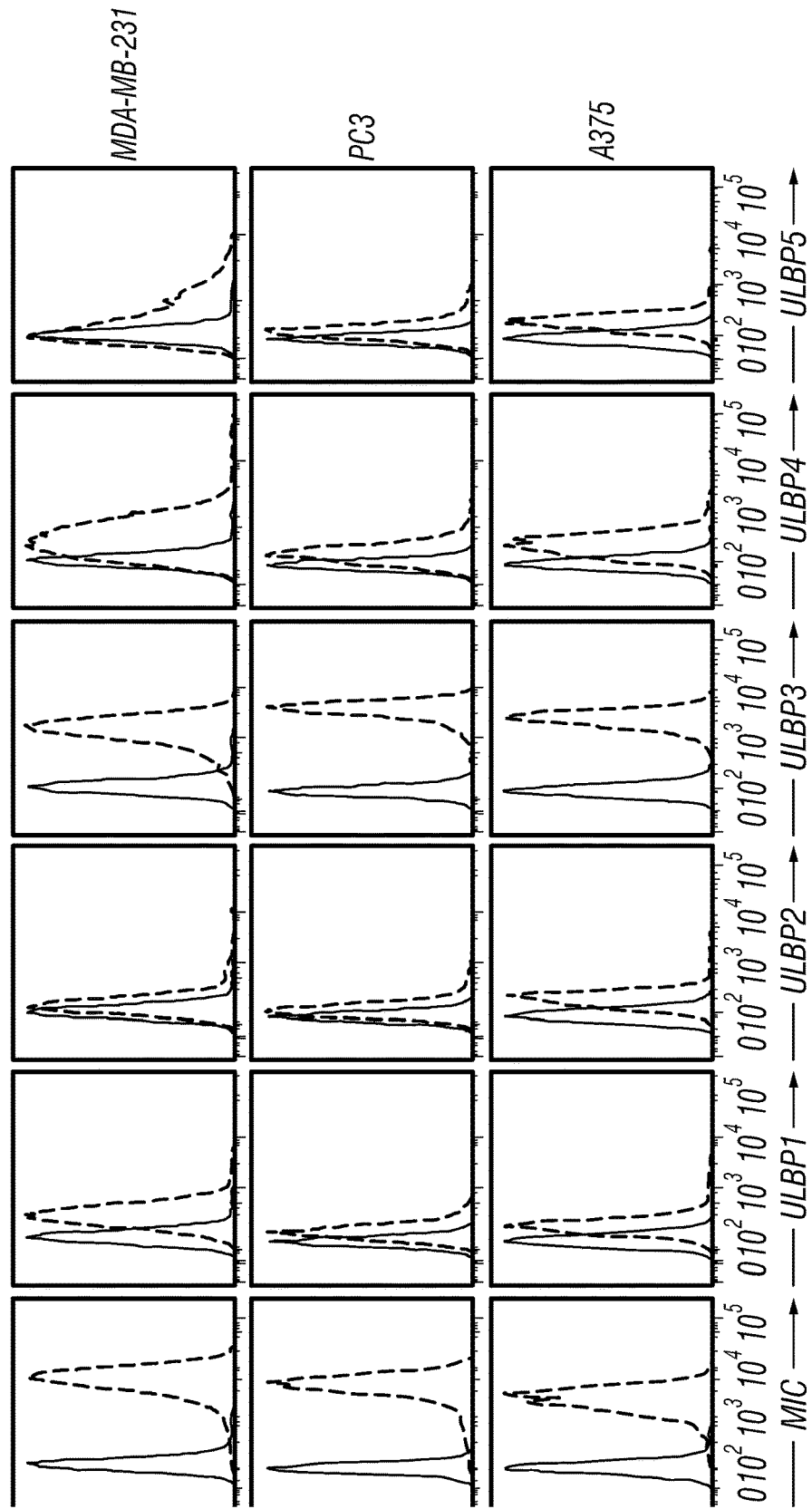

For the signaling experiments throughout this study, cells were typically grown at low density to minimize NKG2D ligand-mediated self stimulation. However, this functional activity was yet unproven although it was central to the model of the biological significance of tumor expression of NKG2D. To obtain evidence for self stimulation, the inventors examined P-AKT induction in a time-course experiment comparing desensitized A375 mock-transfected control (NKG2D-DAP10−) and A375-TF cells (NKG2D+DAP10+) that were spun into pellets to enforce cell contacts mimicking solid cancer cell compaction. Similar to the other tumor lines, A375 melanoma cells are positive for several NKG2D ligands (FIG. 7). Whereas no signal increase occurred in the negative control cells, P-AKT was induced in A375-TF cells after 10 minutes of incubation. This activity was blocked in the presence of a cocktail of anti-MIC and anti-ULBP mAb (Groh et al., 2006), thus reflecting productive NKG2D receptor-ligand interactions (FIG. 3B).

Example 7

Activation of ERK and JNK Map Kinases

Figure 3C:
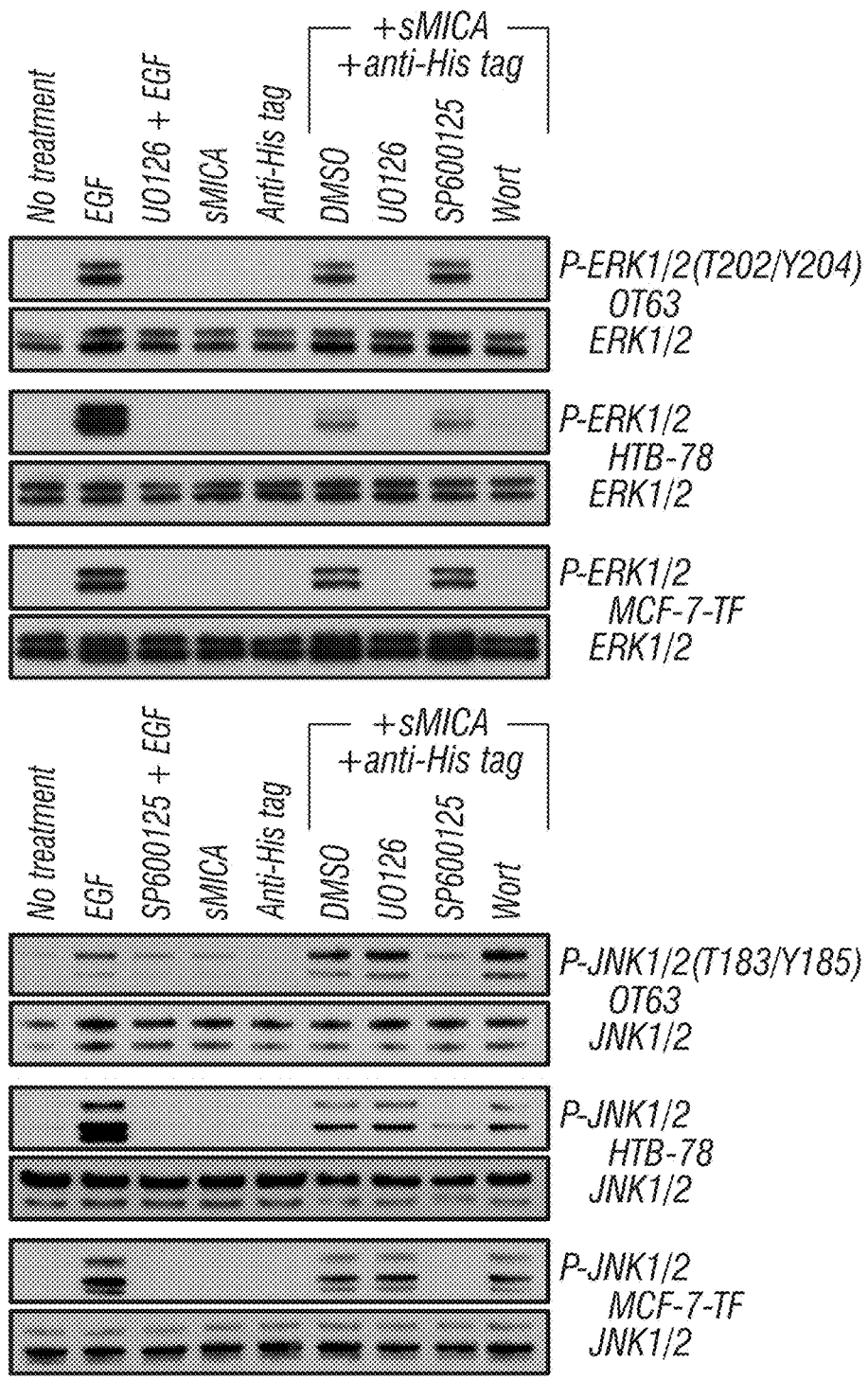
Figure 3D:
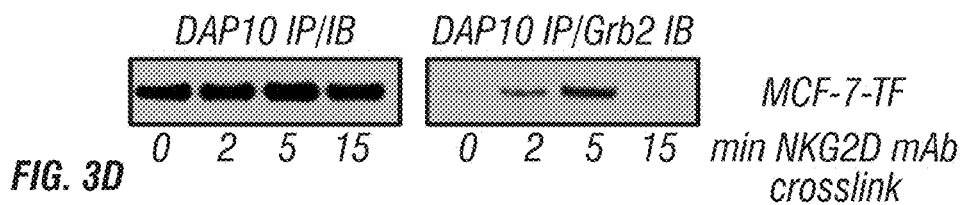
Figure 3E:
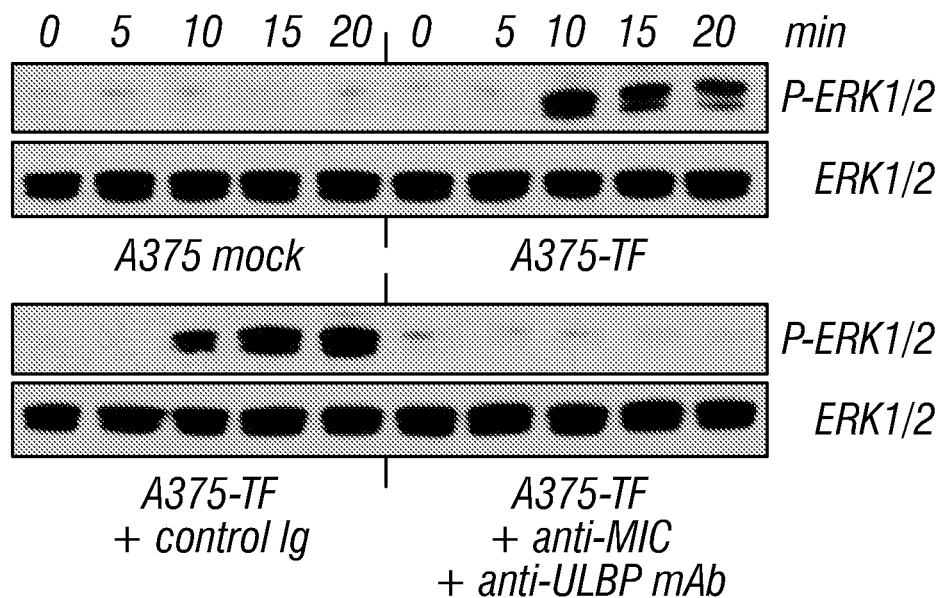
Figure 3F:
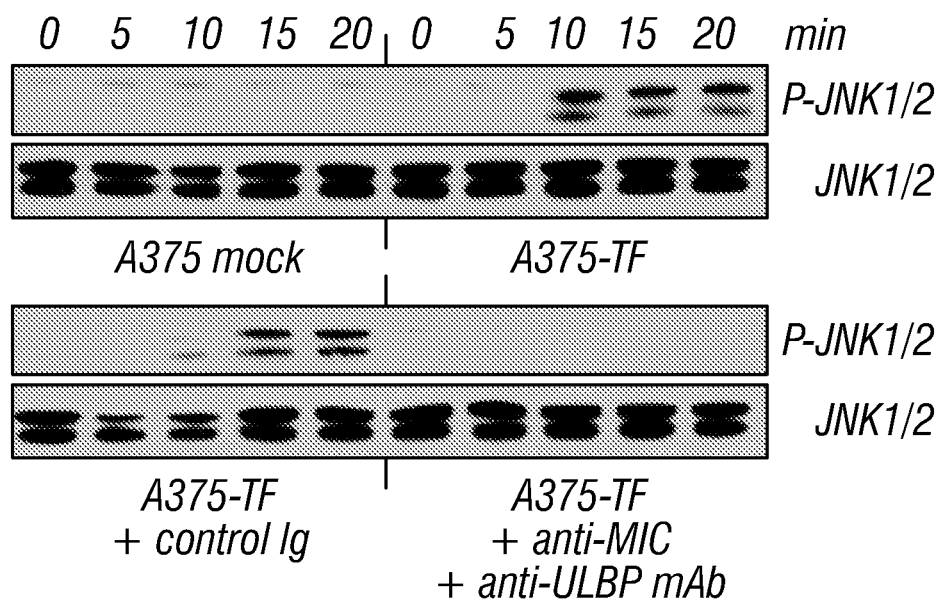

As determined so far, signaling pathway activation by NKG2D-DAP10 in tumor cells was similar to lymphocytes. In activated human NK cells and T cells, signal transduction initiated by PI3K also leads to phosphorylation of ERK, whereas alternative coupling of DAP10 to Grb2 results in phosphorylation of JNK (Upshaw and Leibson, 2006; Lanier, 2008; Segovis et al., 2009). In cancer cells, these MAP kinases are activation targets of the EGF receptor (EGFR) among other receptor Tyr kinases, which, due to mutation or aberrant expression, frequently cause excessive tumor cell proliferation and increased motility and survival (Normanno et al., 2006). To test the relevance of these pathways for NKG2D-DAP10 signaling in tumor cells, the inventors used freshly isolated EpCAM+CD45− ovarian cancer cells, and HTB-78 and MCF-7-TF cells that were desensitized and stimulated with recombinant soluble MICA (sMICA) crosslinked by anti-His tag Ab. As with the EGF control activation, stimulation of NKG2D-DAP10 resulted in phosphorylation of the ERK1/2 and JNK1/2 isoforms as determined by immunoblot using phosphoprotein-specific Abs (FIG. 3C). Tumor cell exposure to sMICA or anti-His tag Ab alone had no effect. The appearance of P-ERK1/2 and P-JNK1/2 was diminished by inhibitors of the MEK MAP kinase upstream of ERK (U0126) and JNK itself (SP600125), respectively, but not vice versa (FIG. 3C). P-ERK1/2 but not P-JNK1/2 was sensitive to wortmannin and thus, as in lymphocytes, dependent on PI3K (Lanier, 2008). Consequently, P-JNK1/2 was in all likelihood downstream of Grb2-Vav1. This arrangement was supported by immunoblot detection of Grb2 in transient association with DAP10, which was immunoprecipitated from lysates of MCF-7-TF cells after brief Ab-mediated NKG2D crosslinking (FIG. 3D). As with the tumor cell ligand-induced AKT phosphorylation (FIG. 3B), P-ERK1/2 and P-JNK1/2 were also detected in time course experiments with compacted A375-TF cells in the absence but not in the presence of ligand masking Ab cocktail (FIGS. 3 E and F).

Example 8

Stimulation of Cellular Proliferation and Bioenergetic Metabolism

Figure 4A:
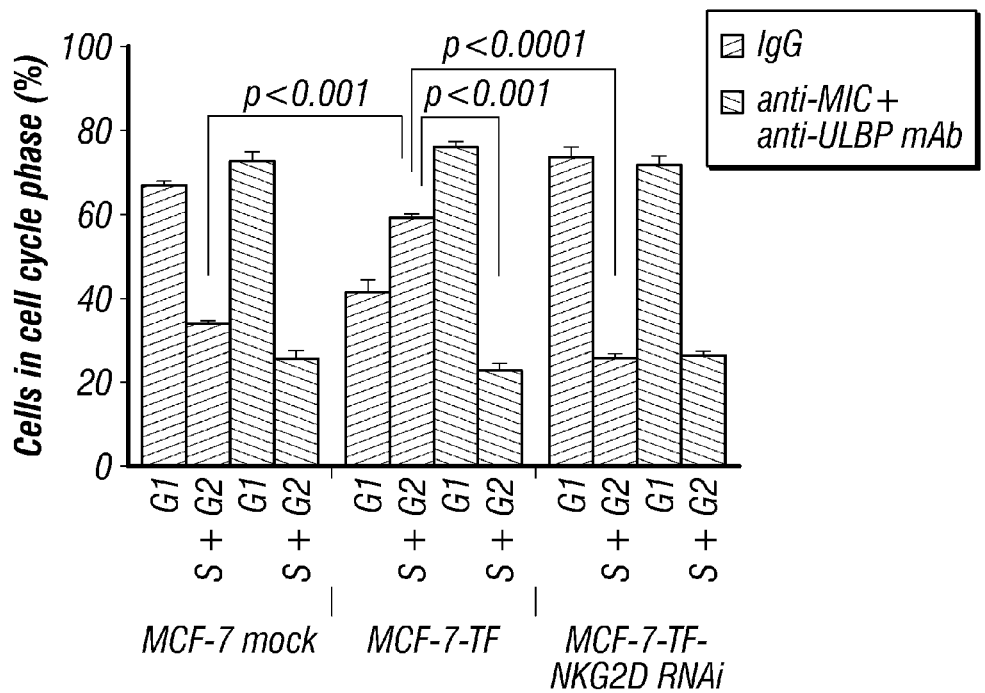
FIG. 4A-B. Stimulation of proliferation and bioenergetic metabolism. (A) Cell cycle analysis of MCF-7 mock, MCF-7-TF, and MCF-7-TF-NKG2D RNAi cells, plated for 24 h in the presence or absence of anti-MIC/ULBP1/3/4 Ab cocktail, by PI staining and quantitative evaluation of flow cytometry data based on Dean-Jett-Fox curve fitting. Data shown are representative of three experiments. P-values indicate statistical significance of data pair comparisons. (B) NKG2D-DAP10 signaling is associated with increased metabolic activity. MCF-7 mock control and MCF-7-TF cells were compared for total cellular ATP (bar graph at left), for real-time oxygen consumption (OCR; center bar graph), and for extracellular acidification rates (ECAR; bar graph at right). P-values indicate statistical significance. Data shown are representative of at least three experiments.
Figure 4B:
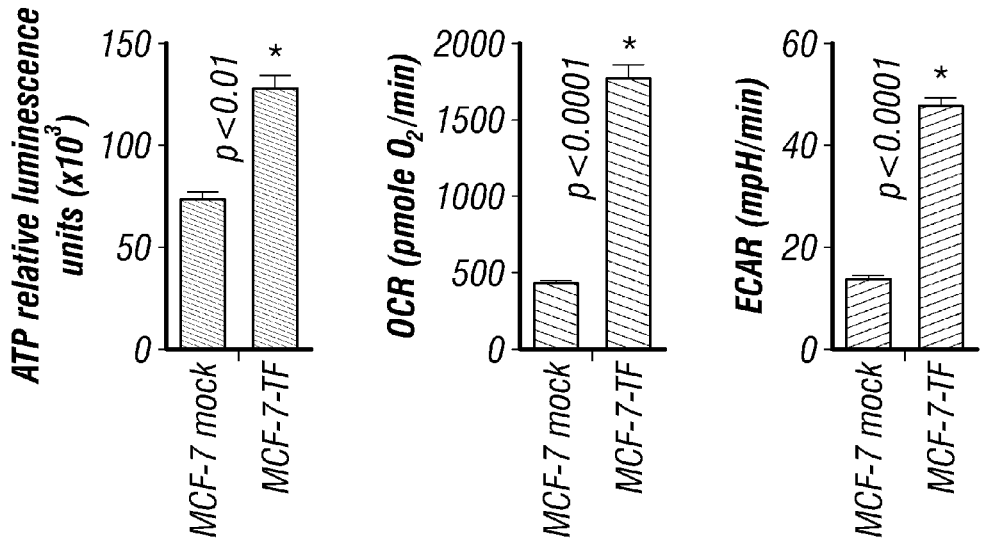

According to the analysis of representative components of signaling pathways associated with tumorigenesis, NKG2D-DAP10 displayed activities similar to growth factor receptors such as the EGFR and the insulin-like growth factor-1 receptor (IGF-1R) (Normanno et al., 2006; Pollak et al., 2004). The inventors thus explored effects on cellular functions resulting from NKG2D stimulation using the MCF-7 mock-transfected control and MCF-7-TF model cells. Cells were plated at near confluence in the absence of growth factors with or without the relevant anti-MIC and anti-ULBP1/3/4 Abs or control Ig 24 h before assay time (FIG. 7). Cell cycle analysis by propidium iodide (PI) staining identified significantly enlarged proportions of MCF-7-TF cells with DNA content corresponding to S and G2 phase transitions. This effect was reversed in the presence of the anti-NKG2D ligand Ab cocktail or by RNAi targeting of NKG2D (FIG. 4A). These results confirmed ligand-mediated NKG2D stimulation and were corroborated by determinations of cellular ATP as an independent parameter of cellular proliferation (FIG. 4B).

Changes in bioenergetic cell metabolism were measured using an extracellular flux analyzer that allows real-time determinations of oxygen consumption rates (OCR) and of extracellular acidification rates (ECAR) as a measure of glycolysis-derived lactic acid (Wu et al., 2007). Both energy producing pathways, oxidative phosphorylation and glycolysis, were markedly stimulated in MCF-7-TF cells (FIG. 4B). The inventors conclude that based on key criteria tested, in vitro stimulation of cellular proliferation and bioenergetic metabolism, NKG2D-DAP10 are functionally similar to tumor growth factor receptors.

Example 9

Correlation Between NKG2D Expression and Tumor Progression

To obtain evidence for pathophysiological significance of NKG2D expression in cancers, the inventors tested for clinical correlations. Pathology reports for all 60 primary cancer specimens examined were abstracted for clinical and histopathological information, and data on tumor size/ spread, lymph node involvement, and, where available, tumor metastasis used to generate AJCC (American Joint Committee on Cancer) staging (Table 2). To allow for a combined analysis of all four cancer types studied, the inventors applied TNM (tumor size/spread, node involvement, and metastasis status) rather than cancer type-specific staging. Survival/outcome information was not available. Linear regression analysis revealed significant correlations between mean percentages of NKG2D positive cancer cells (% 2D) with tumor stage [p<0.0001; Stage I (n=14), % 2D 3.7; Stage II (n=15), % 2D 10.9; Stage III (n=30), % 2D 28.3; Stage 1V (n=1), % 2D 45.7] and tumor size/spread [p<0.0001; T1 (n=12), % 2D 4.5; T2 (n=13), % 2D 6.3; T3 (n=34), % 2D 27.7; T4 (n=1), % 2D 34.0]. By t-test assessment, a statistically significant association was also observed with lymph node status [p<0.009; negative (n=33), % 2D 12.3; positive (n=18), % 2D 24.6). There were no statistically significant associations with tumor grade (p=0.025), presence or absence of lymphatic and/or vascular invasion (p=0.10), or patient age (p=0.59). Altogether, these results provide ex vivo correlative evidence associating NKG2D expression with criteria of tumor progression, thereby lending support to its tumor growth factor receptor-like stimulatory functions.

Example 10

NKG2D-DAP10-Mediated Induction of EMT-Associated Changes

Inspection of MCF-7-TF cells by phase contrast microscopy revealed profound morphological changes in comparison to the mock-transfected control and wild-type cells with epithelial cobblestone-like shapes. MCF-7-TF cells were growing more dispersed and displayed spindle fibroblast-like shapes with migratory protrusions. These changes were due to above-threshold expression of NKG2D-DAP10 as RNAi targeting of NKG2D restored the parental cell morphology (FIG. 8A). These observations suggested that ligand-mediated stimulation of NKG2D resulted in activation of epithelial-mesenchymal transition (EMT), a reprogramming process causing changes of cell-cell and cell-matrix adhesion concurrent with acquisition of cell motility (Polyak and Weinberg, 2009; Thiery et al., 2009; Yilmaz and Christofori, 2009). Diagnostic of EMT, among other criteria, are reduced expression of E-cadherin and induction of N-cadherin (Polyak and Weinberg, 2009; Thiery et al., 2009;

TABLE 2

Clinical characteristics of cancer specimens included in statistical analysis

| | Breast carcinomas (n = 12) | Colon carcinomas (n = 14) | Prostate carcinomas (n = 4) | Ovarian carcinomas (n = 30) |
|---|---|---|---|---|
| AJCC Stage (pTNM) | | | | |
| I | 0 | 3 | 0 | 11 |
| II | 4 | 7 | 3 | 1 |
| III | 8 | 4 | 1 | 17 |
| IV | 0 | 0 | 0 | 1 |
| Tumor size/spread | | | | |
| T1 | 1 | 0 | 0 | 11 |
| T2 | 4 | 3 | 3 | 3 |
| T3 | 7 | 10 | 1 | 16 |
| T4 | 0 | 1 | 0 | N/A |
| Histology | ductal 1 lobular 3 unspecified 8 | adenocarcinoma 14 | adenocarcinoma 4 | serous 22 clear cell 2 transition 2 endometrioid 3 mucinous 1 |
| Tumor grade | | | | |
| G0 (non-malignant) | 0 | 0 | 0 | 1 |
| G1 (low) | 2 | 0 | 0 | 3 |
| G2 (intermediate) | 4 | 13 | 2 | 3 |
| G3 (high) | 5 | 1 | 2 | 23 |
| no data | 1 | 0 | 0 | 0 |
| Lymphatic/vascular invasion | | | | |
| no | 3 | 11 | 4 | 6 |
| yes | 6 | 2 | 0 | 8 |
| no data | 3 | 1 | 0 | 16 |
| Lymph node involvement | | | | |
| no | 2 | 10 | 4 | 17 |
| yes | 10 | 4 | 0 | 4 |
| no data | 0 | 0 | 0 | 9 |
| Distant metastasis | | | | |
| no | 0 | 0 | 0 | 2 |
| yes | 0 | 0 | 0 | 1 |
| no data | 12 | 14 | 4 | 27 |

Abbreviations: pTNM, pathology-based TNM staging. See text for explanations.

Yang and Weinberg, 2008). By IF microscopy and immunoblot, MCF-7-TF cells displayed those changes in epithelial and mesenchymal marker proteins, which were reversed by RNAi targeting of NKG2D (FIG. 8A, B). Among key transcription factors is SNAI1 and Twist, which were induced in MCF-7-TF as well as in MCF-10A-TF and SUM149PT-TF cells (FIG. 8C). MCF-7-TF cells also scored increased migratory and invasive activities in Matrigel assays (FIG. 8D). Both ERK- and AKT-initiated signaling have been implicated in cancer EMT (Thiery et al., 2009). These results thus support the concept that NKG2D-DAP10 contributes to the generation of migratory mesenchymal cells and thus to malignant cancer progression.

Example 11

Association of an E-Cadherin$^-$/N-Cadherin$^+$ Phenotype with NKG2D Expression Among Cancer Cells Formal demonstrations of cancer EMT, i.e., the complete aquisition of a mesenchymal phenotype with concurrent loss of epithelial traits in tumor environments, are contentious because of indistinguishable features shared by stromal cells. However, transitional stages with both epithelial and mesenchymal characteristics can be observed (Creighton et al., 2010; Logullo et al., 2010; Strauss et al., 2011). The inventors sought to identify an approximative in vivo correlate of the observations made with MCF-7-TF cells. Freshly isolated ovarian cancer cells gated for EpCAM+ and/or pan-cytokeratin+ and CD45− were analysed for E-cadherin and N-cadherin in relationship to surface NKG2D by flow cytometry (FIG. 8D). The results support associations of the E-cadherin−/N-cadherin+ phenotype with NKG2D+ cells, providing evidence that NKG2D represents an important inducer of EMT-like cellular changes.

Example 12

Evidence that NKG2D Promotes Survival

Increased NKG2D-DAP10 in MCF-7-TF cells decreased susceptibility to serum starvation-induced apoptosis and increased expression of the anti-apoptotic Bcl-2 (FIG. 9).

Example 13

NKG2D and EMT

Figure 11:
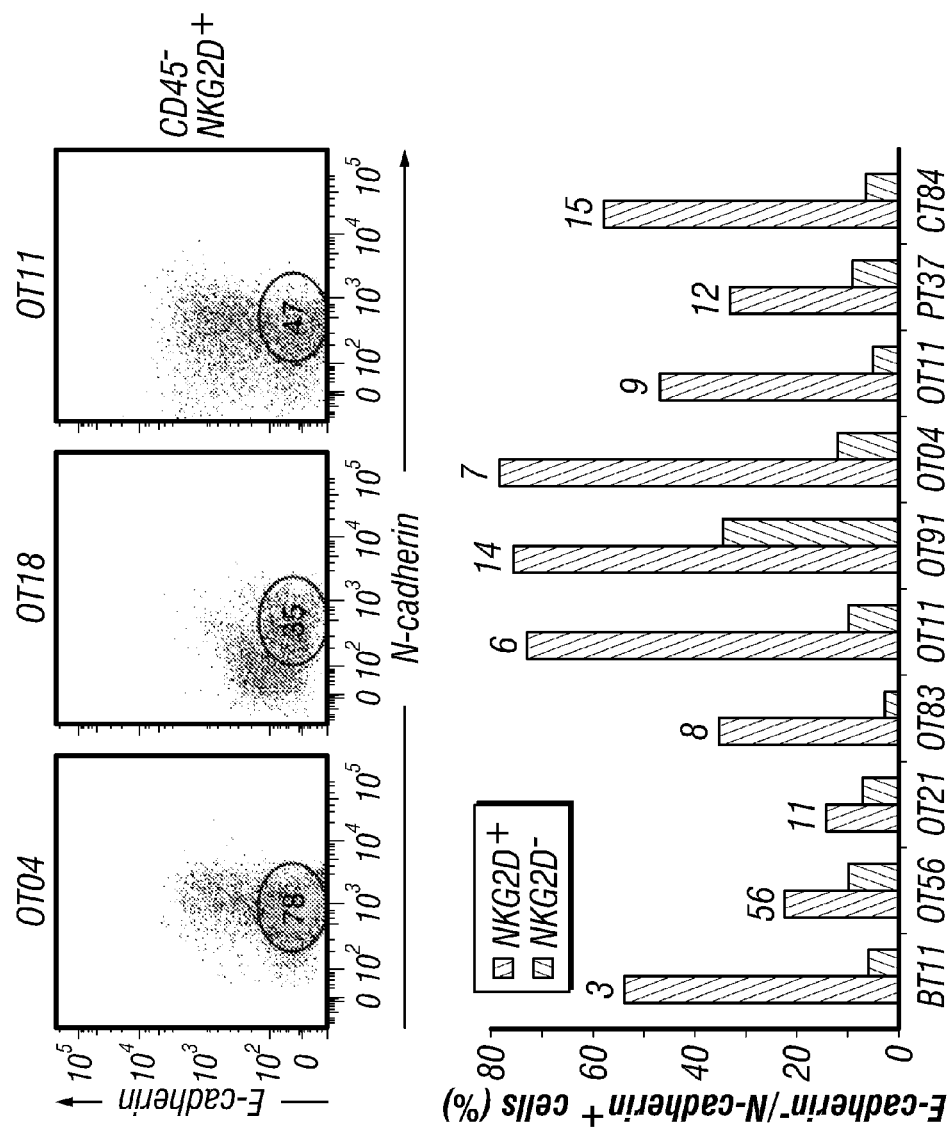
FIG. 11. Association of NKG2D Expression with EMT Markers in ex vivo Cancer Cells. Ex vivo analysis of freshly isolated ovarian cancer cell suspensions for markers associated with EMT by flow cytometry. Example flow dot plots are shown at the top. Bottom bar graph depicts results of analysis of larger sample number (BT, breast cancer; OT, ovarian cancer; PT, prostate cancer; CT, colon cancer). Cancer cell suspensions gated for EpCAM (or cytokeratin), absence of CD45 (marker for lymphocytes), and presence of NKG2D were stained for gain of E-cadherin and loss of N-cadherin as key markers associated with cancer cell EMT.

MCF-7 cells were evaluated for stimulation of cellular migration through porous filters and for invasion of reconstituted basement membranes in MATRIGEL assays (FIG. 10). Moreover, an association between NKG2D expression and EMT markers was observed in ex vivo cancer cells (FIG. 11).

Example 14

NKG2D Promotes Tumor Initiation, Growth and Dedifferentiation

Figure 12A:
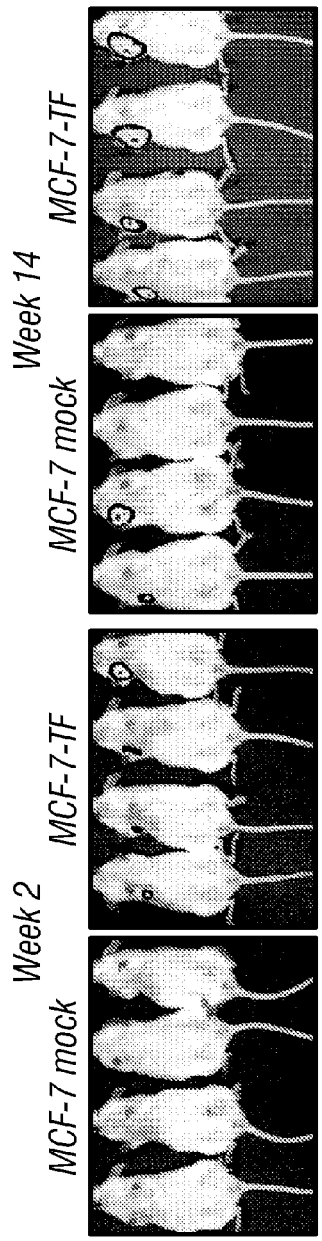
FIG. 12A-C. NKG2D promotes tumor initiation, growth and dedifferentiation. Luciferase expressing MCF-7 cells stably transduced with NKG2D-DAP10 (MCF-7-TF) or empty vector (MCF-7-mock) were injected into mammary fat pads of SCID mice. Tumor take and growth was monitored by in vivo imaging and external caliper. A, B, MCF-7-TF cell implants generated tumors as early as two weeks post xenotransplantation whereas control tumors took up to 8 weeks to develop. B, Tumor volumes of MCF-7-TF tumors were significantly larger than those of control tumors with significance remaining when tumor volumes were controlled for tumor appearance. Tumor weight, measured at 14 weeks post implantation, also revealed significant differences between NKG2D transfected and control tumors. C, By routine histopathology, MCF-7-TF tumors display irregular growth patterns, anisokaryosis (variations in nuclear size and shape) and multiple atypical cell divisions (marked by arrows) whereas control tumors are well encapsulated nodules composed of solid sheets and nests with regular nuclei and limited numbers of mitotic cells.
Figure 12B:
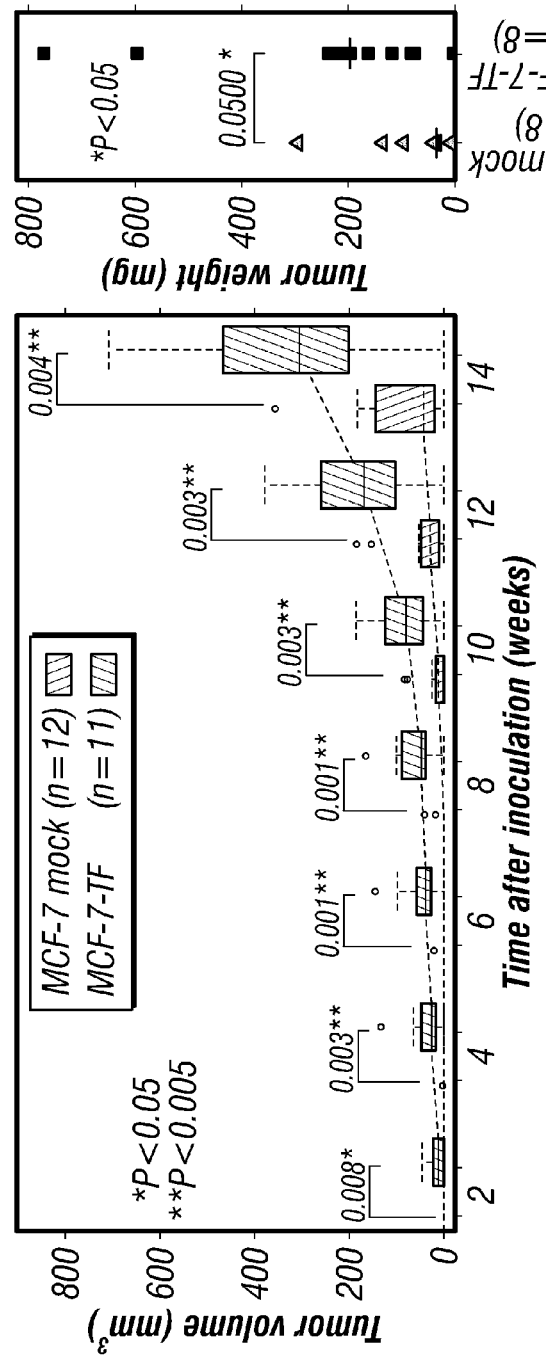
Figure 12C:
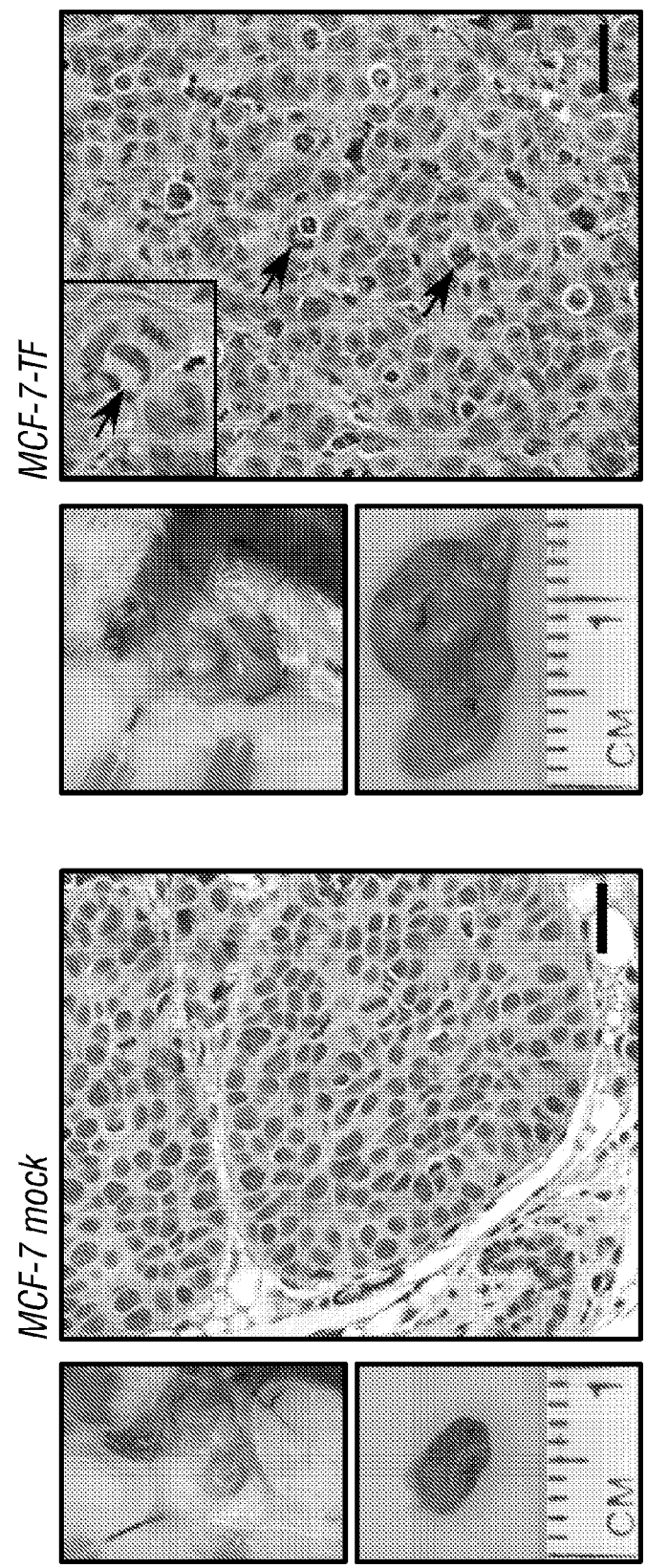

Luciferase expressing MCF-7 cells stably transduced with NKG2D-DAP10 (MCF-7-TF) or empty vector (MCF-7-mock) were injected into mammary fat pads of SCID mice. Tumor take and growth was monitored by in vivo imaging and external caliper. MCF-7-TF cell implants generated tumors as early as two weeks post xenotransplantation whereas control tumors took up to 8 weeks to develop. (FIG. 12A, B), Tumor volumes of MCF-7-TF tumors were significantly larger than those of control tumors with significance remaining when tumor volumes were controlled for tumor appearance. Tumor weight, measured at 14 weeks post implantation, also revealed significant differences between NKG2D transfected and control tumors. (FIG. 12B) By routine histopathology, MCF-7-TF tumors display irregular growth patterns, anisokaryosis (variations in nuclear size and shape) and multiple atypical cell divisions (marked by arrows) whereas control tumors are well encapsulated nodules composed of solid sheets and nests with regular nuclei and limited numbers of mitotic cells. (FIG. 12C)

Example 15

NKG2D Promotes Local Invasion, Intravasation and Distant Metastasis Formation

Figure 13B:
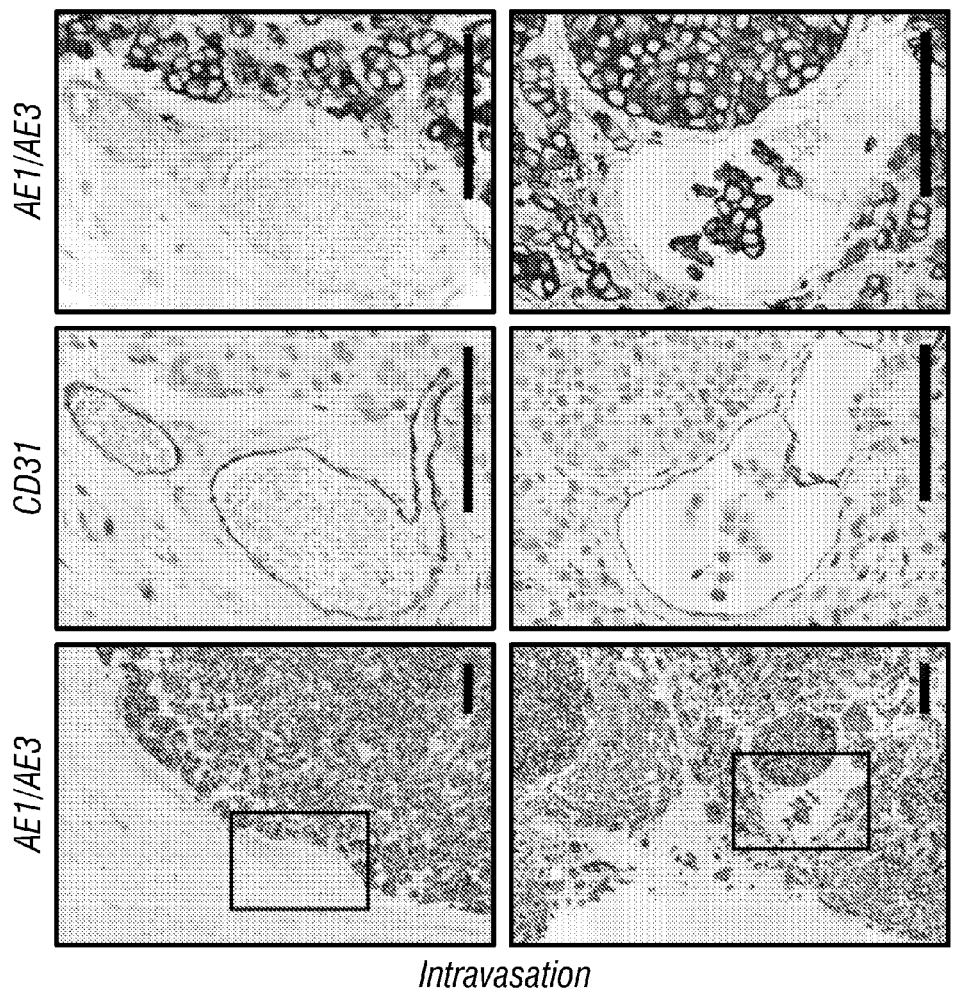
Figure 13A:
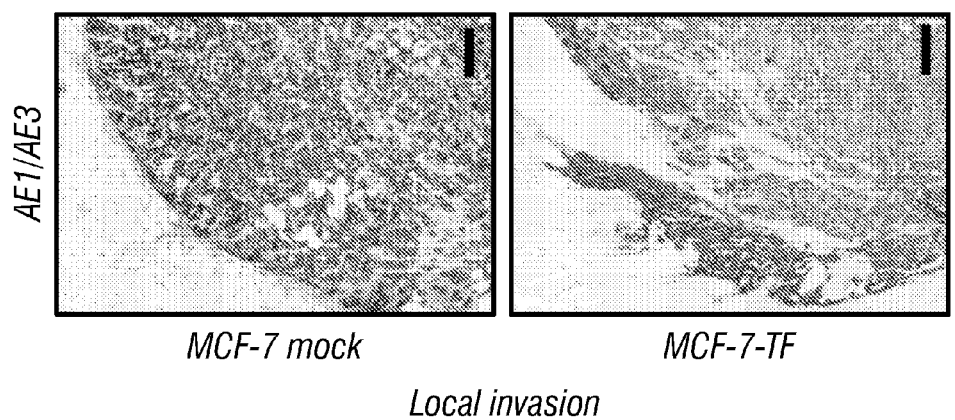

FIG. 13A-C, Images are derived from tumors harvested at week 8 post orthotopic transplantation. MCF-7 mock and -TF tumor cells are identified by immunohistochemical detection of human pan-cytokeratin using the AE1/AE3 antibody. In contrast to non-invasive control tumors confined within fibrotic capsules, MCF-7-TF tumors display irregular strands of tumor tissue dissociating from the primary tumor mass and invading adjacent stroma. (FIG. 13A) MCF-7-TF tumors display vascular invasion. (FIG. 13B) Small clusters of AE1/AE3 positive cells are localized within an intratumoral vessel identified by staining for the MECA-32 mouse endothelial cell-specific marker. Control vessels adjacent to MCF-7 mock tumors contain erythrocytes but no AE1/AE3 positive cells. Serial Hematoxilin and Eosin- (H&E) and AE1/AE3-stained lung section with clusters of metastatic cells within black squares. (FIG. 13C) Bioluminescence evidence of macro metastasis in lungs dissected from MCF-7-TF tumor but not control-tumor bearing mice. (FIG. 13D)

REFERENCES

The following references, to the extent that they provide exemplary procedural or other details supplementary to those set forth herein, are specifically incorporated herein by reference.

U.S. Pat. No. 4,415,723
U.S. Pat. No. 4,458,066
U.S. Pat. No. 4,554,101
U.S. Pat. No. 4,683,195
U.S. Pat. No. 4,683,202
U.S. Pat. No. 4,797,368
U.S. Pat. No. 4,800,159
U.S. Pat. No. 4,816,567
U.S. Pat. No. 4,883,750
U.S. Pat. No. 5,139,941
U.S. Pat. No. 5,187,260
U.S. Pat. No. 5,279,721
U.S. Pat. No. 5,795,715
U.S. Pat. No. 5,840,873
U.S. Pat. No. 5,843,640
U.S. Pat. No. 5,843,650
U.S. Pat. No. 5,843,651
U.S. Pat. No. 5,843,663
U.S. Pat. No. 5,846,708
U.S. Pat. No. 5,846,709
U.S. Pat. No. 5,846,717
U.S. Pat. No. 5,846,726

U.S. Pat. No. 5,846,729
U.S. Pat. No. 5,846,783
U.S. Pat. No. 5,849,481
U.S. Pat. No. 5,849,486
U.S. Pat. No. 5,849,487
U.S. Pat. No. 5,849,497
U.S. Pat. No. 5,849,546
U.S. Pat. No. 5,849,547
U.S. Pat. No. 5,851,772
U.S. Pat. No. 5,853,990
U.S. Pat. No. 5,853,992
U.S. Pat. No. 5,853,993
U.S. Pat. No. 5,856,092
U.S. Pat. No. 5,858,652
U.S. Pat. No. 5,861,244
U.S. Pat. No. 5,863,732
U.S. Pat. No. 5,863,753
U.S. Pat. No. 5,866,331
U.S. Pat. No. 5,866,366
U.S. Pat. No. 5,882,864
U.S. Pat. No. 5,889,136
U.S. Pat. No. 5,900,481
U.S. Pat. No. 5,905,024
U.S. Pat. No. 5,910,407
U.S. Pat. No. 5,912,124
U.S. Pat. No. 5,912,145
U.S. Pat. No. 5,912,148
U.S. Pat. No. 5,916,776
U.S. Pat. No. 5,916,779
U.S. Pat. No. 5,919,626
U.S. Pat. No. 5,919,630
U.S. Pat. No. 5,922,574
U.S. Pat. No. 5,925,517
U.S. Pat. No. 5,928,862
U.S. Pat. No. 5,928,869
U.S. Pat. No. 5,928,905
U.S. Pat. No. 5,928,906
U.S. Pat. No. 5,929,227
U.S. Pat. No. 5,932,413
U.S. Pat. No. 5,932,451
U.S. Pat. No. 5,935,791
U.S. Pat. No. 5,935,825
U.S. Pat. No. 5,939,291
U.S. Pat. No. 5,942,391
U.S. Patent Publn. 20030147966
U.S. Patent Publn. 20030223938
U.S. Patent Publn. 20050143336
Aksentijevich et al., *Hum. Gene Ther.*, 7(9):1111-1122, 1996.
Ausubel et al., In: *Current Protocols in Molecular Biology*, John, Wiley & Sons, Inc, NY, 1994; 1996.
Bellus, *J. Macromol. Sci. Pure Appl. Chem.*, A31(1): 1355-1376, 1994.
Bosher and Labouesse, *Nat. Cell. Biol.*, 2(2):E31-E36, 2000.
Caplen et al., *Gene*, 252(1-2):95-105, 2000.
Chada et al., *Mol. Ther.*, 7:S446, 2003.
Clackson et al., *Nature*, 352:624-628, 1991.
Coffin, In: *Virology*, Fields et al. (Eds.), Raven Press, NY, 1437-1500, 1990.
Consortium, *Nucleic Acids Res.*, 34:D322-326, 2006.
Creighton et al., *J. Mammary Gland Biol. Neoplasia*, 15:253-260, 2010.
Dreyfuss et al., *Am. Rev. Respir. Dis.*, 137:1159-1164, 1988.
Dudek et al., *Free Radic. Biol. Med.*, 31:651-658, 2001.
Elbashir et al., *Nature*, 411(6836):494-498, 2001.
European Appln. 320 308,
European Appln. 329 822

Feigner et al., *Proc. Natl. Acad. Sci. USA*, 84(21):7413-7417, 1987.
Fire et al., *Nature*, 391(6669):806-811, 1998.
Fodor et al., *Science*, 251:767-777, 1991.
Fraley et al., *Proc. Natl. Acad. Sci. USA*, 76:3348-3352, 1979.
Freshney, In: *Animal Cell Culture*, A Practical Approach, $2^{nd}$ Ed., Oxford Press, UK, 1992.
Frohman, In: *PCR Protocols: A Guide To Methods And Applications*, Academic Press, N.Y., 1990.
Gabizon et al., *Cancer Res.*, 50(19):6371-6378, 1990.
Garcia et al., *Oncogene*, 20:2499-2513, 2001.
GB Appln. 2 202 328
GB Appln. 2 202 328
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Grishok et al., *Science*, 287:2494-2497, 2000.
Hacia et al., *Nature Genet.*, 14:441-449, 1996.
Nolen et al., *Invest. New Drugs*, 26:45-51, 2008.
Innis et al., *Proc. Natl. Acad. Sci. USA*, 85(24):9436-9440, 1988.
Inouye and Inouye, *Nucleic Acids Res.*, 13:3101-3109, 1985.
Jia et al., *J. Clin. Invest.*, 113:1318-1327, 2004.
Kaneda et al., *Science*, 243:375-378, 1989.
Karlsson et al., *EMBO J.*, 5:2377-2385, 1986.
Kato et al, *J. Biol. Chem.*, 266:3361-3364, 1991.
Ketting et al., *Cell*, 99(2):133-141, 1999.
Kohler and Milstein, *Nature*, 256:495-497, 1975.
Kwoh et al., *Proc. Natl. Acad. Sci. USA*, 86:1173, 1989.
Li and Wong, *Proc. Natl. Acad. Sci. USA*, 98:31-36, 2001.
Lin and Avery, *Nature*, 402:128-129, 1999.
Liu et al., *Cancer Res.*, 55(14):3117-3122, 1995.
Logullo et al., *Oncol. Rep.*, 23:313-320, 2010.
Luscher et al., *Neth. J. Med.*, 50(5):204-210, 1997.
Ma et al., *Am. J. Physiol. Lung Cell Mol. Physiol.*, 289: L468-477, 2005.
Macejak and Sarnow, *Nature*, 353:90-94, 1991.
Mann et al., *Cell*, 33:153-159, 1983.
Marks et al., *J. Mol. Biol.*, 222:581-597, 1991.
Moitra et al., *Transl. Res.*, 150:253-265, 2007.
Montgomery et al., *Proc. Natl. Acad. Sci. USA*, 95:15502-15507, 1998.
Nichols et al., *Development*, 110:1341-1348, 1990.
Nicolas and Rubinstein, In: *Vectors: A survey of molecular cloning vectors and their uses*, Rodriguez and Denhardt, eds., Stoneham: Butterworth, pp. 494-513, 1988.
Nicolau and Sene, *Biochim. Biophys. Acta*, 721:185-190, 1982.
Nicolau et al., *Methods Enzymol.*, 149:157-176, 1987.
Nonas et al., *Am. J. Physiol. Lung Cell Mol. Physiol.*, 293:L292-302, 2007.
Ohara et al., *Proc. Natl. Acad. Sci. USA*, 86:5673-5677, 1989.
Parsons et al., *Crit. Care Med.*, 33:1-6; discussion 230-232, 2005.
Paskind et al., *Virology*, 67:242-248, 1975.
PCT Appln. PCT/US89/01025
PCT Appln. WO 00/44914
PCT Appln. WO 01/68836
PCT Appln. WO 84/03564.
PCT Appln. WO 88/10315
PCT Appln. WO 89/06700
PCT Appln. WO 90/07641
PCT Appln. WO 98/07408
PCT Appln. WO 99/32619
PCT/US87/00880

Pearson, *Radiology*, 179(1):9-14, 1991.
Pease et al., *Proc. Natl. Acad. Sci. USA*, 91:5022-5026, 1994.
Pelletier and Sonenberg, *Nature*, 334(6180):320-325, 1988.
Peng et al., *Am. J. Respir. Crit. Care Med.*, 169:1245-1251, 2004.
Polyak and Weinberg, *Nat. Rev. Cancer*, 9:265-273, 2009.
Ranieri et al., *JAMA*, 282:54-61, 1999.
Remington's Pharmaceutical Sciences" 15$^{th}$ Ed., 1035-1038 and 1570-1580, 1990.
Revollo et al., *Cell Metab.*, 6(5):363-375, 2007.
Revollo et al., *J Biol Chem.*, 279(49):50754-50763, 2004.
Rubenfeld et al., *N. Engl. J. Med.*, 353:1685-1693, 2005.
Samal et al., *Mol. Cell. Biol.*, 14(2):1431-1417, 1994.
Sambrook and Russell, Molecular Cloning: A Laboratory Manual 3$^{rd}$ Ed., Cold Spring Harbor Laboratory Press, 2001.
Sharp and Zamore, *Science*, 287:2431-2433, 2000.
Sharp, *Genes Dev.*, 13:139-141, 1999.
Shoemaker et al., *Nature Genetics*, 14:450-456, 1996.
Slutsky and Tremblay, *Am. J. Respir. Crit. Care Med.*, 157:1721-1725, 1998.
Smyth-Templeton et al., *DNA Cell Biol.*, 21(12):857-867, 1997.
Solodin et al., *Biochemistry*, 34(41):13537-13544, 1995.
Strauss et al., *PLoS One*, 6:e16186, 2011.
Tabara et al., *Cell*, 99(2):123-132, 1999.
Team RDC, A language and environmental for statistical computing. 2005; ISBN 3-900051-07-0.
Temin, In: *Gene Transfer*, Kucherlapati (Ed.), NY, Plenum Press, 149-188, 1986.
Templeton et al., *Nat. Biotechnol.*, 15(7):647-652, 1997.
The acute respiratory distress syndrome network, *N. Engl. J. Med.*, 342:1301-1308, 2000.
Thierry et al., *Proc. Natl. Acad. Sci. USA*, 92(21):9742-9746, 1995.
Thiery et al., *Cell*, 139:871-890, 2009.
Toole, *Nat. Rev. Cancer*, 4(7):528-539, 2004.
Tremblay et al., *Crit. Care Med.*, 30:1693-1700, 2002.
Tremblay et al., *J. Clin. Invest.*, 99:944-952, 1997.
Tsukamoto et al., *Nat. Genet.*, 9(3):243-248, 1995.
Turley et al., *J. Biol. Chem.*, 277(7):4589-4592, 2002.
Walker et al., *Nucleic Acids Res.* 20(7):1691-1696, 1992.
Ware and Matthay, *N. Engl. J. Med.*, 342:1334-1349, 2000.
Wincott et al., *Nucleic Acids Res.*, 23(14):2677-2684, 1995.
Wong et al., *Gene*, 10:87-94, 1980.
Wu et al., *J. Am. Stat. Assoc.*, 99:909-917, 2004.
Yang and Huang, *Gene Therapy*, 4 (9):950-960, 1997.
Yang and Weinberg, *Dev. Cell*, 14:818-829, 2008.
Ye et al., *Am. J. Respir. Crit. Care Med.*, 171:361-370, 2005.
Yilmaz and Christofori, *Cancer Metastasis Rev.*, 28:15-33, 2009.
Zhu et al., *Science*, 261(5118):209-211, 1993.

What is claimed is:

1. A method for inhibiting tumor progression, the method comprising administering to a subject that has been determined to have NKG2D-expressing cancer cells a composition comprising an anti-NKG2D ligand antibody or NKG2D ligand-binding polypeptide.

2. The method of claim 1, wherein the NKG2D ligand antibody or ligand binding polypeptide inhibitor interferes with the NKG2D-binding of one or more endogenous NKG2D ligands on a cancer cell.

3. The method of claim 1, wherein the polypeptide is an isolated antibody.

4. The method of claim 3, wherein the isolated antibody is a monoclonal antibody, a chimeric antibody, a humanized antibody, a human antibody, or a single chain antibody.

5. The method of claim 3, wherein the isolated antibody is a human antibody.

6. A method for treating cancer comprising administering to NKG2D-expressing cancer cells in a subject that has been determined to have NKG2D-expressing cancer cells a composition comprising an anti-NKG2D ligand antibody or NKG2D ligand-binding polypeptide.

7. The method of claim 6, wherein the polypeptide is an isolated antibody.

8. The method of claim 7, wherein the isolated antibody is a monoclonal antibody, a chimeric antibody, a humanized antibody, a human antibody, or a single chain antibody.

9. The method of claim 7, wherein the isolated antibody is a human antibody.

10. The method of claim 1, wherein the ligand comprises MIC or ULBP.

11. The method of claim 6, wherein the ligand comprises MIC or ULBP.

12. The method of claim 1, wherein the cancer cells comprise ovarian, breast, prostate, or colon cancer cells.

13. The method of claim 6, wherein the cancer cells comprise ovarian, breast, prostate, or colon cancer cells.

14. The method of claim 1, wherein the method comprises administering to the subject a composition comprising a NKG2D ligand-binding polypeptide.

* * * * *

SEQUENCE LISTING

```
<160> NUMBER OF SEQ ID NOS: 64

<210> SEQ ID NO 1
<211> LENGTH: 1770
<212> TYPE: DNA
<213> ORGANISM: Homo sapiens

<400> SEQUENCE: 1
gaggagtgga ttacatattc caacagttgt tattacattg gtaaggaaag aagaacttgg      60
gaagaaagag tttgctggcc tgtgcttcga agaactctga tctgctttct atagataatg     120
aggaagaaat ggtatgtgtg gggacttccc agttggctgt aagttgccat ttgaactaaa     180
cgaaatagat caggaactga ggacatatct aaattttcta gttttataga aggcttttat     240
ccacaagaat caagatcttc cctctctgag caggaatcct ttgtgcattg aagactttag     300
attcctctct gcggtagacg tgcacttata agtatttgat ggggtggatt cgtggtcgga     360
ggtctcgaca cagctgggag atgagtgaat ttcataatta taacttggat ctgaagaaga     420
gtgatttttc aacacgatgg caaaagcaaa gatgtccagt agtcaaaagc aaatgtagag     480
aaaatgcatc tccattttt ttctgctgct tcatcgctgt agccatggga atccgtttca     540
ttattatggt agcaatatgg agtgctgtat tcctaaactc attattcaac caagaagttc     600
aaattccctt gaccgaaagt tactgtggcc catgtcctaa aaactggata tgttacaaaa     660
ataactgcta ccaattttt gatgagagta aaaactggta tgagagccag gcttcttgta     720
tgtctcaaaa tgccagcctt ctgaaagtat acagcaaaga ggaccaggat ttacttaaac     780
tggtgaagtc atatcattgg atgggactag tacacattcc aacaaatgga tcttggcagt     840
gggaagatgg ctccattctc tcacccaacc tactaacaat aattgaaatg cagaagggag     900
actgtgcact ctatgcctcg agctttaaag gctatataga aaactgttca actccaaata     960
catacatctg catgcaaagg actgtgtaaa gatgatcaac catctcaata aaagccagga    1020
acagagaaga gattacacca gcggtaacac tgccaaccga gactaaagga aacaaacaaa    1080
```

```
aacaggacaa aatgaccaaa gactgtcaga tttcttagac tccacaggac caaaccatag    1140
aacaatttca ctgcaaacat gcatgattct ccaagacaaa agaagagaga tcctaaaggc    1200
aattcagata tccccaaggc tgcctctccc accacaagcc cagagtggat gggctggggg    1260
aggggtgctg ttttaatttc taaaggtagg accaacaccc aggggatcag tgaaggaaga    1320
gaaggccagc agatcagtga gagtgcaacc ccaccctcca caggaaattg cctcatgggc    1380
agggccacag cagagagaca cagcatgggc agtgccttcc ctgcctgtgg gggtcatgct    1440
gccactttta atgggtcctc cacccaacgg ggtcagggag gtggtgctgc cccagtgggc    1500
catgattatc ttaaaggcat tattctccag ccttaagatc ttaggacgtt tcctttgcta    1560
tgatttgtac ttgcttgagt cccatgactg tttctcttcc tctctttctt ccttttggaa    1620
tagtaatatc catcctatgt ttgtcccact attgtatttt ggaagcacat aacttgtttg    1680
gtttcacagg ttcacagtta agaaggaatt ttgcctctga ataaatagaa tcttgagtct    1740
catgcaaaaa aaaaaaaaaa aaaaaaaaaa                                    1770

<210> SEQ ID NO 2
<211> LENGTH: 464
<212> TYPE: DNA
<213> ORGANISM: Homo sapiens

<400> SEQUENCE: 2
ctggacttct ctggaccaca gtcctctgcc agaccctgc cagaccccag tccaccatga    60
tccatctggg tcacatcctc ttcctgcttt tgctcccagt ggctgcagct cagacgactc    120
caggagagag atcatcactc cctgcctttt accctggcac ttcaggctct tgttccggat    180
gtgggtccct ctctctgccg ctcctggcag gcctcgtggc tgctgatgcg gtggcatcgc    240
tgctcatcgt gggggcggtg ttcctgtgcg cacgcccacg ccgcagcccc gcccaagatg    300
gcaaagtcta catcaacatg ccaggcaggg gctgaccctc ctgcagcttg gacctttgac    360
ttctgaccct ctcatcctgg atggtgtgtg gtggcacagg aaccccgcc ccaacttttg    420 gattgtaata aaacaattga aacacccaaa aaaaaaaaaa aaaa                    464

<210> SEQ ID NO 3
<211> LENGTH: 22
<212> TYPE: DNA
<213> ORGANISM: Homo sapiens

<400> SEQUENCE: 3
atggggtgga ttcgtggtcg ga                                            22

<210> SEQ ID NO 4
<211> LENGTH: 28
<212> TYPE: DNA
<213> ORGANISM: Homo sapiens

<400> SEQUENCE: 4
cacagtcctt tgcatgcaga tgtacgta                                      28

<210> SEQ ID NO 5
<211> LENGTH: 21
<212> TYPE: DNA
<213> ORGANISM: Homo sapiens

<400> SEQUENCE: 5
gtccaccatg atccatctgg g                                             21
```

```
<210> SEQ ID NO 6
<211> LENGTH: 21
<212> TYPE: DNA
<213> ORGANISM: Homo sapiens

<400> SEQUENCE: 6
gtccaccatg atccatctgg g                                              21

<210> SEQ ID NO 7
<211> LENGTH: 20
<212> TYPE: DNA
<213> ORGANISM: Homo sapiens

<400> SEQUENCE: 7
agccacatcg ctcagacacc                                                20

<210> SEQ ID NO 8
<211> LENGTH: 19
<212> TYPE: DNA
<213> ORGANISM: Homo sapiens

<400> SEQUENCE: 8
gatacccttt tggctcccc                                                 19

<210> SEQ ID NO 9
<211> LENGTH: 22
<212> TYPE: DNA
<213> ORGANISM: Homo sapiens

<400> SEQUENCE: 9
atggcattga ttcgtgatcg aa                                             22

<210> SEQ ID NO 10
<211> LENGTH: 20
<212> TYPE: DNA
<213> ORGANISM: Homo sapiens

<400> SEQUENCE: 10
ttacaccgcc cttttcatgc                                                20

<210> SEQ ID NO 11
<211> LENGTH: 23
<212> TYPE: DNA
<213> ORGANISM: Homo sapiens

<400> SEQUENCE: 11
ggatctccct tctctgctca gag                                            23

<210> SEQ ID NO 12
<211> LENGTH: 20
<212> TYPE: DNA
<213> ORGANISM: Homo sapiens

<400> SEQUENCE: 12
ttacaccgcc cttttcatgc                                                20

<210> SEQ ID NO 13
<211> LENGTH: 20
<212> TYPE: DNA
<213> ORGANISM: Homo sapiens

<400> SEQUENCE: 13
atggaccccc caggctacct                                                20
```

<210> SEQ ID NO 14
<211> LENGTH: 19
<212> TYPE: DNA
<213> ORGANISM: Homo sapiens

<400> SEQUENCE: 14
tcagcctctg ccaggcatg                                            19

<210> SEQ ID NO 15
<211> LENGTH: 23
<212> TYPE: DNA
<213> ORGANISM: Homo sapiens

<400> SEQUENCE: 15
cagagtgaca ctttcccaag atg                                       23

<210> SEQ ID NO 16
<211> LENGTH: 25
<212> TYPE: DNA
<213> ORGANISM: Homo sapiens

<400> SEQUENCE: 16
tcatctgtaa tattgcctct gtgtg                                     25

<210> SEQ ID NO 17
<211> LENGTH: 20
<212> TYPE: DNA
<213> ORGANISM: Homo sapiens

<400> SEQUENCE: 17
aactttggca ttgtggaagg                                           20

<210> SEQ ID NO 18
<211> LENGTH: 20
<212> TYPE: DNA
<213> ORGANISM: Homo sapiens

<400> SEQUENCE: 18
ggagacaacc tggtcctcag                                           20

<210> SEQ ID NO 19
<211> LENGTH: 62
<212> TYPE: DNA
<213> ORGANISM: Homo sapiens

<400> SEQUENCE: 19
ctagacccaa cctactaaca ataatttcaa gagaattatt gttagtaggt tgggttttg    60 at                                                              62

<210> SEQ ID NO 20
<211> LENGTH: 59
<212> TYPE: DNA
<213> ORGANISM: Homo sapiens

<400> SEQUENCE: 20
atcaaaaaac ccaacctact aacaataatt ctcttgaaat tattgttagt aggttgggt    59

<210> SEQ ID NO 21
<211> LENGTH: 79
<212> TYPE: DNA
<213> ORGANISM: Homo sapiens

<400> SEQUENCE: 21
ctagaagctc agacgactcc aggagagaga tcattcaaga gatgatctct ctcctggagt    60
cgtctgagct tttttgat    79

<210> SEQ ID NO 22
<211> LENGTH: 74
<212> TYPE: DNA
<213> ORGANISM: Homo sapiens

<400> SEQUENCE: 22
atcaaaaaaa gctcagacga ctccaggaga gagatcatct cttgaatgat ctctctcctg    60
gagtcgctga gctt    74

<210> SEQ ID NO 23
<211> LENGTH: 67
<212> TYPE: DNA
<213> ORGANISM: Homo sapiens

<400> SEQUENCE: 23
ctagagggta tgtatgcttg gtagtctatc ttcttcttag actaccaagc atacataccc    60
ttttgat    67

<210> SEQ ID NO 24
<211> LENGTH: 65
<212> TYPE: DNA
<213> ORGANISM: Homo sapiens

<400> SEQUENCE: 24
atcaaaaaag ggtatgtatg cttggtagtc taagaagaag atagactacc aagcatacat    60
accct    65

<210> SEQ ID NO 25
<211> LENGTH: 448
<212> TYPE: PRT
<213> ORGANISM: Homo sapiens

<400> SEQUENCE: 25

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Thr Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Tyr Phe Asp Trp Phe Pro Leu Asp Tyr Arg Gly
            100                 105                 110

Gln Gly Thr Leu Val Thr Val Ser Ser Ala Ser Thr Lys Gly Pro Ser
        115                 120                 125

Val Phe Pro Leu Ala Pro Cys Ser Arg Ser Thr Ser Glu Ser Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Lys Thr Tyr Thr Cys Asn Val Asp His
        195                 200                 205

Lys Pro Ser Asn Thr Lys Val Asp Lys Arg Val Glu Ser Lys Tyr Gly
    210                 215                 220

Pro Pro Cys Pro Pro Cys Pro Ala Pro Glu Phe Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser Gln Glu Asp Pro
            260                 265                 270

Glu Val Gln Phe Asn Trp Tyr Val Asp Gly Val Glu Val His Asn Ala
        275                 280                 285

Lys Thr Lys Pro Arg Glu Glu Gln Phe Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Gly Leu Pro Ser Ser Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Gln Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Arg Leu Thr Val Asp Lys Ser
                405                 410                 415

Arg Trp Gln Glu Gly Asn Val Phe Ser Cys Ser Val Met His Glu Ala
            420                 425                 430

Leu His Asn His Tyr Thr Gln Lys Ser Leu Ser Leu Ser Leu Gly Lys
        435                 440                 445

<210> SEQ ID NO 26
<211> LENGTH: 214
<212> TYPE: PRT
<213> ORGANISM: Homo sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Tyr Pro Tyr

```
                85                  90                  95
Thr Phe Gly Gln Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 27
<211> LENGTH: 449
<212> TYPE: PRT
<213> ORGANISM: Homo sapiens

<400> SEQUENCE: 27

Glu Val Gln Leu Val Glu Ser Gly Gly Gly Val Val Arg Pro Gly Gly
1               5                   10                  15

Ser Leu Arg Leu Ser Cys Ala Ala Ser Gly Phe Thr Phe Asp Asp Tyr
            20                  25                  30

Gly Met Thr Trp Val Arg Gln Ala Pro Gly Lys Gly Leu Glu Trp Val
        35                  40                  45

Ser Gly Ile Asn Trp Asn Gly Gly Ser Thr Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Glu Leu Tyr Tyr Tyr Tyr Gly Leu Asp Val Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Pro Cys Pro Ala Pro Glu Phe Leu Gly Gly Pro
225                 230                 235                 240
```

-continued

```
Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys
```

<210> SEQ ID NO 28
<211> LENGTH: 215
<212> TYPE: PRT
<213> ORGANISM: Homo sapiens

<400> SEQUENCE: 28

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160
```

Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
210                 215

<210> SEQ ID NO 29
<211> LENGTH: 121
<212> TYPE: PRT
<213> ORGANISM: Homo sapiens

<400> SEQUENCE: 29

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Thr Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Arg Tyr Phe Asp Trp Phe Pro Leu Asp Tyr Arg Gly
            100                 105                 110

Gln Gly Thr Leu Val Thr Val Ser Ser
        115                 120

<210> SEQ ID NO 30
<211> LENGTH: 108
<212> TYPE: PRT
<213> ORGANISM: Homo sapiens

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Gly Tyr Pro Tyr
                85                  90                  95

Thr Phe Gly Gln Gly Thr Lys Leu Glu Ile Lys Arg
            100                 105

<210> SEQ ID NO 31
<211> LENGTH: 122
<212> TYPE: PRT
<213> ORGANISM: Homo sapiens

<400> SEQUENCE: 31

Glu Val Gln Leu Val Glu Ser Gly Gly Val Val Arg Pro Gly Gly
1               5                   10                  15

Ser Leu Arg Leu Ser Cys Ala Ala Ser Gly Phe Thr Phe Asp Asp Tyr
                20                  25                  30

Gly Met Thr Trp Val Arg Gln Ala Pro Gly Lys Gly Leu Glu Trp Val
            35                  40                  45

Ser Gly Ile Asn Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Arg Glu Arg Glu Leu Tyr Tyr Tyr Tyr Gly Leu Asp Val Trp
            100                 105                 110

Gly Gln Gly Thr Thr Val Thr Val Ser Ser
        115                 120

<210> SEQ ID NO 32
<211> LENGTH: 109
<212> TYPE: PRT
<213> ORGANISM: Homo sapiens

<400> SEQUENCE: 32

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
        50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Phe Thr Phe Gly Pro Gly Thr Lys Val Asp Ile Lys Arg
            100                 105

<210> SEQ ID NO 33
<211> LENGTH: 5
<212> TYPE: PRT
<213> ORGANISM: Homo sapiens

<400> SEQUENCE: 33

Ser Tyr Ser Met Asn
1               5

<210> SEQ ID NO 34
<211> LENGTH: 17
<212> TYPE: PRT
<213> ORGANISM: Homo sapiens

<400> SEQUENCE: 34

Ser Ile Thr Ser Ser Ser Ser Tyr Ile Tyr Tyr Ala Asp Ser Val Lys
1               5                   10                  15

Gly

```
<210> SEQ ID NO 35
<211> LENGTH: 12
<212> TYPE: PRT
<213> ORGANISM: Homo sapiens

<400> SEQUENCE: 35

Asp Arg Arg Tyr Phe Asp Trp Phe Pro Leu Asp Tyr
1               5                   10

<210> SEQ ID NO 36
<211> LENGTH: 11
<212> TYPE: PRT
<213> ORGANISM: Homo sapiens

<400> SEQUENCE: 36

Arg Ala Ser Gln Gly Ile Ser Ser Trp Leu Ala
1               5                   10

<210> SEQ ID NO 37
<211> LENGTH: 7
<212> TYPE: PRT
<213> ORGANISM: Homo sapiens

<400> SEQUENCE: 37

Ala Ala Ser Ser Leu Gln Ser
1               5

<210> SEQ ID NO 38
<211> LENGTH: 9
<212> TYPE: PRT
<213> ORGANISM: Homo sapiens

<400> SEQUENCE: 38

Gln Gln Tyr Asn Gly Tyr Pro Tyr Thr
1               5

<210> SEQ ID NO 39
<211> LENGTH: 5
<212> TYPE: PRT
<213> ORGANISM: Homo sapiens

<400> SEQUENCE: 39

Asp Tyr Gly Met Thr
1               5

<210> SEQ ID NO 40
<211> LENGTH: 17
<212> TYPE: PRT
<213> ORGANISM: Homo sapiens

<400> SEQUENCE: 40

Gly Ile Asn Trp Asn Gly Gly Ser Thr Gly Tyr Ala Asp Ser Val Lys
1               5                   10                  15

Gly

<210> SEQ ID NO 41
<211> LENGTH: 13
<212> TYPE: PRT
<213> ORGANISM: Homo sapiens

<400> SEQUENCE: 41

Glu Arg Glu Leu Tyr Tyr Tyr Tyr Tyr Gly Leu Asp Val
1               5                   10
```

<210> SEQ ID NO 42
<211> LENGTH: 12
<212> TYPE: PRT
<213> ORGANISM: Homo sapiens

<400> SEQUENCE: 42

Arg Ala Ser Gln Ser Val Ser Ser Ser Tyr Leu Ala
1               5                   10

<210> SEQ ID NO 43
<211> LENGTH: 7
<212> TYPE: PRT
<213> ORGANISM: Homo sapiens

<400> SEQUENCE: 43

Gly Ala Ser Ser Arg Ala Thr
1               5

<210> SEQ ID NO 44
<211> LENGTH: 9
<212> TYPE: PRT
<213> ORGANISM: Homo sapiens

<400> SEQUENCE: 44

Gln Gln Tyr Gly Ser Ser Pro Phe Thr
1               5

<210> SEQ ID NO 45
<211> LENGTH: 442
<212> TYPE: PRT
<213> ORGANISM: Homo sapiens

<400> SEQUENCE: 45

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
                20                  25                  30

Tyr Trp Ser Trp Ile Arg Gln Pro Pro Gly Lys Gly Leu Glu Trp Ile
            35                  40                  45

Gly His Ile Ser Tyr Ser Gly Ser Ala Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser Ala Ser Thr Lys Gly Pro Ser Val Phe Pro Leu Ala Pro
        115                 120                 125

Cys Ser Arg Ser Thr Ser Glu Ser Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Lys Thr Tyr Thr Cys Asn Val Asp His Lys Pro Ser Asn Thr Lys
        195                 200                 205

Val Asp Lys Arg Val Glu Ser Lys Tyr Gly Pro Pro Cys Pro Pro Cys
    210                 215                 220

Pro Ala Pro Glu Phe Leu Gly Gly Pro Ser Val Phe Leu Phe Pro Pro
225                 230                 235                 240

Lys Pro Lys Asp Thr Leu Met Ile Ser Arg Thr Pro Glu Val Thr Cys
                245                 250                 255

Val Val Val Asp Val Ser Gln Glu Asp Pro Glu Val Gln Phe Asn Trp
            260                 265                 270

Tyr Val Asp Gly Val Glu Val His Asn Ala Lys Thr Lys Pro Arg Glu
        275                 280                 285

Glu Gln Phe Asn Ser Thr Tyr Arg Val Val Ser Val Leu Thr Val Leu
290                 295                 300

His Gln Asp Trp Leu Asn Gly Lys Glu Tyr Lys Cys Lys Val Ser Asn
305                 310                 315                 320

Lys Gly Leu Pro Ser Ser Ile Glu Lys Thr Ile Ser Lys Ala Lys Gly
                325                 330                 335

Gln Pro Arg Glu Pro Gln Val Tyr Thr Leu Pro Pro Ser Gln Glu Glu
            340                 345                 350

Met Thr Lys Asn Gln Val Ser Leu Thr Cys Leu Val Lys Gly Phe Tyr
        355                 360                 365

Pro Ser Asp Ile Ala Val Glu Trp Glu Ser Asn Gly Gln Pro Glu Asn
370                 375                 380

Asn Tyr Lys Thr Thr Pro Pro Val Leu Asp Ser Asp Gly Ser Phe Phe
385                 390                 395                 400

Leu Tyr Ser Arg Leu Thr Val Asp Lys Ser Arg Trp Gln Glu Gly Asn
                405                 410                 415

Val Phe Ser Cys Ser Val Met His Glu Ala Leu His Asn His Tyr Thr
            420                 425                 430

Gln Lys Ser Leu Ser Leu Ser Leu Gly Lys
        435                 440

<210> SEQ ID NO 46
<211> LENGTH: 215
<212> TYPE: PRT
<213> ORGANISM: Homo sapiens

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu

```
             130                 135                 140
Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
            195                 200                 205

Ser Phe Asn Arg Gly Glu Cys
    210                 215

<210> SEQ ID NO 47
<211> LENGTH: 450
<212> TYPE: PRT
<213> ORGANISM: Homo sapiens

<400> SEQUENCE: 47

Glu Val Gln Leu Val Gln Ser Gly Ala Glu Val Lys Glu Pro Gly Glu
1               5                   10                  15

Ser Leu Lys Ile Ser Cys Lys Asn Ser Gly Tyr Ser Phe Thr Asn Tyr
            20                  25                  30

Trp Val Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Gly Arg Leu Thr Met Phe Arg Gly Ile Ile Ile Gly Tyr Phe Asp Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285
```

-continued

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
450

<210> SEQ ID NO 48
<211> LENGTH: 214
<212> TYPE: PRT
<213> ORGANISM: Homo sapiens

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
            85                  90                  95

Thr Phe Gly Gln Gly Thr Lys Val Glu Ile Lys Arg Thr Val Ala Ala
        100                 105                 110

Pro Ser Val Phe Ile Phe Pro Pro Ser Asp Glu Gln Leu Lys Ser Gly
    115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
    195                 200                 205

Phe Asn Arg Gly Glu Cys
    210

<210> SEQ ID NO 49
<211> LENGTH: 115
<212> TYPE: PRT
<213> ORGANISM: Homo sapiens

<400> SEQUENCE: 49

Gln Val His Leu Gln Glu Ser Gly Pro Gly Leu Val Lys Pro Ser Glu
1               5                   10                  15

Thr Leu Ser Leu Thr Cys Thr Val Ser Asp Asp Ser Ile Ser Ser Tyr
            20                  25                  30

Tyr Trp Ser Trp Ile Arg Gln Pro Pro Gly Lys Gly Leu Glu Trp Ile
        35                  40                  45

Gly His Ile Ser Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Asn Trp Asp Asp Ala Phe Asn Ile Trp Gly Gln Gly Thr Met Val Thr
            100                 105                 110

Val Ser Ser
    115

<210> SEQ ID NO 50
<211> LENGTH: 108
<212> TYPE: PRT
<213> ORGANISM: Homo sapiens

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 51
<211> LENGTH: 123
<212> TYPE: PRT
<213> ORGANISM: Homo sapiens

<400> SEQUENCE: 51

Glu Val Gln Leu Val Gln Ser Gly Ala Glu Val Lys Glu Pro Gly Glu
1               5                   10                  15

Ser Leu Lys Ile Ser Cys Lys Asn Ser Gly Tyr Ser Phe Thr Asn Tyr
            20                  25                  30

Trp Val Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
 50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Gly Arg Leu Thr Met Phe Arg Gly Ile Ile Ile Gly Tyr Phe Asp Tyr
            100                 105                 110

Trp Gly Gln Gly Thr Leu Val Thr Val Ser Ser
            115                 120

<210> SEQ ID NO 52
<211> LENGTH: 107
<212> TYPE: PRT
<213> ORGANISM: Homo sapiens

<400> SEQUENCE: 52

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Trp
                85                  90                  95

Thr Phe Gly Gln Gly Thr Lys Val Glu Ile Lys
            100                 105

<210> SEQ ID NO 53
<211> LENGTH: 5
<212> TYPE: PRT
<213> ORGANISM: Homo sapiens

<400> SEQUENCE: 53

Ser Tyr Tyr Trp Ser
1               5

<210> SEQ ID NO 54
<211> LENGTH: 16
<212> TYPE: PRT
<213> ORGANISM: Homo sapiens

<400> SEQUENCE: 54

His Ile Ser Tyr Ser Gly Ser Ala Asn Tyr Asn Pro Ser Leu Lys Ser
1               5                   10                  15

<210> SEQ ID NO 55
<211> LENGTH: 7
<212> TYPE: PRT
<213> ORGANISM: Homo sapiens

<400> SEQUENCE: 55

Trp Asp Asp Ala Phe Asn Ile
1               5

<210> SEQ ID NO 56
<211> LENGTH: 12
<212> TYPE: PRT
<213> ORGANISM: Homo sapiens

<400> SEQUENCE: 56

Arg Ala Ser Gln Ser Val Ser Ser Tyr Leu Ala
1               5                   10

<210> SEQ ID NO 57
<211> LENGTH: 7
<212> TYPE: PRT
<213> ORGANISM: Homo sapiens

<400> SEQUENCE: 57

Gly Ala Ser Ser Arg Ala Thr
1               5

<210> SEQ ID NO 58
<211> LENGTH: 9
<212> TYPE: PRT
<213> ORGANISM: Homo sapiens

<400> SEQUENCE: 58

Gln Gln Tyr Gly Ser Ser Pro Trp Thr
1               5

<210> SEQ ID NO 59
<211> LENGTH: 5
<212> TYPE: PRT
<213> ORGANISM: Homo sapiens

<400> SEQUENCE: 59

Asn Tyr Trp Val Gly
1               5

<210> SEQ ID NO 60
<211> LENGTH: 17
<212> TYPE: PRT
<213> ORGANISM: Homo sapiens

<400> SEQUENCE: 60

Ile Ile Tyr Pro Gly Asp Ser Asp Thr Arg Tyr Ser Pro Ser Phe Gln
1               5                   10                  15

Gly

<210> SEQ ID NO 61
<211> LENGTH: 14
<212> TYPE: PRT
<213> ORGANISM: Homo sapiens

<400> SEQUENCE: 61

Leu Thr Met Phe Arg Gly Ile Ile Ile Gly Tyr Phe Asp Tyr
1               5                   10

<210> SEQ ID NO 62
<211> LENGTH: 11
<212> TYPE: PRT
<213> ORGANISM: Homo sapiens

<400> SEQUENCE: 62

Arg Ala Ser Gln Ser Val Ser Ser Tyr Leu Ala
1               5                   10

```
<210> SEQ ID NO 63
<211> LENGTH: 7
<212> TYPE: PRT
<213> ORGANISM: Homo sapiens

<400> SEQUENCE: 63

Asp Ala Ser Asn Arg Ala Thr
1               5

<210> SEQ ID NO 64
<211> LENGTH: 9
<212> TYPE: PRT
<213> ORGANISM: Homo sapiens

<400> SEQUENCE: 64

Gln Gln Arg Ser Asn Trp Pro Trp Thr
1               5
```